(12) United States Patent
Domany et al.

(10) Patent No.: US 7,599,933 B2
(45) Date of Patent: Oct. 6, 2009

(54) COUPLED TWO-WAY CLUSTERING ANALYSIS OF DATA

(75) Inventors: Eytan Domany, Rechovot (IL); Gad Getz, Haifa (IL); Erel Levine, Tel Aviv (IL)

(73) Assignee: Yeda Research And Development Co. Ltd., Rehovot (IL)

( * ) Notice: Subject to any disclaimer, the term of this patent is extended or adjusted under 35 U.S.C. 154(b) by 361 days.

(21) Appl. No.: 11/154,542

(22) Filed: Jun. 17, 2005

(65) Prior Publication Data

US 2005/0240563 A1 Oct. 27, 2005

Related U.S. Application Data

(62) Division of application No. 10/220,702, filed as application No. PCT/IL01/00228 on Mar. 9, 2001, now Pat. No. 6,965,831.

(30) Foreign Application Priority Data

Mar. 9, 2000 (IL) .................................. 134994

(51) Int. Cl.
*G06F 17/30* (2006.01)
*G06F 19/00* (2006.01)

(52) U.S. Cl. ............................................ 707/7; 702/19

(58) Field of Classification Search ........................ None
See application file for complete search history.

(56) References Cited

U.S. PATENT DOCUMENTS

| 6,021,383 A | 2/2000 | Domany et al. |
| 6,965,831 B2 | 11/2005 | Domany et al. |
| 2003/0059818 A1 | 3/2003 | Domany et al. |

FOREIGN PATENT DOCUMENTS

| WO | WO 98/47087 | 10/1998 |
| WO | WO 01/00228 | 1/2001 |
| WO | WO 01/67061 | 9/2001 |

OTHER PUBLICATIONS

Golub et al. "Molecular Classfication of Cancer: Class Discovery and Class Prediction by Gene Expression Monitoring", Science, 286: 531-537, 1999. Esp. p. 533-534.
Alon et al. "Broad Patterns of Gene Expression Revealed by Clustering Analysis of Tumor and Normal Colon Tissues Probed by Oligonucleotide Arrays", Proceedings of the National Academy of Sciences USA, 96: 6745-6750, 1999. Esp. p. 6748-6749.
Lockhart et al. "Expression Monitoring by Hybridization to High-Density Oligonucleotide Arrays", Nat. Biotech., 14:1675-1680, 1996.
De Risi et al. "Exploring the Metabolic and Genetic Control of Gene Expression on A Genomic Scale", Science, 278: 680-686, 1997.
Eisen et al. "Cluster Analysis and Display of Genome-Wide Expression Patterns", PNAS, 95:14683-14868, 1998.
Perou et al. Distinctive Gene Expression Patterns in Human Mammary Epithelial Cells and Breast Cancers, PNAS, 96: 9212-9217, 1999.
Lander "Array of Hope", Nature Genetics, 21: 3-4, 1999.
Zhang "Promoter Analysis of Co-Regulated Genes in the Yeast Genome", Comput. Chem., 23: 233-250, 1999.
Blatt et al. "Super-Paramagnetic Clustering of Data", Physical Review Letters, 76: 3251-3254, 1996.
Domany "Super-Paramagnetic Clustering of Data—The Definite Solution of An Ill-Posed Problem", Physica A, 263:158-169, 1999.
Getz et al. "Super-Paramagnetic Clustering of Yeast Gene Expression Profiles", Physica A, 279: 457-464, 2000.
Getz et al. "Coupled Two Way Clustering of Gene Microarray Data", PNAS, 97(22):12079-12084, 2000. p. 12079, 12084.
Blatt et al. "Data Clustering Using A Model Granular Magnet", Neural Computation, 9:1805-1842, 1997.
Wang et al. Cluster Monte-Carlo Algorithms, Physica A., 167: 565-579, 1990.
Schena et al. "Parallel Human Genome Analysis: Microarray-Based Expression Monitoring of 1000 Genes", PNAS, 93:10614-10619, 1996.
Califano et al. "Analysis of Gene Expression Microarrays for Phentype Classification". Proc. Int. Conf. Intell. Syst. Mol. Biol., 8: 75-85, 2000.
Cheng et al. "Biclustering of Expression Data", Proc. Int. Conf. Intell. Syst. Mol. Biol., 8: 93-103, 2000.
Te Poele et al. "RNA Synthesis Block by 5,6-Dichloro-1-Beta-D-Ribofuranosylbenzimidazole (DRB) Triggers P53-Dependent Apoptosis in Human Colon Carcinoma Cells", Oncogene, 18: 5765-5772, 1999.

*Primary Examiner*—John S Brusca

(57) ABSTRACT

A novel coupled two-way clustering approach to gene microarray data analysis, for identifying subsets of the genes and samples, such that when one of these items is used to cluster the other, stable and significant partitions emerge. The method of the present invention preferably uses iterative clustering in order to execute this search in an efficient way. This approach is especially suitable for gene microarray data, where the contributions of a variety of biological mechanisms to the gene expression levels are entangled in a large body of experimental data. The method of the present invention was applied to two gene microarray data sets, on colon cancer and leukemia. By identifying relevant subsets of the data and focusing on these subsets, partitions and correlations were found that were masked and hidden when the full data set was used in the analysis.

11 Claims, 15 Drawing Sheets
(14 of 15 Drawing Sheet(s) Filed in Color)

Step 1. Initialization

1a. Let $v_0^g$ be the cluster of all genes, and $v_0^s$ be the cluster of all samples.

1b. Initialize sets of gene clusters, $V^g$, and sample clusters, $V^s$, such that $V^g = \{v_0^g\}$ and $V^s = \{v_0^s\}$.

1c. Add each known class of genes as a member of $V^g$, and each known class of samples as a member of $V^s$.

1d. Define a new set $W = \emptyset$. This set is needed to keep track of clustering analyses that have already been performed.

Step 2. For each pair $(v^g, v^s) \in (V^g \times V^s) \setminus W$:

2a. Apply the clustering algorithm on the genes of $v^g$ using the samples of $v^s$ as its features and vice versa.

2b. Add all the robust gene clusters generated by Step 2a to $V^g$, and all the robust sample clusters to $V^s$.

2c. Add $(v^g, v^s)$ to $W$.

Step 3. For each new robust cluster $u$ in either $V^g$ or $V^s$ define and store a pair of labels $P_u = (u_o, u_f)$. Of these, $u_o$ is the cluster of objects which were clustered to find $u$, and $u_f$ is the cluster of features used in that clustering.

Step 4. Repeat Step 2 until no new clusters are added to either $V^g$ or $V^s$.

Fig. 1

COUPLED TWO-WAY CLUSTERING ANALYSIS OF DATA

RELATED PATENT APPLICATIONS

This application is a Divisional of U.S. patent application Ser. No. 10/220,702, filed Sep. 5, 2002, which is a National Phase of PCT Patent Application No. PCT/IL01/00228, filed Mar. 9, 2001, which claims the benefit of Israel Patent Application No. 134994, filed Mar. 9, 2000. The contents of the above applications are all incorporated by reference.

FIELD OF THE INVENTION

The present invention is of a method for analyzing large amounts of data through iterative clustering, and in particular, of such a method which is useful for the analysis of gene microarray data.

BACKGROUND OF THE INVENTION

DNA microarray technologies have enabled the expression levels of thousands of genes during various cellular processes to be monitored simultaneously [1, 2]. In a typical experiment expression levels of thousands of genes are recorded over a few tens of different samples [3, 5, 6]. By "sample", it is meant any kind of living matter that is being tested, such as different tissues [3], cell populations collected at different times [4] and so forth. Hence arrays that contain $10^5$-$10^6$ measurements must be analyzed, thereby giving rise to a new computational challenge: to make sense of such massive amounts of expression data [7, 8].

The aims of such analyses are typically to (a) identify cellular processes which affect the gene expression pattern; (b) search for different phases of these processes, by grouping the samples into clusters which share an expression pattern; (c) find genes which differentiate between these clusters, and hence take part in the relevant biological process and (d) explain the role these genes play in the process.

The sizes of the datasets and their complexity call for multi-variant clustering techniques which are essential for extracting correlated patterns from the swarm of data points in multidimensional space. The aim of clustering is to identify the natural classes present in a set of N data points, or objects, each one represented by means of D different measured features. That is, the data can be viewed as N points in a D dimensional space. The aim of clustering algorithms is to reveal the structure of this cloud of points, for example, to determine whether the data consists of a single cloud or several clouds, or whether the constituent components have any internal structure, revealed when the data are viewed with higher resolution. Under most circumstances the data points must be partitioned into clusters; it makes no sense to try and divide the features which characterize the data points into classes.

The situation with gene microarray data is different, in that clustering analysis can be performed in two ways. The first views the $n_s$ samples as the N objects to be clustered, with the $n_g$ genes' levels of expression in a particular sample playing the role of the features, that represent that sample as a point in a $D=n_g$ dimensional space. The different phases of a cellular process emerge from grouping together samples with similar or related expression profiles. The other, not less natural way looks for clusters of genes that act correlatively on the different samples. This view considers the $N=n_g$ genes as the objects to be clustered, each represented by its expression profile, as measured over all the samples, as a point in a $D=n_s$ dimensional space.

Gene microarray data are special in that both ways of looking at them have meaning and are of interest. Having realized this, Eisen et al and Alon et al applied such two-way clustering to data from experiments on yeast cell cycle [4] and colon cancer [3]. However, they clustered first the samples and then the genes completely independently, with no coupling at all between the two clustering procedures. In principle the two clustering operations could have been carried out in different places at different times; the results of one operation were not allowed to affect the other.

The current approach in the literature is to cluster the samples on the basis of as many genes as possible (usually the number used is limited by eliminating samples with the weakest signals). Similarly, when clustering genes, there is a tendency to rely on features accumulated from as many samples (even taken from different experiments! [4]) as possible. The philosophy behind this approach may be termed "holistic", as it attempts to extract information from the larger, overall, complete picture.

However, this approach clearly has a number of disadvantages. First, large amounts of data must be analyzed, which may require extensive resources, whether in human work hours, computational power or experimental procedures. Second, the signal-to-noise ratio may be quite poor with this approach, given the emphasis on analyzing the overall picture. Third, the actual points of interest may be obscured in the larger sets of data to analyze. All of these drawbacks clearly render currently available clustering techniques both less effective and less robust.

SUMMARY OF THE INVENTION

The background art does not teach or suggest a method for coupled two-way clustering analysis, which enables structural features to be derived through simultaneous usage of two sets of differentiating characteristics. Instead, the background art focuses on clustering analyses with a single set of differentiating features, which are not connected to each other. Thus, even if such a clustering process is performed more than once according to the background art methods, the lack of connection between the features used for the clustering analysis significantly lowers the utility and strength of the resulting analyses.

There is therefore an unmet need for, and it would be useful to have, a method for clustering analysis which couples different sets of features for greater power in the resultant analysis, and which also is performed iteratively, in order to obtain coupled clustering analysis, particularly for the analysis of massive data sets, such as gene expression data for example.

For example, a first plurality of items, such as genes, can optionally be used to partition a second plurality of items, such as the samples that are analyzed, and vice versa. This ability to partition each of two separate groups of items according to the other group can be described as the "two-way" aspect of the method of the present invention. However, the "coupled" aspect of the method of the present invention particularly differentiates the present method from other background art methods. This "coupled" aspect can be generally described as follows: first, discover a subgroup of the first plurality of items, such as a subgroup of genes. Of course any other subgroup of a plurality of items which are linked according to some relationship through the data could be used. Second, use this subgroup of genes to partition the samples, or more generally, use the subgroup of the first group of items to partition the second group of items or any subgroup of it. The advantage of the "coupled" aspect of the method of the present invention is that the present invention can uncover interactions/partitions which would otherwise be lost in the noise of the overall data.

The combination enables the combinatorial search space to be much more effectively examined.

The method of the present invention can optionally be implemented as a software program for execution on any suitable type of computer. Regardless of the implementation, the functional steps performed by the method could be described as a plurality of instructions performed by a data processor.

According to the present invention there is provided a method for separating a first plurality of objects and a second plurality of objects into at least two groups, the method being performed by a data processor, the method comprising: dividing the first plurality of objects into a first plurality of object subsets; and partitioning, the second plurality of objects according to at least one of the first plurality of object subsets to form at least two groups of the second plurality of objects.

However, it should be noted that the phrase "plurality of objects is separated to at least two groups" is not intended to be limiting in any way, as optionally the objects may not in fact separate into a plurality of groups, if no "natural" separation exists. The optional lack of separation of the plurality of objects, depending upon the information which is used to attempt to cluster or partition these objects, is actually an advantage of the method of the present invention, since it enables the lack of natural subgroups to be detected. By contrast, other methods in the background art always break data into a plurality of subgroups. Thus, the method of the present invention does not attempt to artefactually decompose a plurality of objects into subgroups, thereby giving a false or inaccurate result. For the purposes of clarity, the following discussion mentions separating the plurality of objects into a plurality of subgroups, it being understood that this description does not limit the present invention to the possibility that such a plurality of subgroups is always created by the method of the present invention, but instead also encompasses the possibility that no such subgroups are created.

Preferably, the method further comprises: partitioning at least a portion of the first plurality of objects according to at least one group of the second plurality of objects to form a plurality of subset groups of the first plurality of objects. More preferably, said at least a portion of the first plurality of objects is the entirety of the first plurality of objects. Alternatively, said at least a portion of the first plurality of objects is at least one subgroup of the first plurality of objects.

Optionally, each of the first plurality of objects is characterized according to at least one feature, and the division of the first plurality of objects is performed by: applying a clustering algorithm on the first plurality of objects according to said at least one feature to form a plurality of object subsets; and detecting at least one robust cluster from said plurality of object subsets. Preferably, said clustering algorithm is the superparamagnetic clustering algorithm.

Optionally, the method is repeated until no additional subgroups are detected. Preferably, no additional subgroups are detected for both the first plurality of objects and the second plurality of objects.

According to preferred embodiments of the present invention, the process of partitioning at least a portion of the first plurality of objects according to at least one group of the second plurality of objects is performed by partitioning a plurality of subset groups of the first plurality of objects according to a known classification.

According to other preferred embodiments of the present invention, the method further comprises: analyzing each group of said at least two groups of the second plurality of objects by comparing said group of said at least two groups of the second plurality of objects to an entirety of the second plurality of objects to determine if said group is differentiated from the second plurality of objects.

According to still other preferred embodiments of the present invention, the method further comprises: analyzing each subset group of the first plurality of objects by comparing said subset group of the first plurality of objects to an entirety of the first plurality of objects to determine if said subset group is differentiated from the first plurality of objects. Preferably, the analysis is performed according to a statistical test for similarity. More preferably, the first plurality of objects is normalized before being divided. Alternatively or additionally, the second plurality of objects is normalized before being partitioned.

According to yet other preferred embodiments of the present invention, the first plurality of objects are genes and the second plurality of objects are samples for being analyzed according to a characteristic of said genes. Preferably, said samples are characterized according to expression levels of said genes. Optionally, said genes forming a cluster characterize a pathological state of a plurality of subjects, said samples being obtained from said plurality of subjects. Also optionally, said genes forming a cluster participate together in a biological process.

According to a preferred embodiment of the present invention, said genes are characteristic of samples taken from subjects having a cancerous condition. More preferably, at least one characteristic of said genes partitions said samples according to a type of cancer in said cancerous condition. Most preferably, said at least one characteristic of said genes is an expression profile of said genes. Also most preferably, said expression profile is determined as an expression matrix, such that the division of said samples into subgroups according to said expression profile for said genes is performed with said expression matrix.

Optionally, said at least one characteristic of said genes is an effect of treatment on said subjects.

According to still another embodiment of the present invention, the first plurality of objects are keywords and the second plurality of objects are documents containing said keywords.

According to another embodiment of the present invention, there is provided a method for separating at least one of a first plurality of objects and a second plurality of objects into at least two groups if a natural separation exists within at least one of the first plurality of objects and of the second plurality of objects, each of the first plurality of objects being related to at least one of the second plurality of objects, the method being performed by a data processor, the method comprising: dividing the first plurality of objects into a first plurality of object subsets; and partitioning the second plurality of objects according to at least one of said first plurality of object subjects to form at least two groups of the second plurality of objects.

According to yet another embodiment of the present invention, there is provided a method for analyzing data, available in the form of an array of numbers, wherein each row of the array represents measurements of the values taken by a particular attribute over several samples and each column represents the measurements of the various attributes taken for a particular sample.

Preferably, for the analysis of gene expression data taken from several tissues, the attributes are different genes for which expression levels were measured and the samples are human tissues or other biological material for which the expression levels of the genes have been determined.

More preferably, the method further comprises performing cluster analysis in two ways, over the samples and over the genes, wherein the two ways of clustering are coupled: each cluster of genes constitutes a probe which is used to cluster any group of samples, and vice versa. Most preferably, the method is iterative and whenever stable clusters are generated, they are used to further search for partitions (clusters) in the other dimension.

Optionally, gene clusters are used to look for partitions of tissues and tissue clusters are used to look for correlated clusters of genes. Also optionally, the method is used in conjunction with any clustering algorithm. Preferably, the method is used in conjunction with the superparamagnetic clustering algorithm. More preferably, the method uses a measure for the stability of clusters and identification of said stable clusters narrows significantly the groups (clusters) that are to be tested as probes.

Optionally, the method yields clusters of genes of correlated expression profiles that may participate in the same biological process. Preferably, said groups of genes relate to administration of pharmaceutical drugs, or differentiate one type of cancer from another, or reflect the change of experimental protocol in a colon-cancer treatment. More preferably, said method identifies tissues of groups of patients, or tissues subjected to different experimental protocols, or identifies different types of cancer. Most preferably, said method identifies different types of leukemia.

According to yet another embodiment of the present invention, there is provided an apparatus for carrying out a method according to any of the above embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings, wherein:

FIG. 1 is a flowchart of an exemplary coupled two-way clustering method according to the present invention. The input of the algorithm is the full expression matrix. The output is a set $V^g$ of stable gene clusters and a set $V^s$ of stable sample clusters. For each stable cluster u, found in a clustering operation, the clusters which provided the objects and those that served as the features for this operation are stored as a label $P_u$.

DESCRIPTION OF THE PREFERRED EMBODIMENTS

Figure 2:
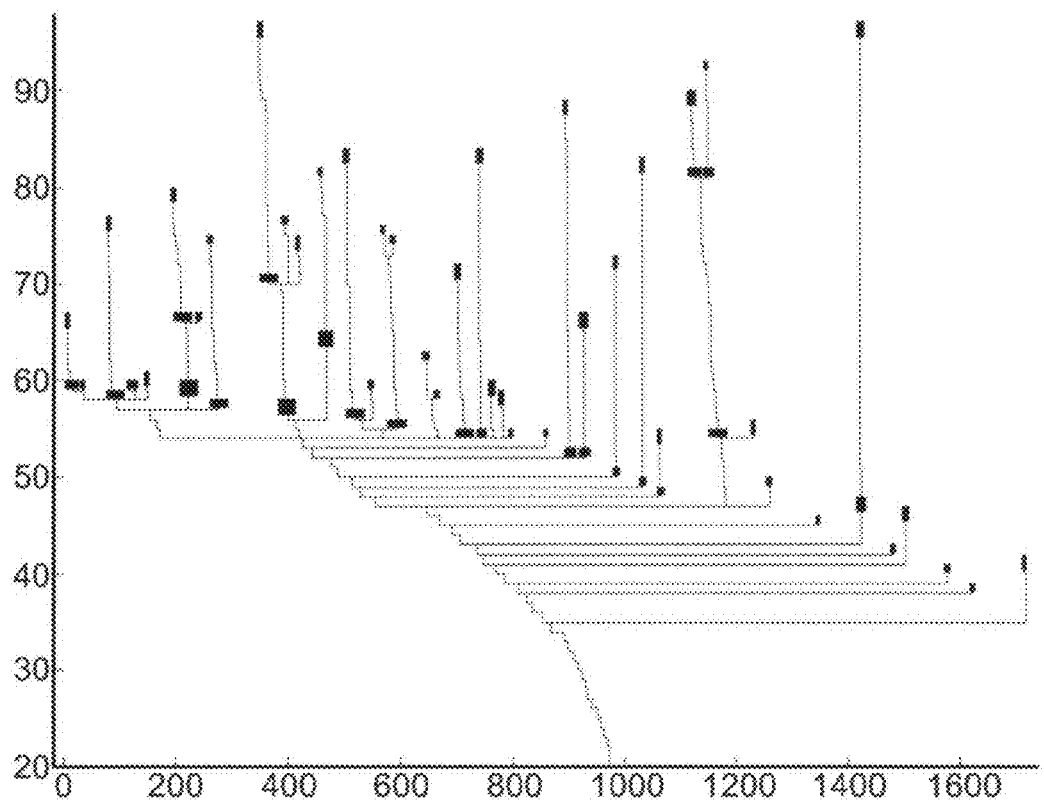
FIG. 2. shows a dendrogram of genes in colon experiment, based on all samples.

The present invention is of a method for coupled two-way clustering, which is able to identify subsets of objects when characterized by a set of features, such that stable and significant partitions emerge. The method of the present invention preferably uses iterative clustering in order to execute this search in an efficient way. Optionally, both the features can be used to cluster the objects and vice versa, for a complete examination of the effect of coupling these two parameters on the emergence of stable clusters and partitions.

For example, according to the method of the present invention, a first plurality of items, such as genes, can optionally be used to partition a second plurality of items, such as the samples for being analyzed according to a characteristic of the genes, and vice versa. For example, the samples can be analyzed in order to determine the expression level of a particular gene or genes, such that the expression level would be an example of a characteristic of the genes. This ability to partition each of two separate groups of items according to the other group can be described as the "two-way" aspect of the method of the present invention. However, the "coupled" aspect of the method of the present invention particularly differentiates the present method from other background art methods. This "coupled" aspect can be generally described as follows: first, discover a subgroup of the first plurality of items, such as a subgroup of genes. Of course any other subgroup of a plurality of items which are linked according to some relationship through the data could be used. Second, use this subgroup of genes to partition the samples, or more generally, use, one at a time, every subgroup of the first group of items to partition the second group of items, and any of its subgroups that have been already identified. The advantage of the "coupled" aspect of the method of the present invention is that the present invention can uncover interactions/partitions which would otherwise be lost in the noise of the overall data.

The coupled two-way clustering method of the present invention is a general way to analyze gene microarray data, and may optionally be used with any suitable clustering algorithm, such that the present invention is not limited to any particular clustering algorithm. A particularly preferred clustering algorithm, which is used in the examples described in greater detail below, is the super-paramagnetic clustering algorithm (SPC) [9, 10, 11, 12]. This algorithm is especially suitable for gene microarray data analysis due to its robustness against noise and its "natural" ability to identify stable clusters.

This algorithm is described in greater detail in U.S. Pat. No. 6,021,383, filed on Oct. 7, 1996 and which is hereby incorporated by reference as if fully set forth herein. U.S. Pat. No. 6,021,383 discloses a method and apparatus for partitioning a data set for clustering, which is based on the physical properties of an inhomogeneous ferromagnet. No assumption needs to be made regarding the underlying distribution of the data. A Potts spin is assigned to each data point and an interaction between neighboring points is introduced, whose strength is a decreasing function of the distance between the neighbors. This magnetic system exhibits three phases. At very low temperatures it is completely ordered; i.e. all spins are aligned. At very high temperatures the system does not exhibit any ordering and in an intermediate regime clusters of relatively strongly coupled spins become ordered, whereas different clusters remain uncorrelated. This intermediate phase is identified by a jump in the order parameters. The spin—spin correlation function is used to partition the spins and the corresponding data points into clusters.

According to preferred embodiments of the present invention, both the number of the features which are used to cluster the data and the number of resultant clustered data points are preferably reduced during the iterative clustering process, such that the data points that are clustered also constitute a subset of the total number available. This approach is particularly preferred for sets of data in which ultimately relatively few data points may be important. For example, only a small subset of the genes may participate in any given cellular process of interest, such that the large majority of genes act as a source of noise that may mask the correlated activity of the small subgroup of interest. Furthermore, for these types of sets of data, the process of interest is expected to take place only in a subset of the samples; again, by focusing on a small subset, the amount of noise induced by the other samples may be reduced, thereby amplifying the "signal". Hence, the two-way coupled clustering analysis is expected to ultimately locate a relatively small subset F of features (either genes or samples) in order to reveal the structure of a subset O of objects (either samples or genes). The advantages of this approach are demonstrated in greater detail below.

The examples described in greater detail below show the efficacy of the coupled two-way clustering algorithm of the present invention, as implemented with the super-paramagnetic clustering algorithm (SPC), which is known in the art [9, 10, 11, 12]. The coupled two-way clustering method of the present invention was applied to two gene microarray data sets, one from a colon cancer experiment [3] and the other from a leukemia experiment [5]. Also as described in greater detail below, the method of the present invention was able to identify an alternative differentiation between tissues (rather than the expected normal/tumor classification) in the colon cancer experiment, which was then shown to correspond to a change of experimental protocol. In addition, the analysis also revealed evidence for the central role played by epithelial cells in the process of tumor development. In the leukemia experiment, T-cell related genes were shown to be suitable for separating B-cell versus T-cell types of ALL (acute lymphoblastic leukemia)-leukemia. Furthermore, groups of genes were identified whose expression profile differentiates between AML leukemia patients that received treatment and those patients who did not receive such treatment.

The next sections describe the basic method of the present invention for coupled two-way clustering (Section 1); suitable clustering algorithms and similarity measures for use with the method of the present invention (Section 2); various applications of the method of the present invention (Section 3); and various conclusions from the example applications (Section 4). It should emphasized that although the method of the present invention is described with regard to the analysis of gene microarray data, this is for the purposes of discussion only and is without any intention of being limiting. In particular, Sections 3 and 4 provide additional illustrative non-limiting examples of other types of data to which the method of the present invention may also be applied.

Section 1. Coupled Two Way Clustering

Section 1 describes the basic coupled two-way clustering method of the present invention, including a detailed description of each step of the method. In addition, a basic description of the utility of applying the method of the present invention to the analysis of gene microarray data is also provided, although again it should be understood that this is for the purposes of description only and is without any intention of being limiting.

With regard to the basic exemplary algorithm itself, the results of every gene microarray experiment can be summarized as a set of numbers, which are organized in an expression level matrix A. A row of this matrix corresponds to a single gene, while each column represents a given sample. The entry $A_{ij}$ is the normalized expression level of gene i in sample j. The preferred normalization method is described in greater detail below with regard to Section 2, "Clustering method and similarity measures".

In a typical experiment, simultaneous expression levels of thousands of genes are considered. Gene expression is influenced by the cell type, cell phase, external signals and more [13]. The expression level matrix is therefore the result of all these processes mixed together. The goal is to separate and identify these processes, and to extract as much information as possible about them. The main point is that the biological process of interest may involve a relatively small subset of the genes that are present on a microarray; the large majority of the genes constitute a noisy background which may mask the effect of the small subset. The same result may occur with respect to samples.

The aim of the coupled two-way clustering is to overcome such problems. The method of the present invention attempts to identify subsets of genes $G_\mu$ (to be used as the feature set F) and a subset of samples $S_\alpha$ (which play the role of the set of objects O), such that when the samples are clustered on the basis of their expression profiles over the genes $G_\mu$, a stable and statistically significant partition of $S_\alpha$ is obtained. Alternatively, genes may be selected to play the role of O and samples to serve as F, that yield a partition of the genes of $G_\mu$ into stable meaningful clusters, on the basis of their expression profiles over the samples $S_\alpha$.

The method is illustrated and its advantages are highlighted in an example, based on artificial data, presented in Appendix A.

Clearly the number of ways for choosing sets of genes and samples is exponentially large and one needs an efficient way to search for groups that have the desired property. The method of coupled two-way clustering executes such a search in the following iterative manner. If no information on the data is available and/or should not be used, the process starts with the full data set, and the samples and the genes are then clustered [3]. Next a cluster of genes is chosen, and using these genes as the feature set F to represent the samples, the samples are clustered. The object set O can contain either all the samples or any subset (of sample clusters). Similarly, a cluster of the samples can be chosen and then used as the feature set F to identify stable clusters of genes (which play the role of the objects). All of the stable clusters that are generated, of both genes and samples, are preferably stored, and denoted as $v^g$ (gene cluster), while the samples are denoted as $v^s$. The gene clusters are accumulated in a list $V^g$ and the sample clusters in $V^s$. Furthermore, all of the information about the clustering process that generated every cluster, such as a gene cluster $v_g$, is preferably also stored. More preferably, this information is stored by storing pointers that indicate which sample clusters were used as the feature set; which was the set of genes O that was clustered; as well as pointers to the clusters which were generated when the genes of $v^g$ were used as feature set F to cluster samples.

When new clusters are found, they are used in the next iteration. At each iteration step, a subset of the objects (either samples or genes) is clustered by using a subset of the features (genes or samples). The procedure optionally and preferably only stops when no new relevant information is generated.

The outcome of the coupled two-way clustering algorithm are the final sets $V^g$ and $V^s$, and the pointers that identify how all stable clusters of genes and samples were generated.

The precise step by step definition of an exemplary two-way coupled clustering method according to the present invention is given in FIG. 1. Standard notation is used to describe the method. For example, if U is a subset of V, U\V denotes the complement of U, i.e. all elements of V that are not members of U. The input of the coupled two-way clustering method for the present invention is an expression level matrix A. From this matrix, sets of data points are generated and a pairwise similarity measure is calculated between these sets of data points. The coupled two-way clustering utilizes a clustering algorithm that can identify statistically significant clusters in such a data set. The choice of clustering algorithm, the similarity measure it utilizes, and the manner in which robust, stable clusters are chosen is discussed in greater detail below (Section 2). Even though the choice of the particular clustering algorithm affects the performance of the coupled two-way clustering, the method is applicable for any reasonable choice of such an algorithm.

More specifically, the method of FIG. 1 is preferably performed as follows. In the first stage, initialization is performed. Let $v^g_0$ be the cluster of all genes, and $v^s_0$ be the cluster of all samples. Initialize sets of gene clusters, $V^g$, and sample clusters, $V^s$, such that:

$$V^g = \{v^g_0\}$$

and $$V^s = \{v^s_0\}$$

Add each known class of genes as a member of $V^g$, and each known class of samples as a member of $V^s$. Next, define a new set $W=\emptyset$. This set is needed to keep track of clustering analyses that have already been performed.

Next, for each pair:

$$(v^s, v^g) \in (V^g \times V^s) \setminus W$$

the following steps are performed in the second stage.

First apply the clustering algorithm on the genes of $v^g$ using the samples of $v^s$ as its features and vice versa. Add all the robust gene clusters generated by the application of clustering algorithm to $V^g$, and all the robust sample clusters to $V^s$. Next, add $(v^g, v^s)$ to W.

In the third stage, for each new robust cluster u in either $V^g$ or $V^s$, define and store a pair of labels $P_u = (u_o, u_f)$. Of these, $u_o$ is the cluster of objects which were clustered to find u, and $u_f$ is the cluster of features used in that clustering.

In the fourth stage, the second stage is preferably repeated until no new clusters are added to either $V^g$ or $V^s$.

After the above method has been performed, the clusters obtained by coupled two-way clustering can be analyzed. The output of coupled two-way clustering has two important features. First, it provides a broad list of gene and sample clusters. Second, for each cluster (of samples, say), the subset (of samples) which was clustered to find that subset is known, and the clusters of the second type, such as of genes, which were used as features are also known. Similarly, the identity of those clusters, which can be found by using it as the feature set for clustering, are also known. The present description concerns a brief, non-limiting selection of examples of the possible uses for this kind of information. Implementations of the particular uses listed here are described in Section 3 below.

First, this information can optionally be used to identify genes that partition the samples according to a known classification. This particular application is supervised. Denote by C a known classification of the samples, say into two classes, $c_1, c_2$. The coupled two-way clustering method of the present invention provides an easy way to rank the clusters of genes in $V^g$ by their ability to separate the samples according to C. It should be noted that coupled two-way clustering not only provides a list of candidate gene clusters to be further examined, but also a unique method of testing these candidates.

First, for each cluster of samples $v^s$ in $V^s$, two scores are evaluated, for purity and efficiency, which reflect the extent to which assignment of the samples to $v^s$ corresponds to the classification C. These figures of merit are defined (for both $c_1, c_2$) as $$\text{purity}(S \mid C) = \frac{|v^s \cap c_i|}{v^s}$$

efficiency $(v^s|C)=$

Once a cluster $v^s$ with high purity/efficiency has been found, each of the cluster (or $$\frac{|v^s \cap c_i|}{c_i}$$

clusters) of genes that were used as the feature set can be read to yield $v^s$ in the clustering procedure. Clustering, as opposed to classification, discovers only those partitions of the data which are, in some sense, "natural". Hence by this method, the most natural group of genes that can be used to induce a desired classification is identified.

Needless to say, a gene cluster $v^g$ that was obtained from the coupled two-way clustering method of the present invention can also be tested by using more standard statistics, such as the t-test [14] or the Jensen-Shannon distance [15, 16]. Both compare the expression levels of the genes of $v^g$ on the two groups of samples, $c_1$, $c_2$, which are partitioned according to C. Alternatively, the genes of $v^g$ can optionally be used to train a classifier to separate the samples according to C [5], after which the success of the classifier at measuring whether the expression levels of the genes in $v^g$ correspond to the classification can then be determined.

New partitions of the data can then be discovered. For example, every cluster $v^s$ of $V^s$ contains a subset of all the samples for which the members have been linked to each other, and separated from the other samples on the basis of the expression levels of some feature; with regard to the current example, this feature is the co-expressed subset of genes. It is reasonable therefore to argue that the cluster $v^s$ has been formed for some biological or experimental reason.

As a first step to understand the reason for the formation of a robust cluster $v^s$, the cluster should preferably be related to some previously known classification (for example, in terms of purity and efficiency). Clusters which cannot be associated with any known classification should preferably be inspected more carefully. In the case of the present example, useful hints for the meaning of such a cluster of samples may come from the identity of the cluster of genes which was used to find it. Clearly, the coupled two-way clustering clusters can be used in the same way to interpret clusters of genes which were not previously known to belong to the same process.

Coupled two-way clustering is also a sensitive tool to identify sub-partitions within the data. For example, some of the sample clusters in $V^s$ may have emerged from clustering a subset of the samples, such as $v^s_0$. These clusters reflect a sub-partition of the samples which belong to $v^s_0$. When trying to cluster the full sample set, this sub-partition may be missed, since other samples, unrelated to this subset, are masking it.

Sometimes this procedure reveals that a subgroup $v^s_1$ of $v^s_0$ constitutes a stable sub-cluster, whereas the other samples of $v^s_0$, such as $v^s_0 \backslash v^s_1$, do not form a stable cluster. Nevertheless, the fact that $v^s_1$ is a robust cluster raises the possibility that a relevant sub-partition of $v^s_0$ does exist, which should be investigated.

Furthermore, the coupled two-way clustering method of the present invention can also reveal a conditional correlation among genes. The coupled two-way clustering method collects stable gene clusters in $V^g$. In many cases the same groups of genes may be added to $V^g$ more than once. This is caused by the fact that some genes are co-regulated in all cells, and therefore are clustered together, no matter which subset of the samples is used as the feature set. For example, ribosomal proteins are expected to be clustered together for any set of samples which is not unreasonably small.

Some gene clusters, however, are different, as they are co-regulated only in a specific subset of samples, which can be termed "conditional correlation". The identity of the sample cluster which reveals the conditionally correlated gene cluster is clearly important to understand the biological process which makes these genes correlated.

Section 2. Clustering Method and Similarity Measures

Section 2 describes various similarity measures which can optionally be used with the coupled two-way clustering method of the present invention. As previously described, any suitable similarity measure can optionally be used, although certain similarity measures may be preferred for certain types of data sets, as described in greater detail below with regard to gene microarray data, for example.

As mentioned above, any reasonable choice of clustering method and definition of stable clusters can be used within the framework of coupled two-way clustering. This section describes the particularly preferred clustering algorithm and similarity measure which was used for this particular example of the operation of the present invention, since they were found to be particularly suitable to handle the special properties of gene microarray data.

The super-paramagnetic clustering (SPC) algorithm is a hierarchical clustering method recently introduced by Blatt et al [17], which was found to be particularly robust for the operation of the present invention. Full details of the algorithm [18] and the underlying philosophy [10] are given elsewhere; only a brief description is provided herein, which does not require acquaintance with any concept borrowed from physics.

The input required for SPC is a distance or similarity matrix $d_{ij}$ between the N data points that are to be clustered. From such a distance matrix, a graph is constructed, whose vertices are the data points, and whose edges identify neighboring points. Two points i and j are called neighbors (and connected by an edge) if they satisfy the K-mutual-neighbor criterion, ie. if and only if j is one of the K nearest points to i and vice versa. A weight $J_{ij}>0$ is associated with each edge, which decreases as the distance between points i and j increases.

Every possible assignment of the data points to clusters is equivalent to a partition S of this weighted graph, with the connected components of the partitioned graph playing the role of clusters. Every partition S is characterized by its cost H[S], which is the sum of the weights $J_{ij}$ of all the edges that were cut in order to create the corresponding partition of the weighted graph. There is an exponential number of possible partitions which can be generated. These range from partitions with all points assigned to the same single cluster, which has the lowest possible cost H=0, to partitions corresponding to the maximal H, obtained when all edges are cut and each point constitutes its own individual cluster. By fixing the value of H, control is provided over the resolution at which the data is to be clustered.

However, even if the cost is constrained to lie within a certain interval $E<H<E+\Delta$, there may be a very large number of partitions that satisfy this constraint. Rather than selecting a particular partition, preferably an ensemble of partitions is created, assigning equal statistical weight to every partition of the graph whose cost lies in the prescribed interval, optionally and more preferably using the maximum entropy principle. Next, the probability $p_{ij}$, that in this ensemble of partitions the vertices i and j belong to the same cluster, is preferably measured for every pair of neighboring points i, j. $p_{ij}$ is called the pair correlation function, which is used to identify the clusters that constitute the output of the algorithm, such that a high correlation means that at the working resolution E, the two data points belong to the same cluster. That is, a new graph is generated by connecting two points ij by an edge, provided $p_{ij}>\frac{1}{2}$. Optionally, a slightly more complicated procedure is used to generate this graph from $p_{ij}$, as is described in the background art [18]. This procedure is optionally and more preferably performed at a sequence of resolutions. As the resolution parameter E is increased from its lowest value, a dendrogram of nested partitions, or clusters, is generated.

This simple explanation of the algorithm needs to be supplemented by one caveat; rather than generating an ensemble of equally likely partitions at a fixed E, the procedure operates at a fixed average cost, tuned by a Lagrange multiplier which can be denoted by 1/T. The ensemble is then preferably generated by a Monte Carlo sampling procedure [19].

The procedure outlined above may be considered to be analogous to the simulation of a Potts ferromagnet at thermal equilibrium, where the weights $J_{ij}$ are the couplings between neighboring spins, T is the temperature and $p_{ij}$ is the spin-spin correlation function. At T=0 the system is in its (fully aligned) ground state, all neighbor pairs have correlations $p_{ij}$=1 and a single cluster is obtained. As the resolution T increases, phase transitions occur, with the single ferromagnetic domain breaking up into sub-clusters. These transitions can be very sharp, in which case the corresponding splits can be easily identified. Clusters continue to decompose as the system is "heated" further, until at a sufficiently high "temperature", each point forms its own cluster (see FIG. 2 for an illustration of this process).

Blatt et al showed that the SPC algorithm is robust against variation of its parameters, initialization and against noise in the data [18]. Due to these distinct advantages, the SPC algorithm is especially suitable for gene microarray data analysis. No prior knowledge of the structure of the data is assumed. The SPC algorithm provides information about the different self-organizing regimes of the data; the number of "macroscopic" clusters is an output of the algorithm; hierarchical organization of the data is reflected in the manner clusters merge or split when the control parameter (the "temperature" T) is varied.

The SPC algorithm has the further advantage of providing clear identification of stable clusters. The clusters generated by SPC are governed by the value of a continuous control parameter T, which controls the resolution at which clustering is performed. This parameter can be used to provide a natural measure for the stability of any particular cluster by the range of temperatures $\Delta T$ at which the cluster remains unchanged. A stable cluster is expected to 'survive' throughout a large $\Delta T$, one which constitutes a significant fraction of the range it takes the data to break into single point clusters. Inspection of the gene dendrogram of FIG. 2 reveals stable clusters and stable branches.

Each node of the dendrogram of FIG. 2 represents a cluster; only clusters of size larger than eight genes are shown. The last such clusters of each branch, as well as non-terminal clusters that were selected for presentation and analysis are shown as boxes. The circled boxes represent the clusters that are discussed below. Proximity of two clusters along the horizontal axis indicates that the corresponding temporal expression profiles are not very different [3]. The vertical axis represents the resolution, controlled by the "temperature" T. The vertical position of a node or box is determined by the value of T at which it splits. A high vertical position indicates that the cluster is stable, i.e. contains a fair number of closely spaced data points (genes with similar expression profiles).

The gene expression array can also optionally be normalized for the operation of the method of the present invention, as described with regard to the following example. The Pearson correlation is commonly used as the similarity measure between genes or samples [20, 4, 3]. This measure conforms with the intuitive biological notion of what it means for two genes to be co-expressed; this statistic captures similarity of the "shapes" of two expression profiles, and ignores differences between the magnitudes of the two series of measurements [4]. The correlation coefficient is high between two genes that are affected by the same process, even if each has a different gain due to the process, over different background expression levels (caused by other processes). One problem of using the correlation coefficient is that its reliability depends on the absolute expression level of the compared genes, since a positive correlation between two highly expressed genes is much more significant than the same value between two poorly expressed genes. This information is ignored in the clustering process.

However, correlations do not always capture similarity between samples. For example, consider two samples taken at different stages of some process, with the expression levels of a family of genes much below average in one sample and much higher in the other. Even if the expression levels of the two samples over these genes are correlated, preferably they are assigned into different clusters. Furthermore, the distance between the two samples should be affected by the statistical significance of their expression differences. This can be obtained if the Euclidean distance between normalized gene expressions is used as the distance measure between samples.

Therefore the following normalization scheme was used for this example. Denote by D the matrix of the raw data. Each row of this matrix represents a single gene, while each column represents a sample. The entry $D_{ij}$ is the measured expression level of gene i in sample j. D is a $n_g \times n_t$ matrix, where $n_g$ is the number of genes and $n_t$ is the number of samples.

The expression level matrix is then preferably normalized in two steps. First, divide each column by its mean:

$$D'_{ij} = D_{ij}/\overline{D}_{ij} \text{ and } \overline{D}_j = \frac{1}{n_g}\sum_{i=1}^{n_g} D_{ij}$$

Each row is then normalized, such that its mean vanishes, and the norm is one:

$$A_{ij} = \frac{D'_{ij} - \overline{D}'_i}{\|D'_i\|} \text{ where } \overline{D}'_i = \frac{1}{n_t}\sum_{j=1}^{n_t} D'_{ij} \text{ and } \|D'_i\|^2 = \sum_{j=1}^{n_t} (D'_{ij} - \overline{D}'_i)^2$$

For genes and samples, the Euclidean distance is used as the dissimilarity measure. For two genes (rows of A), the Euclidean distance is closely related to the Pearson correlation between them. For two samples, the Euclidean distance between their respective columns provides the dissimilarity measure.

Section 3. Applications

Section 3 describes various applications of the method of the present invention for coupled two-way clustering through a number of examples. It should be noted that these examples are intended only for illustrative purposes and are without any intention of being limiting. The coupled two-way clustering method of the present invention is therefore applied to two gene microarray experiment data sets. In this particular section, only the results which were obtained by coupled two-way clustering and which could not be found using a straightforward clustering analysis are described. Full lists of several clusters mentioned in this section can be found in Appendix B.

The first example concerns the analysis of leukemia samples. Data available at [21], obtained by Golub et al [5] from seventy-two samples collected from acute leukemia patients at the time of diagnosis, was analyzed. Forty-seven cases were diagnosed as ALL (acute lymphoblastic leukemia) and the other twenty-five were diagnosed as AML (acute myeloid leukemia). RNA prepared from the bone marrow mononuclear cells was hybridized to high-density oligonucleotide microarrays, produced by Affymetrix (3380 Central Exway, Santa Clara, Calif. 95051, USA), containing 6817 human genes.

After rescaling the data in the manner described by Golub et al, only those genes whose minimal expression over all samples is greater than twenty were selected. As a result of this thresholding, operation, 1753 genes remained. The resulting array was then normalized as described in Section 2, to give the 1753×72 expression level matrix A.

Figure 3:
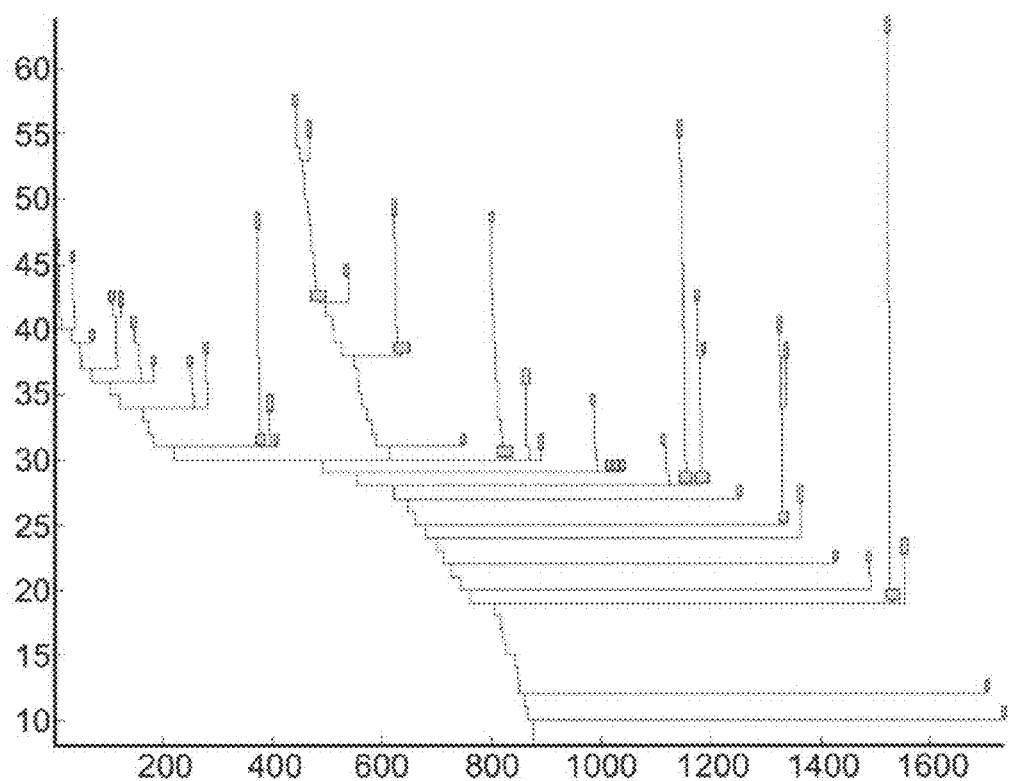
FIG. 3 shows a dendrogram of genes in leukemia experiment, based on all samples.
Figure 5:
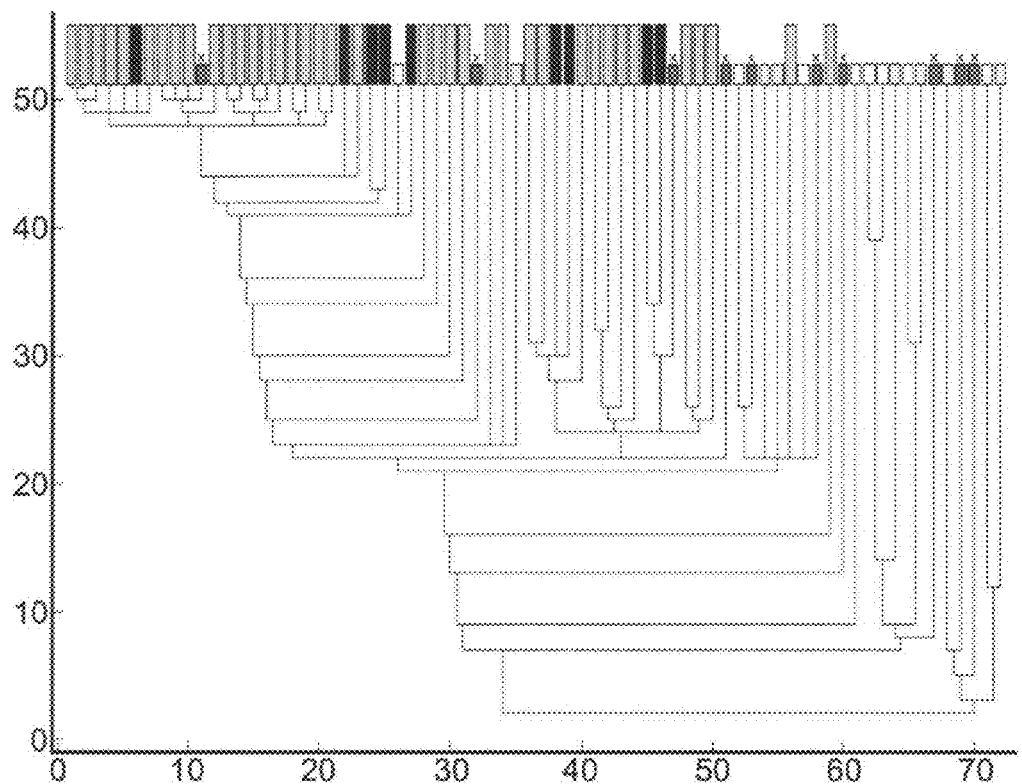
FIG. 5 shows a dendrogram of all samples in the leukemia experiment, based on the genes of cluster LG1. Code as for FIG. 4.
Figure 6:
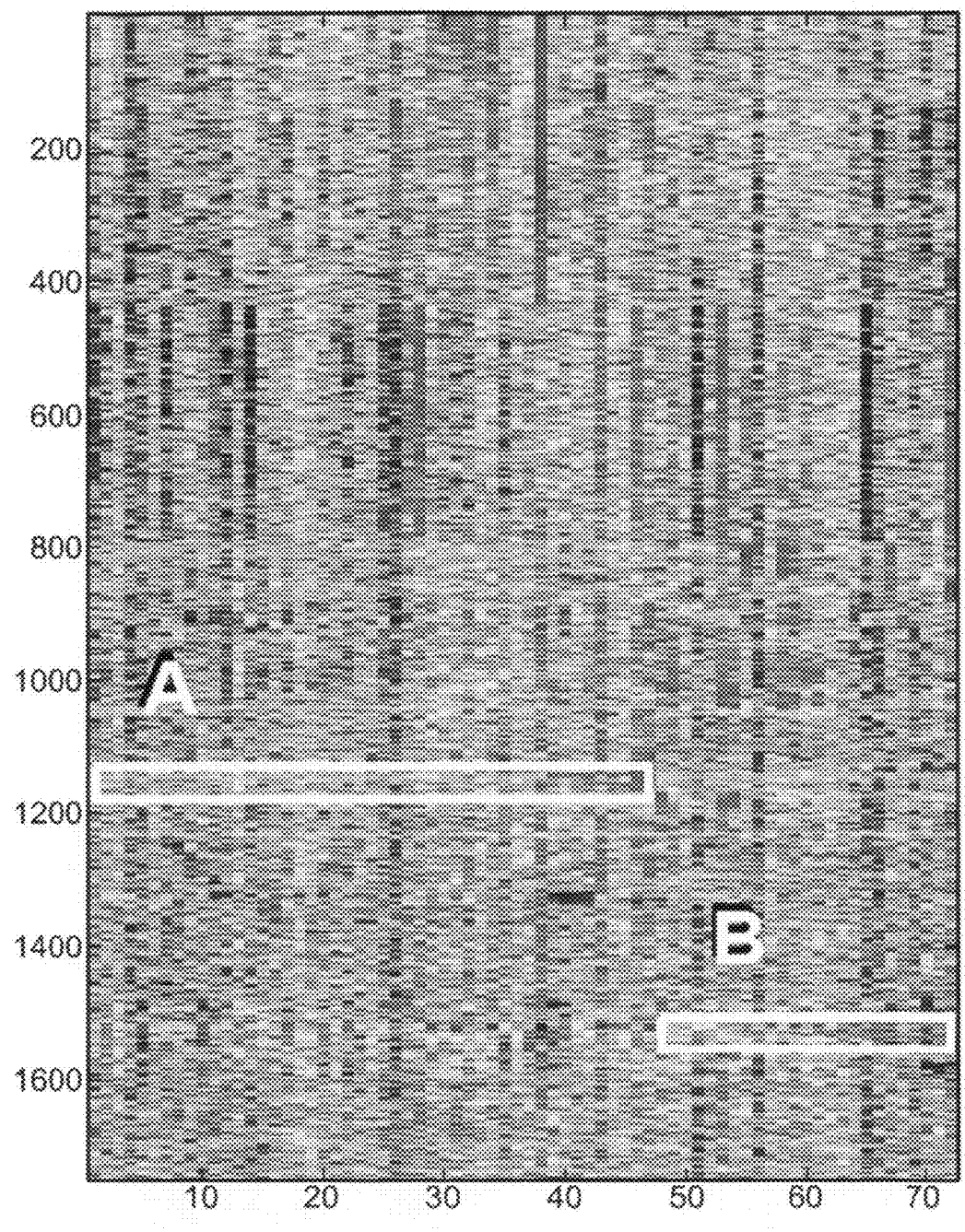
FIG. 6 shows an expression level matrix of the leukemia experiment. Rows, corresponding to genes, are ordered according to the gene clusters of FIG. 3. The two boxes contain expression data from ALL patients (A) measured on one gene cluster and AML patients (B), on another gene cluster.
Figure 7:
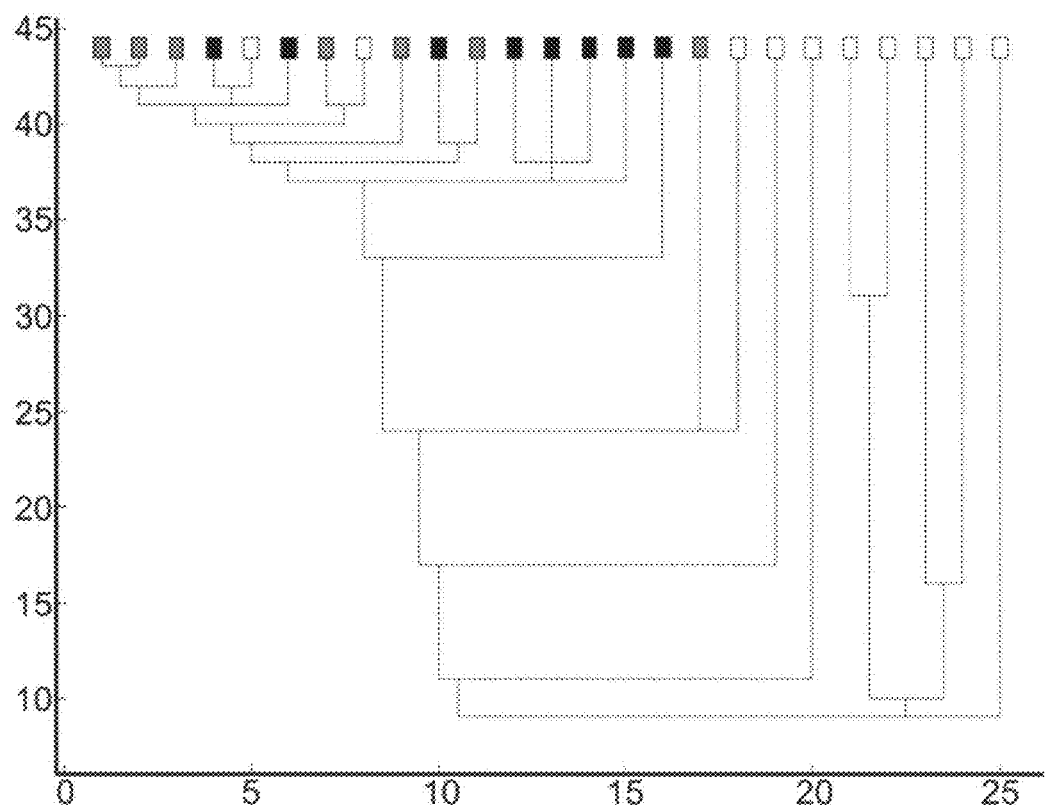
FIG. 7 shows the results of clustering AML leukemia samples, based on genes of cluster LG4. Patients whose treatment succeeded (black) or failed (gray) are clustered into a stable cluster.

First, these genes were clustered by using all samples as the feature set. The resulting dendrogram of genes is shown in FIG. 3. Next, all samples were clustered by using all of the genes as the feature set. The resulting dendrogram of samples is given in FIG. 7. The various gene clusters of FIG. 3 were then used, one at a time, to cluster all the samples. The dendrogram obtained using only the gene cluster LG1 (see below) is shown in FIG. 5. The rows of the expression matrix were permuted according to the ordering [3] of the gene clusters of FIG. 3. A color-coded permuted expression level matrix is shown in FIG. 6.

Two iterations of the coupled two-way clustering algorithm, as previously described in Section 1, were found to be sufficient to converge to forty-nine stable gene clusters (LG1-49) and thirty-five stable sample clusters (LS1-35). In particular, four results from these findings are described in greater detail below in order to demonstrate the power of the method of the present invention to solve problems listed in Section 1.

The first such result is the ability of the method of the present invention to identify genes that partition the samples according to a known classification. Since the ALL/AML classification of the patients is known in advance, the present invention can be used to search for groups of genes that distinguish between the two classes. To test a given gene cluster the mean expression of all of its genes is calculated for every patient. Next, the forty-five values derived for the ALL patients are postulated to have been drawn from one probability distribution and the values of the AML patients are postulated to have been drawn from another probability distribution. The t-test statistic for these distributions was then evaluated, and five gene clusters were found with an exceptionally high t-test score. This means that the genes from these five clusters have very different expression levels for ALL and AML patients.

An alternative approach to this question is to examine whether the samples split into two clusters according to the ALL/AML diagnosis, when the expression levels of genes from a single gene cluster are used as the characteristic features. A cluster of samples is then identified as ALL or AML only if both its purity and efficiency exceed 0.75, measured with respect to the known classification.

The data analysis showed that only a single gene cluster (LG1) provided features that produce ALL or AML clusters. This cluster indeed has a high t-test score. For the other high t-test gene clusters, the overlap between the two clouds of sample points, corresponding to ALL and AML, was too high to allow separation into two distinct clusters. If the data points of the two types of samples form a single continuous cloud, the SPC algorithm cannot break them into two clusters even when there exists a clear dividing hypersurface that separates the two types of samples. In such cases the SOM algorithm used by Goloub et al [5] and the WARD agglomerative algorithm [22, 16] may be preferred, for example. Both of these algorithms can break a single large group or cloud of points into two subclouds of (usually) equal volumes, which may then correspond to the correct partition.

Figure 4:
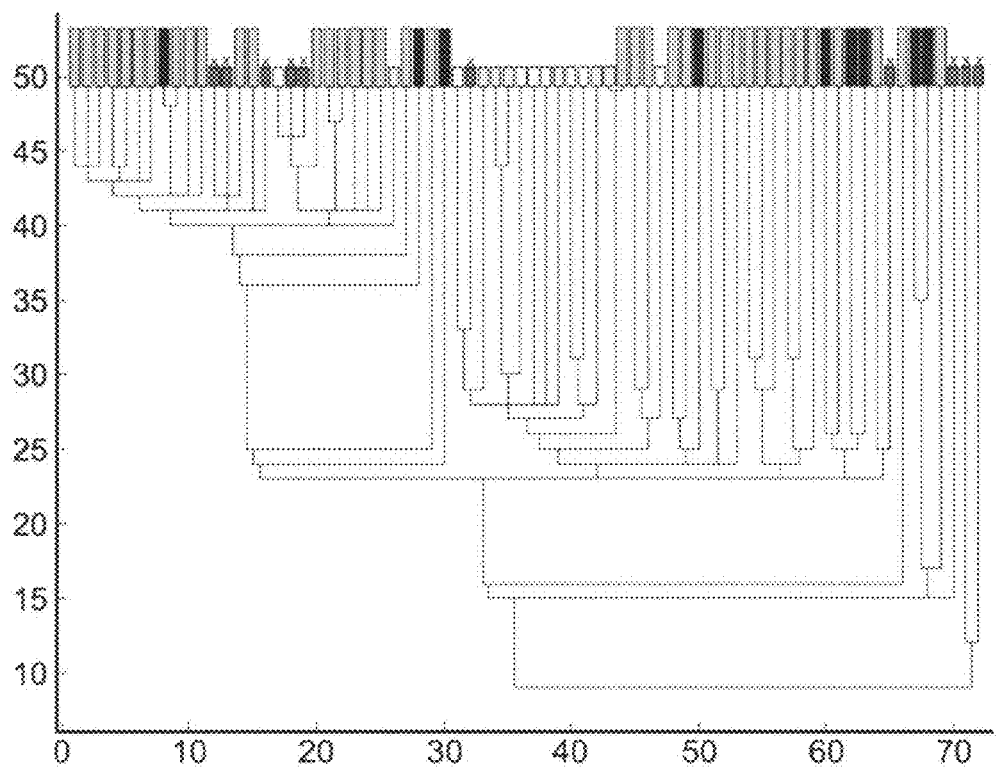
FIG. 4 shows a dendrogram of all samples in the leukemia experiment, based on all genes. High boxes are ALL samples (T-ALL in gray, B-ALL in black). Short boxes are AML samples (coded according to treatment results—white for success, diagonal hatch marks for failure, black with an "x" for unknown).

To demonstrate the power of coupled two-way clustering, it should be noted that when the expression levels of all of the genes are used as the features, the samples do not break into distinct stable ALL and AML clusters, whereas when the single gene cluster LG1 is used, the samples can be broken into distinct stable ALL and AML clusters (see FIGS. 4 and 5).

The present invention is also suitable for discovering new partitions of existing data sets. For example, the stable sample clusters can be optionally searched for unknown partitions of the data. Attention is then preferably focused on sample clusters which were repeatedly found to be stable. One such cluster, denoted LS1, may be of interest; it includes thirty-seven samples and was found to be stable when either a cluster of twenty-seven genes (LG2) or another unrelated cluster of thirty-six genes (LG3) was used to provide the features. LG3 includes many genes that participate in the glycolysis pathway. Due to lack of additional information about the patients, the biological origin of the formation of this sample cluster cannot be further analyzed.

As a further step, the data sets can optionally be analyzed in order to identify subpartitions within the clusters of data points. The samples that were identified as AML patients (leaving out ALL samples) were used as the object set. These samples were then analyzed according to the method of the present invention, in an attempt to cluster these samples by sequentially applying each of the gene clusters as the feature set. Emergent stable subpartitions of the AML patients were then analyzed. Indeed, using a twenty-eight gene cluster (LG4) as the feature set, a stable cluster, LS2, of sixteen samples was found (see FIG. 7). It contains fourteen out of the fifteen samples that were taken from patients that underwent treatment and whose treatment results were known (either success or failure). No information about treatment was available in the data for any of the other AML patients. Some of the sixteen genes of this cluster, (LG4), are ribosomal proteins and others are related to cell growth (see Appendix B). Apparently these genes have different expression patterns for those AML patients who received treatment, as opposed to those patients who did not receive such treatment.

Figure 8:
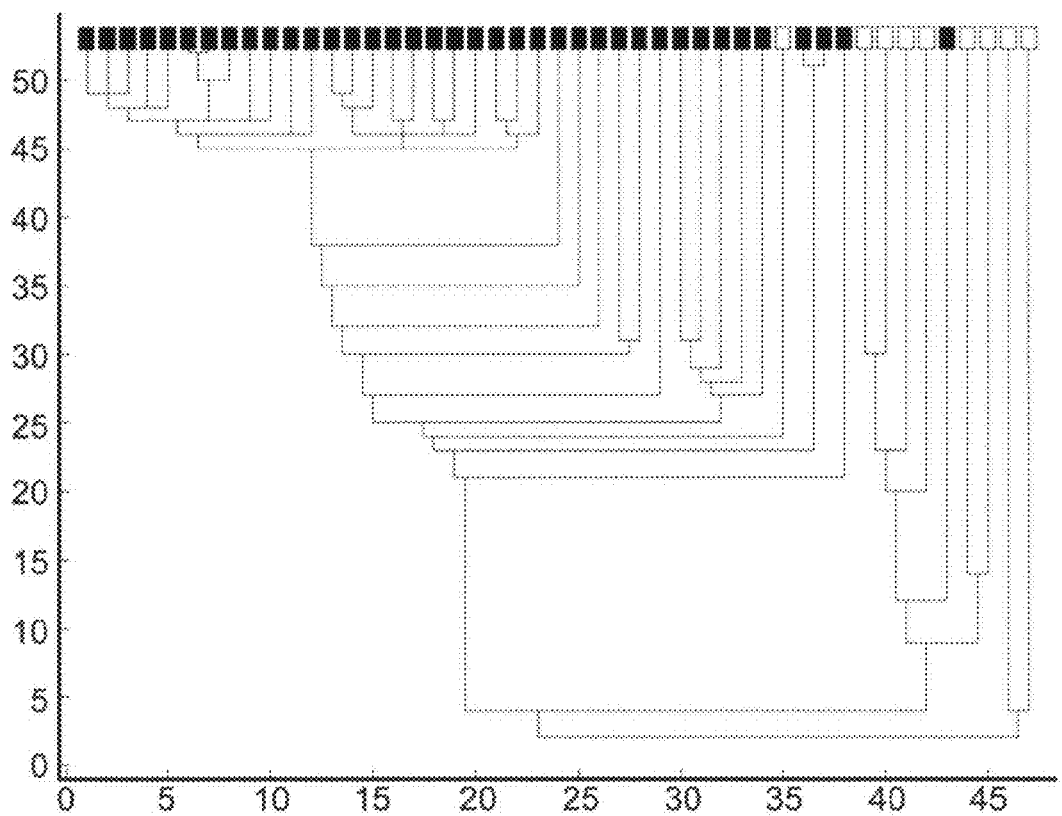
FIG. 8 shows the result of clustering ALL leukemia samples, based on genes of cluster LG5. Good separation between T-ALL (black) and B-ALL (white) is obtained.

The same procedure was then repeated, but discarding AML samples and keeping only the ALL samples. When any one of five different gene clusters (LG4-8) were used to provide the features, the ALL samples were found to break into two stable clusters. The first stable cluster consists mostly of T-Cell ALL patients and the second stable cluster contains mostly B-Cell ALL patients. One of these gene clusters, (LG5), with the ability to separate between the T-Cell and B-Cell varieties, contains twenty-nine genes; indeed, many of the genes are T-cell related. Using (LG5) as the feature set, and the ALL samples as the object set, two clear sub-clusters were found; LS3, of seven samples and LS4, of thirty-eight samples (see FIG. 8). The first sub-cluster, LS3, captured six out of the nine patients diagnosed as T-ALL; the second, LS4, contained thirty-seven out of the thirty-eight B-ALL patients. On the other hand, when all of the genes were used to cluster all samples, no such clear separation into T-ALL vs B-ALL was observed.

It should be noted that another gene cluster, LG6, which gave rise to T-ALL/B-ALL differentiation, contains many HLA histocompatability genes.

These results demonstrate how coupled two-way clustering can optionally be used to characterize different types of cancer. For instance, imagine that the nature of the sub-classification of ALL had not been known. On the basis of these results, the existence of two distinct sub-classes of ALL could be predicted; moreover, by the fact that many genes which induce separation into these sub-classes are either T-Cell related or HLA genes, these sub-classes could be suspected to be immunology related.

As a different possible use of these results, note that some of the genes in the T-Cell related gene cluster LG5 have no determined function, and may be candidates for new T-Cell genes. This assumption is supported both by the fact that these genes were found to be correlated with other T-Cell genes, and by the fact that they support the differentiation between T-ALL and B-ALL.

For further analysis of gene clusters, conditional correlations among genes may be considered. Most of the gene clusters are stable against changing the set of samples that are used to provide the features for clustering. This means that most gene clusters contain genes that are highly correlated over any subset of the samples. However, a few gene clusters were found which exhibit conditional correlations. The genes of two groups, LG9 and LG10, are correlated over the ALL samples; they do not form clusters when either in the AML or the full sample set are used. Hence the genes of LG10 probably take part in a biological process which is characteristic of ALL samples. On the other hand, three groups of genes, LG11, LG12 and LG13, were found to form clusters only over the AML sample set.

As a second illustrative example of the operation of the method of the present invention, a set of data for colon cancer was analyzed. This data set contains 40 colon tumor samples and 22 normal colon samples, which were analyzed with an Affymetrix oligonucleotide array complementary to more than 6500 human genes and expressed sequence tags (ESTs) (Affymetrix Hum6000 array; see Alon et al [3] for details). Following Alon et al [3], only the 2000 genes of greatest minimal expression over the samples were considered. The data set is publicly available at [23]. The data were normalized as previously described in Section 2, to obtain a 2000×62 expression level matrix A.

Figure 9:
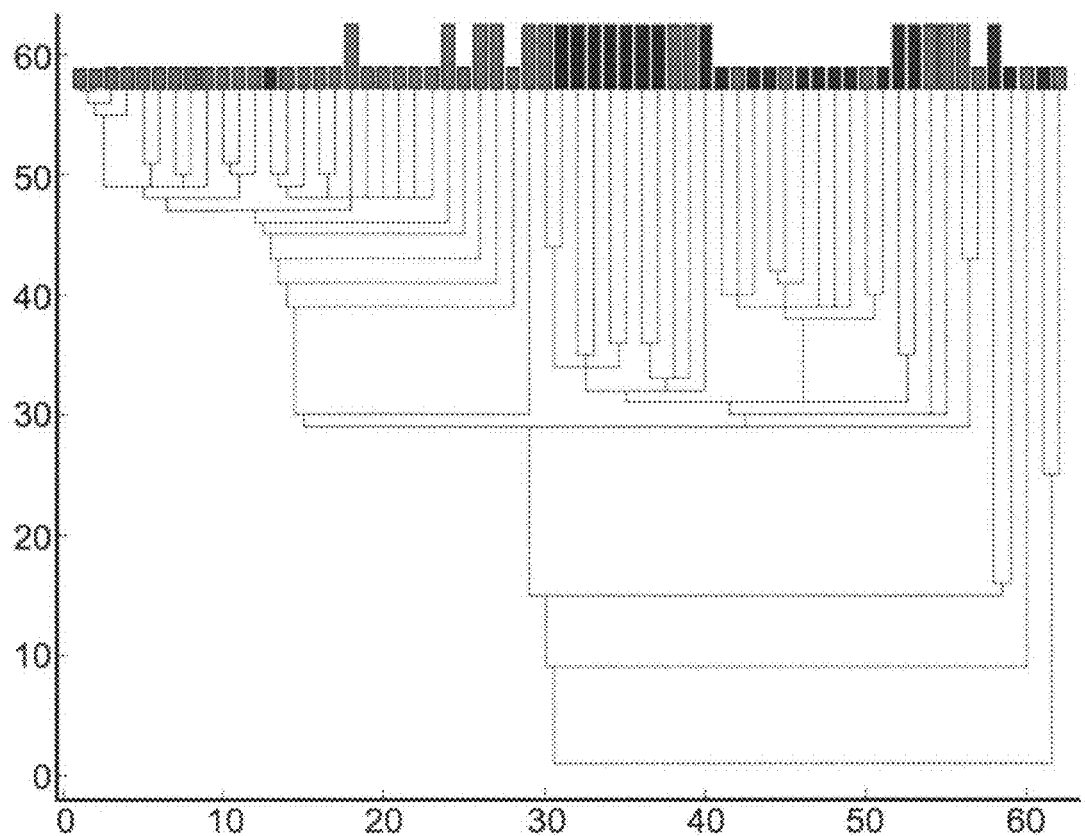
FIG. 9 shows the result of clustering colon samples, based on all genes. Fairly good separation between tumor (white) and normal (black) samples is obtained. The height of the boxes is according to experiment protocol.
Figure 14:
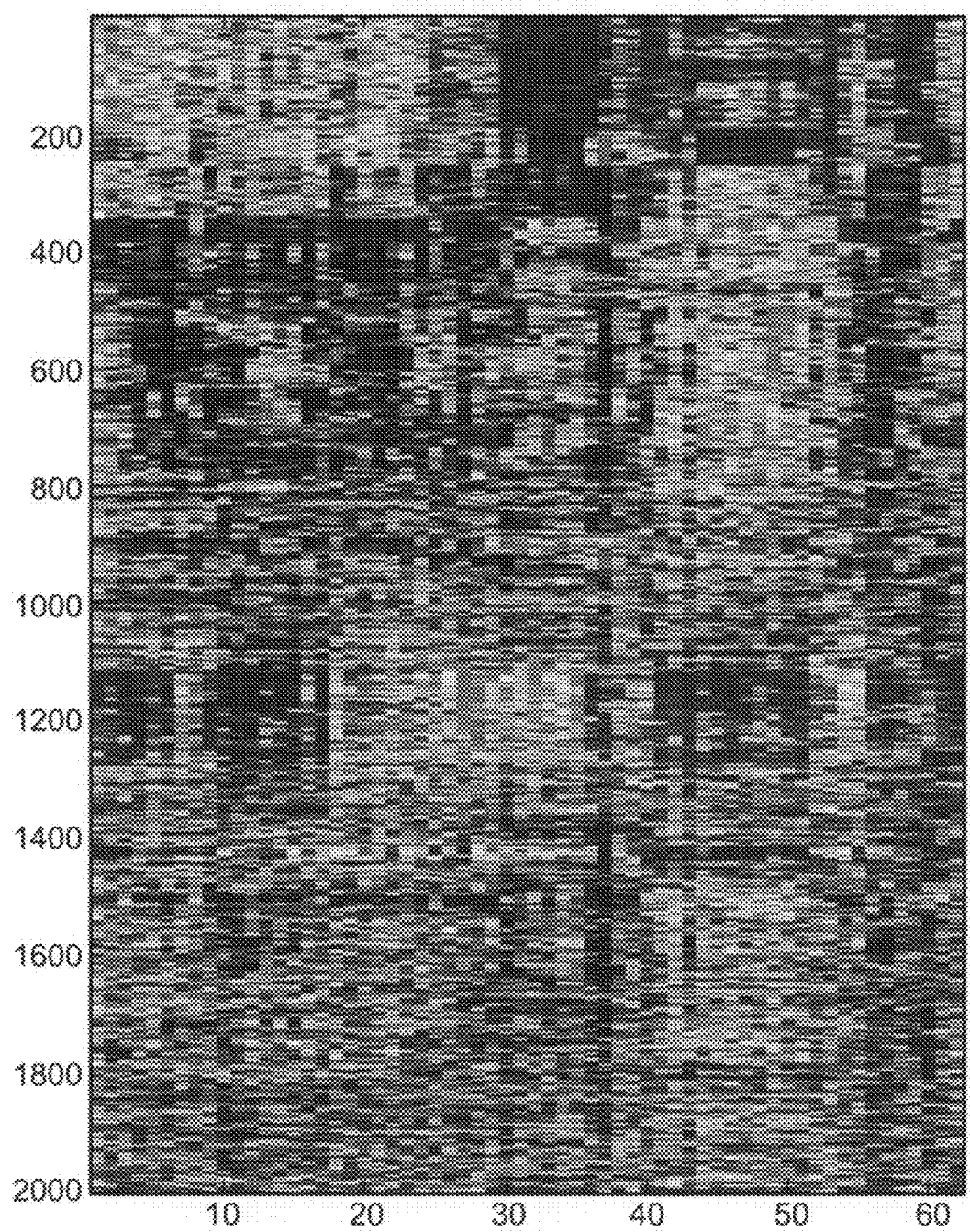
FIG. 14 shows an expression level matrix of the colon experiment. A lighter shade indicates a higher expression level.

First, the genes were clustered, using all tissues as the feature set; the clusters were ordered [3] (see dendrogram of FIG. 2) and the rows of the expression matrix were reordered accordingly. The tissues were clustered using all genes as the feature set (see FIG. 9); the columns of the expression matrix were then reordered. The result is shown in FIG. 14.

The coupled two-way clustering method of the present invention, as described in Section 1, was applied to this data set. Ninety-seven stable gene clusters (CG1-97) and seventy-six stable sample clusters (CS1-76) were obtained in two iterations. Again, results are presented which correspond to the four items of Section 1.

Figure 10:
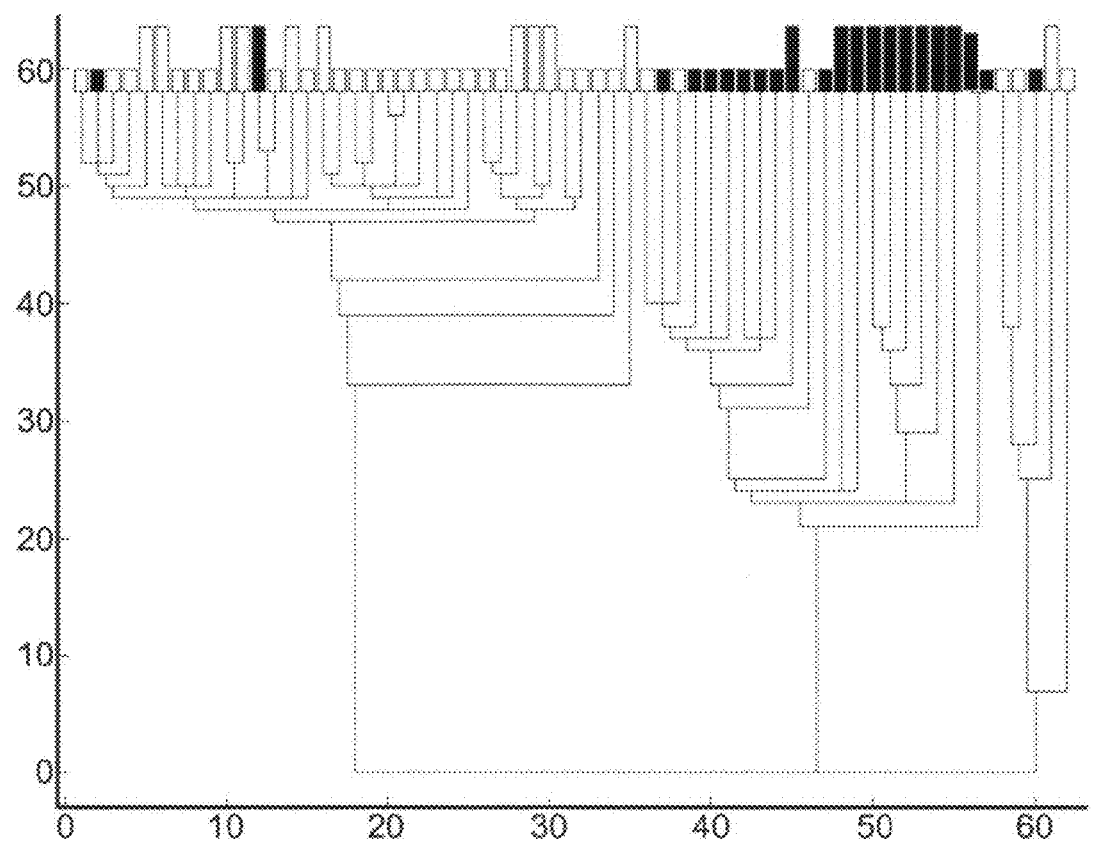
FIG. 10. shows the result of clustering colon samples, based on genes of cluster CG2. Clearer separation between tumor (white) and normal (black) samples is obtained. The height of boxes is according to the experiment protocol.

First, genes were identified that partition the samples according to a known classification. To search for gene clusters which differentiate the samples according to the known normal/tumor classification, the t-test statistic is evaluated for each gene cluster in the manner described above. Six gene clusters with relatively high t-test scores were found. Next, the data is searched for gene clusters which, when used as the features that characterize the samples, give rise to stable normal/tumor clusters (see FIG. 10). Four gene clusters (CG1-4) can be used this way to partition the samples into clusters that contain predominantly normal/tumor tissues (as for the previous data, purity and efficiency above 0.75 were required). Two of these four clusters also have high t-test scores.

Figure 11:
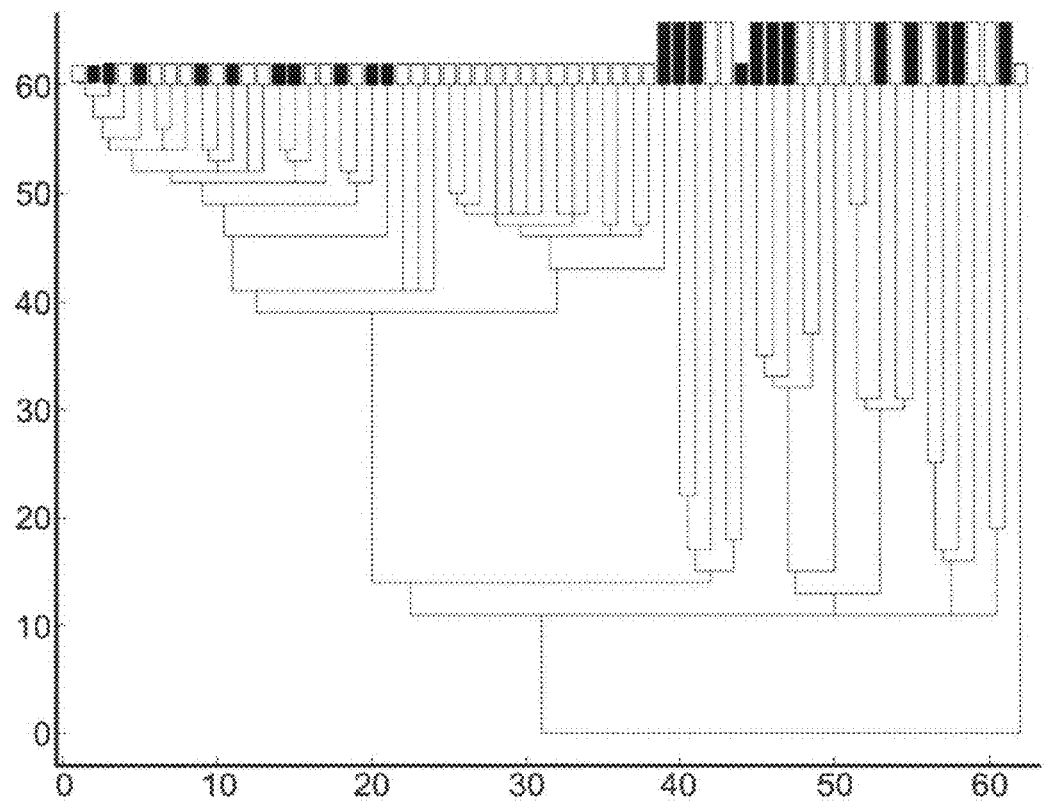
FIG. 11 shows the result of clustering colon samples, based on genes of cluster CG5. Another separation of the samples is obtained using this gene cluster. This separation is consistent with the two experiment protocols, A (short) and B (tall). Colors are according to tumor (white) vs normal (black).

These data can also optionally be further analyzed in order to discover new partitions. The stable sample clusters were further analyzed, searching for unknown partitions of the data. Five clusters of genes (CG2, CG4-7) that generate very stable clusters of samples were found. Two of the five clusters are able to differentiate tumor and normal tissues. Another two clusters are less interesting since they gave rise to stable clusters that contained most of the samples. The gene cluster CG5 gave rise to a clear partition of the samples into two clusters, one containing thirty-nine samples and the second containing the remaining twenty-three samples (see FIG. 11). According to an examination of the experimental protocol from which the original data were obtained, this separation coincides almost precisely with a change of the experimental protocol which was used: the first 22 RNA samples (eleven normal and eleven tumor) were extracted using a poly-A detector ('protocol-A'), and the other forty samples (eleven normal and twenty-nine tumor) were prepared by extracting all RNA from the cells ('protocol-B'). Thirty-eight out of the thirty-nine samples in the large cluster were taken using protocol-B. No common features were found among the twenty-nine genes of the cluster CG5 that gave rise to the separation according to the two protocols.

Figure 12:
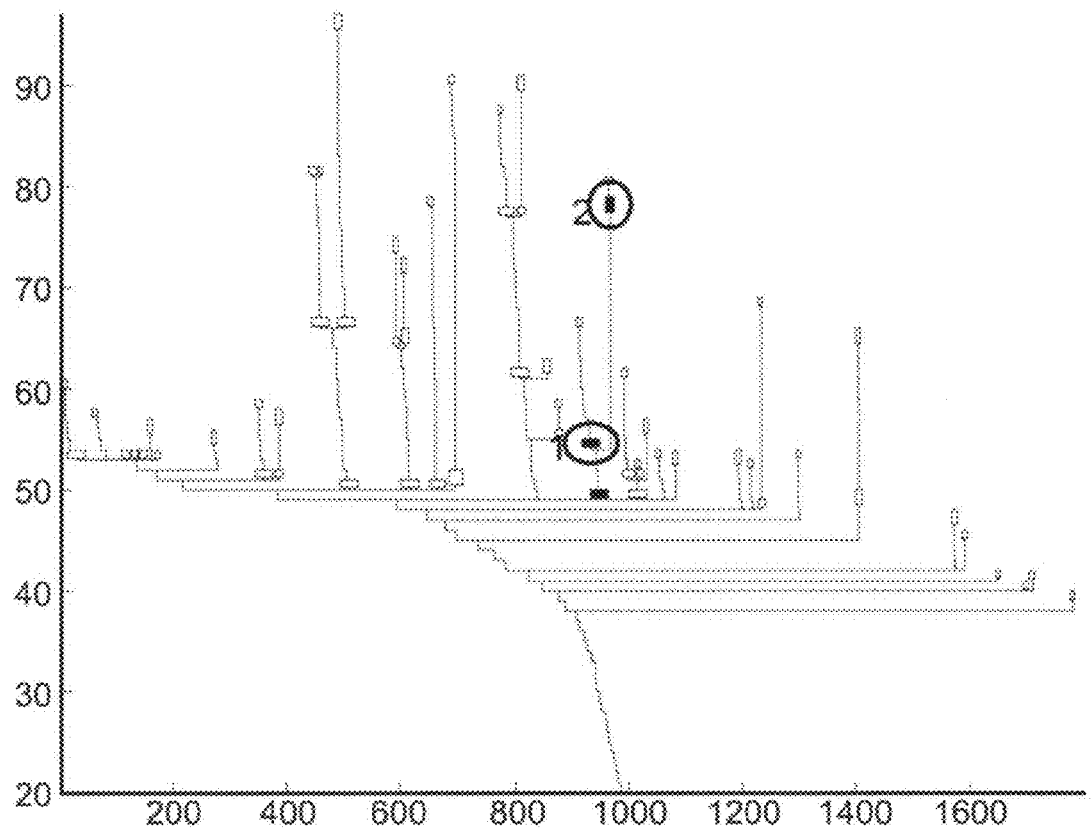
FIG. 12 shows a dendrogram of genes in colon experiment, based only on tumor samples. The marked clusters appear here close to each other and share a common 'parent' in the graph, hence the two are relatively correlated.

As in the case of the leukemia data which were previously described, here again most gene clusters form irrespectively of the samples that are used as features. However, five special groups of genes (CG8-11) were found. When all the samples were used as the feature set to cluster the genes, none of these five groups formed a cluster; similarly, when only the normal samples were used, these genes were relatively uncorrelated, i.e. spread across the dendrogram of genes. On the other hand, when the tumor samples were used as the feature set, each of these five groups formed a clear, stable cluster. The genes of each of these five clusters were used as the object set and clustered, using the tumor samples as the feature set. One of these five clusters, (CG9), was found to disintegrate, at a higher resolution, into two sub-clusters (see FIG. 12).

Figure 13:
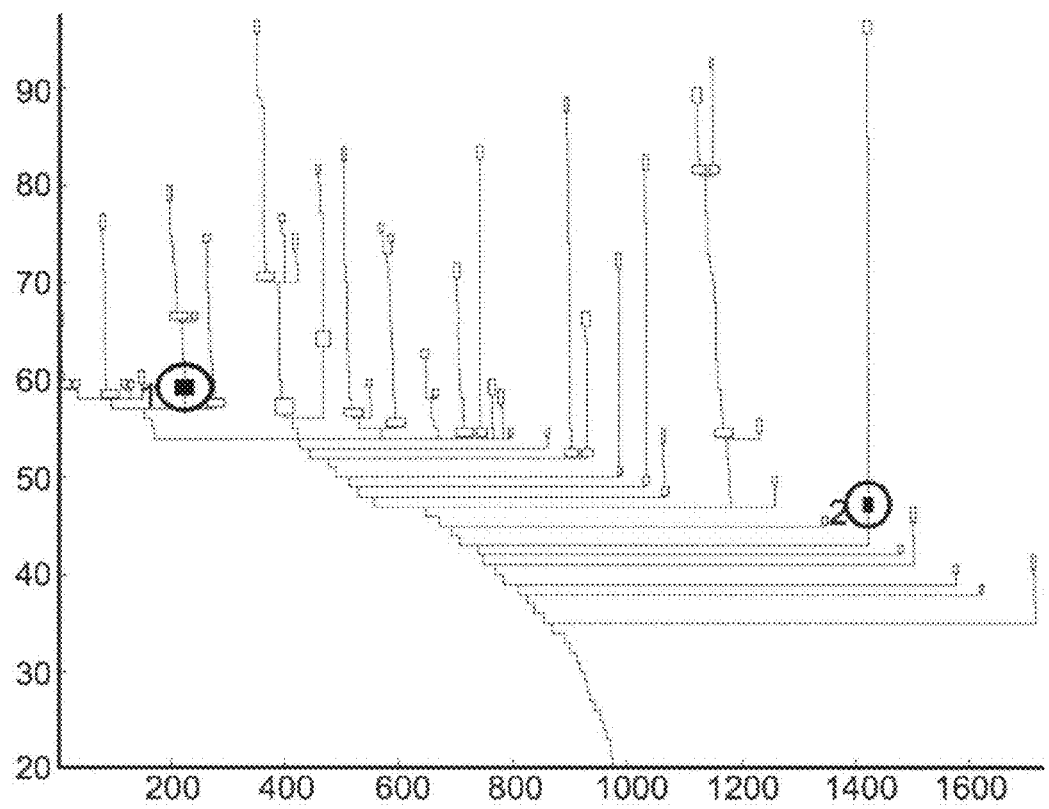
FIG. 13 shows a dendrogram of genes in colon experiment, based on all samples. The marked clusters are those which are marked in FIG. 12, except that here the two are not correlated.

Another one of these sub-clusters, (CG12), consists of fifty-one genes, all of which are related to cell growth (ribosomal proteins and elongation factors). The other sub-cluster, (CG13), contains seventeen genes, many of which are related to intestinal epithelial cells (e.g. mucin, cathespin proteases). Interestingly, when clustering the genes on the basis of the normal samples, both (CG12 and CG13) appear as two distinct clusters, but while these clusters are "daughters" of the single cluster (CG9) over the tumor samples, they are not correlated over the normal samples and their positions in the dendrogram of FIG. 13 are quite far from each other.

The high correlation between growth genes and epithelial genes, observed in the tumor tissue, suggests that it is the epithelial cells that are rapidly growing. In the normal samples there is smaller correlation, indicating that the expression of growth genes is not especially high in the normal epithelial cells. These results are consistent with the epithelial origin of colon tumor.

Two other groups of genes formed clusters only over the tumor cells. One (CG11, containing thirty-four genes) is related to the immune system (HLA genes and immunoglobulin receptors). The second (CG10, containing sixty-two genes) seems to be a concatenation of genes related to epithelial cells (endothelial growth factor and retinoic acid), and of muscle and nerve related genes. No common function for the genes in the fourth cluster (CG8) was found.

Clustering the genes on the basis of their expression over only the normal samples revealed three gene clusters (CG14-16) which did not form when either the entire set of samples or the tumor tissues were used. Again, a clear common function for these genes was not found. Each cluster contains genes that apparently participate in one or more processes which occur in normal cells, but is suppressed or absent in tumor tissues.

Section 4. Summary and Discussion

The preceding sections describe a new method for analysis of large amounts of data, such as gene microarray data. The main concept of the method of the present invention is to locate features of interest within such large sets of data, as for example small subsets of the massive expression patterns obtained from thousands of genes for a large number of samples. A cellular process of interest may involve a relatively small subset of the genes in the data set, and the process may occur only in a small number of samples. Hence when the full data set is analyzed, the "signal" of this process may be completely overwhelmed by the "noise" generated by the vast majority of unrelated data.

The specific examples illustrated in the preceding sections concerned the determination of a relatively small group of genes from a rather large experimental set, which can be used as the features for clustering a subset of the samples. Alternatively, a subset of the samples that can be used in a similar way to identify genes with correlated expression levels can also optionally be identified, as described above. Identifying pairs of subsets of those genes and samples which produce significant stable clusters is a computationally complex task. The coupled two-way clustering method of the present invention provides an efficient mechanism for producing such subgroups.

The basic coupled two-way clustering method of the present invention is simple. For example, with regard to the gene microarray data described above, initially the cluster structure of the full data set is found, both in gene and in sample space. The resulting clusters are then used again, either as new sets of objects to be clustered, or as features, to be used to cluster some limited set of objects. The method of the present invention then provides a broad list of stable gene and sample clusters, together with various connections among them. For example, for every cluster of samples $v^s$, the features (i.e. the gene clusters) that were used to generate each cluster are known. Also, the set of samples on which the clustering was performed is known. This information can be used to perform the most important tasks in microarray data analysis, such as identification of cellular processes and the conditions for their activation; establishing connection between gene groups and biological processes; and finding partitions of known classes of samples into sub-groups.

The coupled two-way clustering method of the present invention has been demonstrated to be computationally feasible for the cases which were studied. One of the reasons is that the stable clusters generated by the procedure become small with increasing iterations. Therefore their clustering analysis gets faster, and the method typically stops after only a few iterations. The method of the present invention is applicable with any reasonable, suitable choice of clustering algorithm, as long as the selected algorithm is capable of identifying stable clusters. The examples of analyses which were described above concerned one exemplary but preferred clustering algorithm, which is super-paramagnetic clustering algorithm (SPC). This algorithm is especially suitable for gene microarray data analysis due to its robustness against noise which is inherent in such experiments.

The power of the coupled two-way clustering method according to the present invention was demonstrated on data obtained in two gene microarray experiments. In the first experiment the gene expression profile in bone marrow and peripheral blood cells of seventy-two leukemia patients was measured using gene microarray technology. The main results for this data analysis can be summarized as follows. First, the connection between T-Cell related genes and the sub-classification of the ALL samples, into T-ALL and B-ALL, was revealed in an unsupervised fashion. Hence coupled two-way clustering can be used to identify genes whose expression profiles are different for different kinds of cancer. Second, a stable partition of the AML patients into two groups was also found. The first group contained those patients who were treated (with known results), and the second group contained all other patients. This partition was revealed by a cluster of cell growth related genes.

The second experiment used gene microarray technology to probe the gene expression profile of forty colon tumor samples and twenty-two normal colon tissues. Partition of the samples of this experiment into clusters of tumor and normal tissues is an easy task [16]. The method of the present invention also detects a different, less obvious stable partition of the samples into two clusters. To find this partition, a subset of the genes was used. The new partition turned out to reflect the existence of two different experimental protocols which were used to generate the data. Without wishing to be limited to a single hypothesis, it may be deduced that the genes which gave rise to this partition of the samples are those genes which were sensitive to the change of protocol.

Another result, that was obtained in an unsupervised manner using the method of the present invention, is the connection between epithelial cells and the growth of cancer. When the expression profiles were considered over only the tumor tissues, a cluster of cell growth genes was found to be highly correlated with epithelial genes. This correlation was absent when the normal tissues were used.

These novel features, discovered in data sets which were previously investigated by conventional clustering analysis, demonstrate the strength of the coupled two-way clustering method of the present invention. The coupled two-way clustering method was found to be especially useful for gene microarray data analysis, but it may be a useful tool for investigating other kinds of data as well.

For example, the method of the present invention is also optionally used to classify documents. These documents may be individually characterized according to the number of times each of a plurality of keywords appears in the document. However, simply examining the overall pattern of keyword frequency in the documents may obscure interesting partitions, or associations within the group of documents which may only characterize a subgroup of the documents. Therefore, according to the method of the present invention, the keywords themselves are optionally first examined for possible partitions and/or associations within this group of keywords. Optionally and preferably, such partitions and/or associations are identified by means of a clustering algorithm. Next, a particular subgroup of keywords is then selected from the entire group of keywords. This subgroup of keywords could optionally be associated according to the concept of "coffee" for example, such that all of the keywords in this subgroup would therefore all be related to this concept.

This particular selected subgroup of keywords, related to the concept of "coffee" for the purposes of this example, would then be used to partition the entire group of documents, in order to locate a subgroup of documents which are also related to the concept of "coffee". The process of partitioning the group of documents could also optionally and preferably be performed with a clustering algorithm, which in this example would use the metric of the number of times that each one of the keywords, that belong to the selected subgroup of keywords appeared in each document. Thus, the method of the present invention could optionally and preferably be used to partition documents into subgroups, by using a subgroup of keywords, or any other selected subgroup of characteristics.

In addition, other examples for use with the method of the present invention include, but are not limited to, financial data analysis and marketing analysis. Financial data analysis could optionally be performed with the method of the present invention by substituting stocks in some index, such as the Dow Jones, for the samples in the previous example with regard to genetics. The prices of these stocks at different times and/or the volume of trade and/or volatility of these stocks would then be used to substitute for the genes in the previous example for genetics. For marketing analysis, a list of potential customers for a particular company and/or product or service could optionally substitute for the samples in the previous genetic example. Some type of parameter or factor which characterizes these customers would then optionally substitute for the genes as in the previous genetic example. Examples of such a parameter or factor include, but are not limited to, the income of the customers, their previous record of purchases, and/or the record of browsing through the Internet.

Appendix A

This Appendix contains a simple example with artificial data, which illustrates some of the problems in the art which are solved by the method of the present invention. The data which were generated models the following situation. Two independent biological processes, $p_1$ and $p_2$, involve two different subsets of genes, $G_1$ and $G_2$ respectively. The number of genes in $G_1$ is much larger than the number of genes in $G_2$. Both processes have two phases: an active phase in which the corresponding genes are highly expressed, and an inactive phase in which the expression of these genes is suppressed. Every cell must be (simultaneously) in one of the phases of each process. Denote by $p_3$ a third process, one that influences only those cells which are in the active phase of the $p_1$ process. The process $p_3$ involves a third set of genes, $G_3$, which can be either activated or suppressed. The variation in the expression levels of genes which are unaffected by either process is due to noise. This situation is summarized in Table 1.

| Process | Genes | Samples in active phase | Samples in inactive phase | Remarks |
|---|---|---|---|---|
| $p_1$ | $G_1$(1-20) | 1-5 | 6-10 | |
| $p_2$ | $G_2$(21-25) | 1, 2, 8-10 | 3-7 | |
| $p_3$ | $G_3$(26-30) | 3-5 | 1, 2 | $p_3$ acts only in cells in active phase of $p_1$. |
| | $G_4$(31-130) | | | Genes that take no part in either process. |

Figure 15:
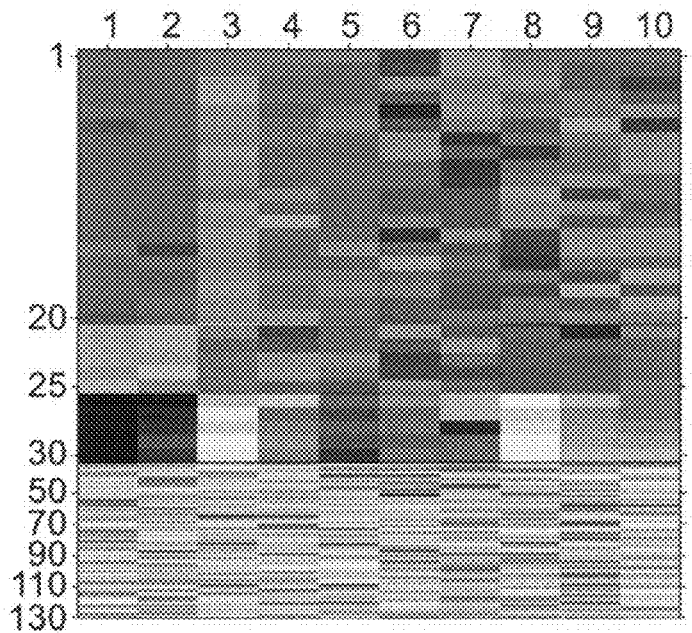
FIG. 15 shows an expression level matrix for the motivation example. A lighter shade indicates a higher expression level. See text for details.

FIG. 15 shows an expression level matrix $A_{ij}$ for the situation just described, with $|G_1|=20$, $|G_2|=|G_3|=5$ and $|G_4|=100$. Samples 1 through 5 are in the active phase of the process $p_1$; the high expression levels of the $G_1$ genes in these samples are represented by lighter shades of gray. The same group of genes are suppressed in samples 6-10 (dark shades of gray). Samples 1, 2 and 8 through 10 are in the active phase of process $p_2$. Only samples 1 through 5 can be affected by $p_3$: the first two are in the inactive phase of this process. Note that a large majority of the genes, $G_4$, do not participate in either process. When the samples are clustered using the expression levels of all the genes, the group $G_4$ introduces an effective and realistic amount of noise.

The only classification of the samples which rises above this noise is that into the two different phases of $p_1$. Partition of the samples according to their participation in the "weak" processes $p_2$ and $p_3$ is completely obscured. On the other hand, clustering the genes (on the basis of data from all samples) produces three clear clusters, containing $G_1$, $G_2$ and $G_3$ respectively, with the genes of $G_4$ constituting a dilute background.

$$d_{ik} = \left[ \sum_{j=1}^{130} (A_{i,j} - A_{k,j})^2 \right]^{1/2}$$

Figure 15A:
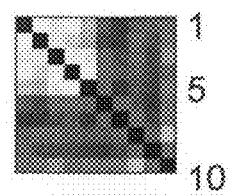
Figure 15B:
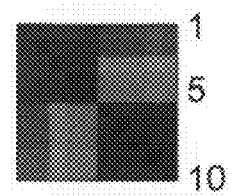
Figure 15C:
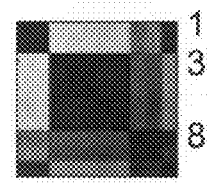

The manner in which the samples are partitioned can be seen clearly by inspecting the matrix of distances between them, calculated over all the genes, shown in FIG. 15(a). Samples 1-5 appear to be at relatively small distances from each other, whereas the other five form a more dilute "background". This distance matrix is to be compared with those matrices obtained by using only genes from $G_1$ and from $G_2$ (FIGS. 15(b) and (c), respectively). In the first matrix, two well separated dense clusters of samples 1-5 and 6-10 are seen, whereas the second matrix partitions the samples according to the process $p_2$; note that samples 1, 2 are at a small distance from each other and from samples 8-10, but far from the group of samples 3-7 (which are close to each other).

Figure 15D:
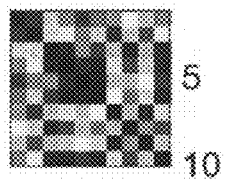
Figure 15E:
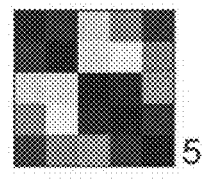

Only the genes of $G_3$ are considered, and all samples are clustered. Samples 1, 2 may be anticipated to be located in one cluster and 3-5 in another cluster; in fact, the result is a single cluster, which includes all genes. This is caused by the fact that samples 6-10, which are not affected by $p_3$, link the samples of the two expected groups (see FIG. 15(d)). If, however, only the samples 1-5 are clustered, the corresponding upper left corner of FIG. 15(d) provides a clear separation to the two expected groups of samples.

This example demonstrates the need for the method according to the present invention. The gene clusters $G_1$ are identified first and are used to partition the samples: this partition can then be used further, to reveal the inner structure of a cluster.

The problems presented in this illustrative but artificial example occur in real data as well. In real gene expression data, a group of genes which participate in a particular biological process can be expected to exhibit correlated expression patterns over the samples and to form a cluster. When only the members of this cluster are used to represent the different samples, partition of the samples to those samples in which this process does occur, from those samples in which it does not occur, should become easier. Furthermore, when this cluster of samples is identified, the problem of identifying its sub-structure becomes easier.

In addition, as previously described, clustering analysis which is performed by using select subsets of real data actually reveals important features which were hidden when the full data set was used.

While the invention has been described with respect to a limited number of embodiments, it will be appreciated that many variations, modifications and other applications of the invention may be made.

Appendix B—Lists of Stable Clusters

B.1 LG1
 1. AF006084 at Arp2/3 protein complex subunit p41-Arc (ARC41) mRNA
 2. D16217 at CAST Calpastatin
 3. D29963 at Platelet-endothelial tetraspan antigen 3 mRNA
 4. D49400 at Fetus brain mRNA for vacuolar ATPase 5. D78361 at "Ornithine decarboxylase antizyme, ORF 1 and ORF 2"
6. HG2059-HT2114 at "Arrestin, Beta 2"
7. HG2279-HT2375 at Triosephosphate Isomerase
8. HG2788-HT2896 at Calcyclin
9. J02923 at LCP1 Lymphocyte cytosolic protein 1 (L-plastin)
10. J04162 at "FCGR3 Fc fragment of IgG, low affinity IIIa, receptor for (CD16)"
11. J04173 at PGAM1 Phosphoglycerate mutase 1 (brain)
12. J05272 at IMPDH1 IMP (inosine monophosphate) dehydrogenase 1
13. K01396 at "PI Protease inhibitor 1 (anti-elastase), alpha-1-antitrypsin"
14. L12168 at ADENYLYL CYCLASE-ASSOCIATED PROTEIN 1
15. L19437 at TALDO Transaldolase
16. L42373 at Protein phosphatase 2A B56-alpha mRNA
17. M11147 at "FTL Ferritin, light polypeptide"
18. M19722 at FGR Gardner-Rasheed feline sarcoma viral (v-fgr) oncogene homolog
19. M23197 at CD33 CD33 antigen (differentiation antigen)
20. M23254 at "CAPN2 Calpain, large polypeptide L2"
21. M32315 at TNFR2 Tumor necrosis factor receptor 2 (75 kD)
22. M55067 at NCF1 47 kD autosomal chronic granulomatous disease protein
23. M62783 at "NAGA N-acetylgalactosaminidase, alpha-"
24. M63138 at CTSD Cathepsin D (lysosomal aspartyl protease)
25. M63167 at AKT1 V-akt murine thymoma viral oncogene homolog 1
26. M91029 cds2 at AMP deaminase (AMPD2) mRNA
27. U02570 at "CDC42 GTPase-activating protein mRNA, partial cds"
28. U06681 at Clone CCA12 mRNA containing CCA trinucleotide repeat
29. U10868 at ALDH7 Aldehyde dehydrogenase 7
30. U40282 at Integrin-linked kinase (ILK) mRNA
31. U44772 at Palmitoyl protein thioesterase mRNA
32. U46692 rna1 at Cystatin B gene
33. U50136 rna1 at Leukotriene C4 synthase (LTC4S) gene
34. U50523 at "BRCA2 region, mRNA sequence CG037"
35. U51336 at "Inositol 1,3,4-trisphosphate 5/6-kinase mRNA"
36. U59878 at "Low-Mr GTP-binding protein (RAB32) mRNA, partial cds"
37. U89336 cds1 at "Unknown gene extracted from Human HLA class III region containing NOTCH4 gene, partial sequence, homeobox PBX2 (HPBX) gene, receptor for advanced glycosylation end products (RAGE) gene, and 6 unidentified cds, complete sequence"
38. X16663 at HEMATOPOIETIC LINEAGE CELL SPECIFIC PROTEIN
39. X56494 at "PKM2 Pyruvate kinase, muscle"
40. X62320 at GRN Granulin
41. X67698 at Tissue specific mRNA
42. X69550 at Rho GDP-dissociation Inhibitor 1
43. X76538 at "MPV17 MpV17 transgene, murine homolog, glomerulosclerosis"
44. X98411 at GB DEF=Myosin-IE
45. Z32765 at GB DEF=CD36 gene exon 15
46. Z36531 at FGL1 Fibrinogen-like 1
47. U34587 at CRHR2 Corticotropin releasing hormone receptor 2
48. U53204 at Plectin (PLEC1) mRNA
49. D43682 s at Very-long-chain acyl-CoA dehydrogenase (VLCAD)
50. X55448 cds1 s at G6PD gene (glucose-6-phosphate dehydrogenase) extracted from H. sapiens G6PD gene for glucose-6-phosphate dehydrogenase
51. HG2090-HT2152 s at "External Membrane Protein, 130 Kda (Gb:Z22971)"
52. HG4264-HT4534 s at Guanine Nucleotide-Binding Protein Rab5c-Like Protein
53. U01691 s at "Annexin V (ANX5) gene, 5'-untranslated region"
54. M32304 s at TIMP2 Tissue inhibitor of metalloproteinase 2
55. L35249 s at "ATP6B2 ATPase, H+ transporting, lysosomal (vacuolar proton pump), beta polypeptide, 56/58 kD, isoform 2"
56. U45448 s at P2×1 receptor mRNA
57. J03801 f at LYZ Lysozyme
58. M19045 f at LYZ Lysozyme
59. X14008 rna1 f at Lysozyme gene (EC 3.2.1.17)
60. X16546 at RNS2 Ribonuclease 2 (eosinophil-derived neurotoxin; EDN)

B.2 LG2
1. D00726 at FECH Ferrochelatase (protoporphyria)
2. D26308 at NADPH-flavin reductase
3. D87451 at KIAA0262 gene
4. HG4018-HT4288 at Opioid-Binding Cell Adhesion Molecule
5. K03195 at (HepG2) glucose transporter gene mRNA
6. L15702 at "BF B-factor, properdin"
7. L37033 at FK-506 binding protein homologue (FKBP38) mRNA
8. M10612 at APOC2 Apolipoprotein C-II
9. M14016 at UROD Uroporphyrinogen decarboxylase
10. M20902 at APOC1 Apolipoprotein CI
11. M24470 at G6PD Glucose-6-phosphate dehydrogenase
12. M31994 at "ALDH1 Aldehyde dehydrogenase 1, soluble"
13. M55040 at ACHE Acetylcholinesterase (YT blood group)
14. M75126 at HK1 Hexokinase 1
15. U05659 at HSD17B3 Hydroxysteroid (17-beta) dehydrogenase 3
16. U40391 rna1 at Serotonin N-acetyltransferase gene
17. X64364 at BSG Basigin
18. Y07847 at RRP22 protein
19. Z23115 at APOPTOSIS REGULATOR BCL-X
20. D16105 at LTK Leukocyte tyrosine kinase
21. U36341 rna1 at "SLC6A8 gene (creatine transporter) extracted from Human Xq28 cosmid, creatine transporter (SLC6A8) gene, and CDM gene, partial cds"
22. U41518 at "AQP1 Aquaporin 1 (channel-forming integral protein, 28 kD)"
23. HG4535-HT4940 s at Dematin
24. M60974 s at DDIT1 DNA-damage-inducible transcript 1
25. L32831 s at PROBABLE G PROTEIN-COUPLED RECEPTOR GPR3
26. J02982 f at GYPB Glycophorin B
27. X83863 at PTGER3 Prostaglandin E receptor 3 (subtype EP3) alternative products B.3 LG3
1. D86519 at Truncated pancreatic polypeptide receptor PP2 mRNA
2. HG1649-HT1652 at Elastase 1
3. HG3255-HT3432 at Gamma-Aminobutyric Acid (Gaba) A Receptor Beta 2 Subunit
4. HG4114-HT4384 at Olfactory Receptor Or17-209
5. HG4332-HT4602 at Zinc Finger Protein Znfpt1
6. J00073 at "Alpha-cardiac actin gene, 5' flank and"
7. J03133 at SP1 Sp1 transcription factor
8. L21893 at SLC10A1 Na/taurocholate cotransporting polypeptide
9. L48728 cds1 at TCRBV10S1 gene extracted from *Homo sapiens* T cell receptor beta (TCRBV10S1) gene
10. L76380 at (clone HSNME29) CGRP type 1 receptor mRNA
11. M31525 at "HLA-DNA Major histocompatibility complex, class II, DN alpha"
12. M87284 at 69/71 KD
13. S77576 at "GB DEF=ERV9 reverse transcriptase homolog {clone RT18} [human, multiple sclerosis, brain plaques, mRNA Partial, 84 nt]"
14. U19345 at AR1 protein (AR) mRNA
15. U37251 at ZNF177 KRAB zinc finger protein {alternative products}
16. U39905 at "SLC18A1 Solute carrier family 18 (vesicularmonoamine), member 1"
17. U48263 at Pre-pro-orphanin FQ (OFQ) mRNA
18. U52112 rna1 at "L1CAM gene (neural cell adhesion molecule L1) extracted from Human Xq28 genomic DNA in the region of the L1CAM locus containing the genes for neural cell adhesion molecule L1 (L1CAM), arginine-vasopressin receptor (AVPR2), C1 p115 (C1), ARD1 N-acetyltransferase related protein (TE2), renin-binding protein (RbP), host cell factor 1 (HCF1), and interleukin-1 receptor-associated kinase (IRAK) genes, and Xq28lu2 gene"
19. U56244 at HIG-1 mRNA
20. U56814 at DNaseI-Like III protein (DNAS1L3) mRNA
21. U62739 at Branched-chain amino acid aminotransferase (ECA40) mRNA
22. U66879 at Bcl-2 binding component 6 (bbc6) mRNA
23. U67674 at "SLC15A2 Solute carrier family 15 (H+/peptide transporter), member 2"
24. U72508 at B7 mRNA
25. U89336 cds3 at "RAGE gene (receptor for advanced glycosylation end products) extracted from Human HLA class III region containing NOTCH4 gene, partial sequence, homeobox PBX2 (HPBX) gene, receptor for advanced glycosylation end products (RAGE) gene, and 6 unidentified cds, complete sequence"
26. X53331 at MGP Matrix protein gla
27. X57303 at ERR Ecotropic retroviral receptor
28. X72177 rna1 at "C6 gene, exon 1"
29. X73113 at Fast MyBP-C
30. X76770 at PAP mRNA
31. X79981 at "CDH5 Cadherin 5, VE-cadherin (vascular epithelium)"
32. Y08976 at GB DEF=FEV protein
33. X14766 at "GABRA1 Gamma-aminobutyric acid (GABA) A receptor, alpha 1"
34. X80763 s at HTR2C 5-hydroxytryptamine (serotonin) receptor 2C
35. L05187 at GB DEF=Small proline-rich protein 1 (SPRR1A) gene
36. J00212 f at "IFNA21 Interferon, alpha 21"

B.4 LG4
1. HG3364-HT3541 at Ribosomal Protein L37
2. L06499 at RPL37A Ribosomal protein L37a
3. L06505 at RPL12 Ribosomal protein L12
4. M13934 cds2 at RPS14 gene (ribosomal protein S14) extracted from Human ribosomal protein S14 gene
5. M17885 at "RPLP0 Ribosomal protein, large, P0"
6. M17886 at "RPLP1 Ribosomal protein, large, P1"
7. M24194 at Alpha-tubulin mRNA
8. M60854 at RPS16 Ribosomal protein S16
9. U14969 at Ribosomal protein L28 mRNA
10. U14973 at 40S RIBOSOMAL PROTEIN S29
11. X03342 at RPL32 Ribosomal protein L32
12. X17206 at PTB Ribosomal protein L26
13. X55715 at RPS3 Ribosomal protein S3
14. X64707 at 60S RIBOSOMAL PROTEIN L13
15. X69150 at GB DEF=Ribosomal protein S18
16. X80822 at 60S RIBOSOMAL PROTEIN L18A
17. Z12962 at EEF1A1 Translation elongation factor 1-alpha-1
18. Z70759 at GB DEF=Mitochondrial 16S rRNA gene (partial)
19. AB002533 at "RPLP2 Hemoglobin, beta"
20. HG1428-HT1428 s at "Globin, Beta"
21. M10277 s at "ACTB Actin, beta"
22. J04617 s at EEF1A1 Translation elongation factor 1-alpha-1
23. M26708 s at PTMA Prothymosin alpha
24. U06155 s at GB DEF=Chromosome 1q subtelomeric sequence D1S553
25. Z49148 s at Enhancer of rudimentary homolog mRNA
26. S82297 at BETA-2-MICROGLOBULIN PRECURSOR
27. M36072 at RPL7A Ribosomal protein L7a
28. X01677 f at GAPD Glyceraldehyde-3-phosphate dehydrogenase B.5 LG5
1. D26599 at Proteasome subunit HsC7-I
2. D26600 at PROTEASOME BETA CHAIN PRECURSOR
3. D38047 at 26S PROTEASOME REGULATORY SUBUNIT P31
4. D38076 at RANBP1 RAN binding protein 1
5. HG4073-HT4343 at Cytosolic Acetoacetyl-Coenzyme A Thiolase
6. L05148 at Protein tyrosine kinase related mRNA sequence
7. L25851 at INTEGRIN ALPHA-E PRECURSOR
8. M13792 at ADA Adenosine deaminase
9. M34079 at PROBABLE 26S PROTEASE SUBUNIT TBP-1
10. M59807 at NATURAL KILLER CELLS PROTEIN 4 PRECURSOR
11. M86707 at GLYCYLPEPTIDE N-TETRADECANOYLTRANSFERASE
12. M86737 at SSRP1 High mobility group box
13. U14603 at Protein tyrosine phosphatase PTPCAAX2 (hPTPCAAX2) mRNA
14. U18009 at Chromosome 17q21 mRNA clone LF113
15. U23143 at "Mitochondrial serine hydroxymethyltransferase gene, nuclear encoded mitochondrion protein"
16. X03934 at GB DEF=T-cell antigen receptor gene T3-delta
17. X04391 at CD5 CD5 antigen (p56-62)
18. X69433 at "IDH2 Isocitrate dehydrogenase 2 (NADP+), mitochondrial"

19. Y10936 at GB DEF=Hypothetical protein downstream of DMPK and DMAHP
20. Z35227 at TTF mRNA for small G protein
21. Y00097 s at ANX6 Annexin VI (p68)
22. D00749 s at T-CELL ANTIGEN CD7 PRECURSOR
23. M23323 s at T-CELL SURFACE GLYCOPROTEIN CD3 EPSILON CHAIN PRECURSOR
24. Z47055 s at "GB DEF=Partial cDNA sequence, farnesyl pyrophosphate synthetase like-4"
25. X73358 s at HAES-1 mRNA
26. U23852 s at GB DEF=T-lymphocyte specific protein tyrosine kinase p56lck (lck) abberant mRNA
27. U49835 s at CHIT1 Chitinase 1
28. Z25521 s at "GB DEF=Integrin associated protein mRNA,"
29. U04241 at Homolog of *Drosophila* enhancer of split m9/m10 mRNA B.6 LG6
1. D45248 at Proteasome activator hPA28 subunit beta
2. D49410 at "IL3RA Interleukin 3 receptor, alpha (low affinity)"
3. X00274 at "HLA CLASS II HISTOCOMPATIBILITY ANTIGEN, DR ALPHA CHAIN PRECURSOR"
4. X03100 cds2 at HLA-SB alpha gene (class II antigen) extracted from Human HLA-SB(DP) alpha gene
5. X14046 at CD37 CD37 antigen
6. X66401 cds1 at "LMP2 gene extracted from *H. sapiens* genes TAP1, TAP2, LMP2, LMP7 and DOB"
7. X56841 at HLA-E MHC class I antigen HLA-E
8. D49824 s at GB DEF=HLA-B null allele mRNA
9. J00105 s at BETA-2-MICROGLOBULIN PRECURSOR
10. M34996 s at "MHC cell surface glycoprotein (HLA-DQA) mRNA, 3'end"
11. HG3597-HT3800 f at "Major Histocompatibility Complex, Class I (Gb:X12432)"
12. HG688-HT688 f at "Major Histocompatibility Complex, Class Ii, Dr Beta 2 (Gb:X65561)"
13. X17093 at "HLA CLASS IHISTOCOMPATIBILITY ANTIGEN, F ALPHA CHAIN PRECURSOR"
14. D32129 f at "HLA-A MHC class I protein HLA-A (HLA-A28, -B40, -Cw3)"
15. HG2915-HT3059 f at "Major Histocompatibility Complex, Class I, E (Gb:M20022)"
16. HG2917-HT3061 f at "Major Histocompatibility Complex, Class I, E (Gb:M21533)"
17. K02405 f at "HLA CLASS II HISTOCOMPATIBILITY ANTIGEN, DQ(1) BETA CHAIN PRECURSOR"
18. M33600 f at "HLA-DRB1 Major histocompatibility complex, class II, DR beta 5"
19. HG658-HT658 f at "Major Histocompatibility Complex, Class I, C (Gb:X58536)"
20. M94880 f at "HLA-A MHC class I protein HLA-A (HLA-A28, -B40, -Cw3)"
21. X03068 f at "HLA CLASS II HISTOCOMPATIBILITY ANTIGEN, DQ(W1.1) BETA CHAIN PRECURSOR"

B.7 LG7
1. AB000464 at "mRNA, clone RES4-24A, exon 1, 2, 3, 4"
2. D25248 at Randomly sequenced mRNA
3. D63485 at KIAA0151 gene
4. D78367 at K12 keratin
5. D83542 at Cadherin-15
6. HG1155-HT4822 at "Colony-Stimulating Factor 1, Macrophage, Alt. Splice 3"
7. HG2320-HT2416 at "Integrin, Beta 3 Subunit"
8. HG3355-HT3532 at Peroxisome Proliferator Activated Receptor (Gb:Z30972)
9. HG3566-HT3769 at Zinc Finger Protein (Gb:M88359)
10. HG4167-HT4437 at "Nuclear Factor 1, A Type"
11. HG4272-HT4542 at Hepatocyte Growth Factor Receptor
12. HG4533-HT4938 at "Kallistatin, Protease Inhibitor 4"
13. J02906 at CYTOCHROME P450 IIF1
14. J02943 at CBG Corticosteroid binding globulin
15. J03278 at "PDGFRB Platelet-derived growth factor receptor, beta polypeptide"
16. J03756 at SOMATOTROPIN PRECURSOR
17. K01383 at "GB DEF=Metallothionein-I-A gene, complete coding sequence"
18. L03785 at "MYL5 Myosin, light polypeptide 5, regulatory"
19. L34060 at Cadherin-8 mRNA
20. M13666 at MYB Proto-oncogene c-myb {alternative products}
21. M14158 cds4 at T-cell receptor beta-chain J1.3 gene extracted from Human T-cell receptor germline beta-chain D1.1 and J1.1 to J1.6 genes
22. M17262 at PROTHROMBIN PRECURSOR
23. M19720 rna1 at L-myc gene (L-myc protein) extracted from Human L-myc protein gene
24. M22490 at BMP4 Bone morphogenetic protein 4
25. M62486 at "C4BPA.Complement component 4-binding protein, alpha"
26. M74491 at ARF3 ADP-ribosylation factor 3
27. M83181 at GB DEF=Serotonin receptor gene
28. M92424 at "MDM2 Mouse double minute 2, human homolog of; p53-binding protein"
29. M98776 rna1 at Keratin 1 gene
30. S65583 rna1 at "SP-10=intra-acrosomal protein {alternatively spliced} [human, liver, Genomic, 2339 nt 4 segments]"
31. S73149 at "GB DEF=Insulin-like growth factor II {intron 7} [human, Genomic, 1702 nt]"
32. S77415 at "Melanocortin-4 receptor [human, Genomic, 1671 nt]"
33. S79267 at CD4 CD4 antigen (p55)
34. S82198 at Caldecrin
35. U25750 at GB DEF=Chromosome 17q21 mRNA clone 1046:1-1
36. U29700 at GB DEF=Anti-mullerian hormone type II receptor precursor gene
37. U37707 at DLG3 Homolog 3 of *Drosophila* large discs
38. U45982 at GB DEF=G protein-coupled receptor GPR-9-6 gene
39. U46023 at Xq28 mRNA
40. U50062 at "Cell death protein (RIP) mRNA, partial cds"
41. U60269 cds2 at "Putative envelope protein; orf similar to env of Type A and Type B retroviruses and to class II HERVs gene extracted from Human endogenous retrovirus HERV-K(HML6) proviral clone HML6.17 putative polymerase and envelope genes, partial cds, and 3'LTR"
42. U61263 at Acetolactate synthase homolog mRNA
43. U66578 at Purinergic receptor P2Y9 mRNA
44. U71088 at MAP kinase kinase MEK5c mRNA
45. U72512 at "GB DEF=B-cell receptor associated protein (hBAP) alternatively spliced mRNA, partial 3'UTR"
46. U72517 at "GB DEF=Alternatively spliced variant C7f (C3f) mRNA, partial 3'UTR"

47. U76010 at Putative zinc transporter ZnT-3 (ZnT-3) mRNA
48. U77827 at GB DEF=Orphan G protein-coupled receptor (CEPR) gene
49. U78793 at "GB DEF=Folate receptor alpha (hFR) mRNA, partial cds"
50. U85193 at Nuclear factor I-B2 (NFIB2) mRNA
51. U87408 at "Clone IMAGE:30008 unknown protein mRNA, partial cds"
52. U90550 at Butyrophilin (BTF2) mRNA
53. X01388 at APOC3 Apolipoprotein C-III
54. X07024 at TRANSCRIPTION INITIATION FACTOR TFIIHD 250 KD SUBUNIT
55. X13444 at T-CELL SURFACE GLYCOPROTEIN CD8 BETA.3 CHAIN PRECURSOR
56. X52479 at "PRKCA Protein kinase C, alpha"
57. X63337 at GB DEF=HB2A gene for high sulfur keratin
58. X69636 at GB DEF=mRNA sequence (15q11-13)
59. X69699 at Pax8 mRNA
60. X74614 at GB DEF=ODF2 (allele 2) gene for outer dense fiber protein
61. X80923 at GB DEF=Nov gene
62. X89960 at Mitochondrial capsule selenoprotein
63. X92521 at Clone rasi-1 matrix metalloproteinase RASI-1 mRNA
64. X97198 at "Receptor protein tyrosine phosphatase hPTP-J precursor, mRNA"
65. X98261 at "M-phase phosphoprotein, mpp5"
66. Y11897 at GB DEF=Brx gene 3'UTR
67. Y14140 at GB DEF=G protein gene encoding beta 3 subunit exon 1 and promoter
68. Z18859 rna1 at Cone transducin alpha subunit gene extracted from *H. sapiens* gene for cone transducin alpha subunit
69. Z71460 at Vacuolar-type H(+)-ATPase 115 kDa subunit
70. M24900 at V-ERBA RELATED PROTEIN EAR-1
71. X55005 rna1 at C-erbA-1 mRNA for thyroid hormone receptor alpha
72. AB002356 s at DENN mRNA
73. S50017 s at "CNP 2',3'-cyclic nucleotide 3' phosphodiesterase"
74. X14085 s at GGTB2 Glycoprotein-4-beta-galactosyltransferase 2
75. J03241 s at "TGFB3 Transforming growth factor, beta 3"
76. S40719 s at GFAP Glial fibrillary acidic protein
77. X69920 s at CALCR Calcitonin receptor
78. M55998 s at "GB DEF=Alpha-1 collagen type I gene, 3' end"
79. X65962 s at "CYP2C17 Cytochrome P450, subfamily IIC (mephenytoin 4-hydroxylase), polypeptide 17"
80. X15673 s at GB DEF=PTR2 mRNA for repetitive sequence
81. S49592 s at "Transcription factor E2F like protein [human, mRNA, 2492 nt]"
82. S72503 s at HRK1
83. S83513 s at ADCYAP1 Adenylate cyclase activating polypeptide 1 (pituitary)
84. U41068 cds2 s at "Retinoid X receptor beta (RXRbeta) gene, partial 3' transcript, and collagen alpha2(XI) (COL11A2) gene"
85. U57623 s at "FATTY ACID-BINDING PROTEIN, HEART"
86. U66828 s at Carnitine palmitoyltransferase I (CPTI) mRNA
87. Z49825 s at HEPATOCYTE NUCLEAR FACTOR 4
88. J05412 at "REG1A Regenerating islet-derived 1 alpha (pancreatic stone protein, pancreatic thread protein)"
89. L37112 at AVPR1B Arginine vasopressin receptor 1B
90. X98253 at ZNF183 gene
91. L18877 f at MELANOMA-ASSOCIATED ANTIGEN 12
92. X13930 f at CYTOCHROME P450 IIA6
93. L78833 cds4 at "Ifp35 gene extracted from Human BRCA1, Rho7 and vat1 genes, and ipf35 gene, partial cds"
94. M93143 at PLGL Plasminogen-like protein B.8 LG8
1. D00726 at FECH Ferrochelatase (protoporphyria)
2. D26308 at NADPH-flavin reductase
3. D87451 at KIAA0262 gene
4. HG4018-HT4288 at Opioid-Binding Cell Adhesion Molecule
5. K03195 at (HepG2) glucose transporter gene mRNA
6. L15702 at "BF B-factor, properdin"
7. L37033 at FK-506 binding protein homologue (FKBP38) mRNA
8. M10612 at APOC2 Apolipoprotein C-II
9. M14016 at UROD Uroporphyrinogen decarboxylase
10. M20902 at APOC1 Apolipoprotein CI
11. M24470 at G6PD Glucose-6-phosphate dehydrogenase
12. M31994 at "ALDH1 Aldehyde dehydrogenase 1, soluble"
13. M55040 at ACHE Acetylcholinesterase (YT blood group)
14. M75126 at HK1 Hexokinase 1
15. U05659 at HSD17B3 Hydroxysteroid (17-beta) dehydrogenase 3
16. U40391 rna1 at Serotonin N-acetyltransferase gene
17. X64364 at BSG Basigin
18. Y07847 at RRP22 protein
19. Z23115 at APOPTOSIS REGULATOR BCL-X
20. D16105 at LTK Leukocyte tyrosine kinase
21. U36341 rna1 at "SLC6A8 gene (creatine transporter) extracted from Human Xq28 cosmid, creatine transporter (SLC6A8) gene, and CDM gene, partial cds"
22. U41518 at "AQP1 Aquaporin 1 (channel-forming integral protein, 28 kD)"
23. HG4535-HT4940 s at Dematin
24. M60974 s at DDIT1 DNA-damage-inducible transcript 1
25. L32831 s at PROBABLE G PROTEIN-COUPLED RECEPTOR GPR3
26. J02982 f at GYPB Glycophorin B
27. X83863 at PTGER3 Prostaglandin E receptor 3 (subtype EP3) alternative products B.9 LG9
1. D00596 at TYMS Thymidylate synthase
2. D26599 at Proteasome subunit HsC7-I
3. D30758 at KIAA0050 gene
4. D38047 at 26S PROTEASOME REGULATORY SUBUNIT P31
5. HG2279-HT2375 at Triosephosphate Isomerase
6. HG2415-HT2511 at Transcription Factor E2f-2
7. HG2788-HT2896 at Calcyclin
8. HG4073-HT4343 at Cytosolic Acetoacetyl-Coenzyme A Thiolase
9. J04173 at PGAM1 Phosphoglycerate mutase 1 (brain)
10. K03515 at GPI Glucose phosphate isomerase
11. L05148 at Protein tyrosine kinase related mRNA sequence 12. L10838 at PRE-MRNA SPLICING FACTOR SRP20
13. L25851 at INTEGRIN ALPHA-E PRECURSOR
14. L26247 at RPL3 Ribosomal protein L3
15. M13792 at ADA Adenosine deaminase
16. M14676 at "FYN FYN oncogene related to SRC, FGR, YES"
17. M19722 at FGR Gardner-Rasheed feline sarcoma viral (v-fgr) oncogene homolog
18. M34079 at PROBABLE 26S PROTEASE SUBUNIT TBP-1
19. M86707 at GLYCYLPEPTIDE N-TETRADE-CANOYLTRANSFERASE
20. M97856 at NASP Nuclear autoantigenic sperm protein (histone-binding)
21. U14603 at Protein tyrosine phosphatase PTPCAAX2 (hPTPCAAX2) mRNA
22. U18009 at Chromosome 17q21 mRNA clone LF113
23. U39318 at AF-4 mRNA
24. U43083 at "GNAQ Guanine nucleotide binding protein (G protein), q polypeptide"
25. U44772 at Palmitoyl protein thioesterase mRNA
26. U59878 at "Low-Mr GTP-binding protein (RAB32) mRNA, partial cds"
27. U64444 at Ubiquitin fusion-degradation protein (UFD1L) mRNA
28. U85611 at Snk interacting protein 2-28 mRNA
29. U89896 at Casein kinase I gamma 2 mRNA
30. X03934 at GB DEF=T-cell antigen receptor gene T3-delta
31. X04391 at CD5 CD5 antigen (p56-62)
32. X13546 rna1 at Put. HMG-17 protein gene extracted from Human HMG-17 gene for non-histone chromosomal protein HMG-17
33. X56494 at "PKM2 Pyruvate kinase, muscle"
34. X69433 at "IDH2 Isocitrate dehydrogenase 2 (NADP+), mitochondrial"
35. X71428 at RNA-BINDING PROTEIN FUS/TLS
36. X71973 at GPX4 Phospholipid hydroperoxide glutathione peroxidase
37. X77584 at TXN Thioredoxin
38. X80200 at MLN62 mRNA
39. X98172 at MACH-alpha-2 protein
40. X99585 at SMT3B protein
41. Z35227 at TTF mRNA for small G protein
42. X78338 at MULTIDRUG RESISTANCE-ASSOCIATED PROTEIN 1
43. S78771 s at RING3 PROTEIN
44. Z84497 s at RING3 PROTEIN
45. V00599 s at mRNA fragment encoding beta-tubulin. (from clone D-beta-1)
46. U01691 s at "Annexin V (ANX5) gene, 5'-untranslated region"
47. U61734 s at "(clone S31i125) mRNA, 3' end of cds"
48. Y08765 s at ZFM1 protein alternatively spliced product
49. M23323 s at T-CELL SURFACE GLYCOPROTEIN CD3 EPSILON CHAIN PRECURSOR
50. Z47055 s at "GB DEF=Partial cDNA sequence, farnesyl pyrophosphate synthetase like-4"
51. X73358 s at HAES-1 mRNA
52. U23852 s at GB DEF=T-lymphocyte specific protein tyrosine kinase p56lck (lck) abberant mRNA
53. U49835 s at CHIT1 Chitinase 1
54. U70439 s at PHAPI2b protein
55. U04241 s at Homolog of Drosophila enhancer of split m9/m10 mRNA
56. X97444 f at GB DEF=Transmembrane protein Tmp21-IIex B.10 LG10
1. D25278 at KIAA0036 gene
2. D43642 at YL-1 mRNA for YL-1 protein (nuclear protein with DNA-binding ability)
3. D78151 at 55.11 binding protein
4. D90086 at PDHB Pyruvate dehydrogenase (lipoamide) beta
5. L31801 at "SLC16A1 Solute carrier family 16 (monocarboxylic acid transporters), member 1"
6. L38707 at Diacylglycerol kinase (DAGK) mRNA
7. M34175 at "CLAPB1 Clathrin-associated/assembly/adaptor protein, large, beta 1"
8. M95627 at Angio-associated migratory cell protein (AAMP) mRNA
9. U09477 at "Clone 53BP1 p53-binding protein mRNA, partial cds"
10. U15782 at "CSTF3 Cleavage stimulation factor, 3' pre-RNA, subunit 3, 77 kD"
11. U43923 at Transcription factor SUPT4H mRNA
12. U46570 at Tetratricopeptide repeat protein (tpr1) mRNA
13. U57877 at "Integral membrane protein CII-3 mRNA, nuclear gene encoding mitochondrial protein"
14. X65867 at ADENYLOSUCCINATE LYASE
15. HG1980-HT2023 at "Tubulin, Beta 2"

B.11 LG11
1. AC002115 cds1 at "COX6B gene (COXG) extracted from Human DNA from overlapping chromosome 19 cosmids R31396, F25451, and R31076 containing COX6B and UPKA, genomic sequence"
2. D00763 at GAPD Glyceraldehyde-3-phosphate dehydrogenase
3. D23662 at UBL1 Ubiquitin-like protein
4. D26598 at Proteasome subunit HsC10-II
5. D49738 at Cytoskeleton associated protein (CG22) mRNA
6. D85758 at Enhancer of rudimentary homolog mRNA
7. D89667 at C-myc binding protein
8. HG1869-HT1904 at Male Enhanced Antigen
9. HG3549-HT3751 at Wilm'S Tumor-Related Protein
10. J04823 rna1 at Cytochrome c oxidase subunit VIII (COX8) mRNA
11. L16842 at UQCRC1 Ubiquinol-cytochrome c reductase core protein I
12. M19961 at COX5B Cytochrome c oxidase subunit Vb
13. M20471 at CLTA Clathrin light chain A
14. M94556 at SSBP Single-stranded DNA-binding protein
15. U22055 at 100 kDa coactivator mRNA
16. U34343 at "GB DEF=13 kD differentiation-associated protein mRNA, partial cds"
17. U37690 at RNA polymerase II subunit (hsRPB10) mRNA
18. U49785 at "DCT Dopachrome tautomerase (dopachrome delta-isomerase, tyrosine-related protein 2)"
19. U50733 at Dynamitin mRNA
20. U80040 at "ACO2 Aconitase 2, mitochondrial"
21. X15341 at CYTOCHROME C OXIDASE POLYPEPTIDE VIA-LIVER PRECURSOR
22. X15822 at COX7A2 Cytochrome c oxidase VIIa subunit (liver specific)
23. X16560 at COX7C Cytochrome c oxidase VIIc subunit
24. X52851 rna1 at Peptidylprolyl isomerase gene extracted from Human cyclophilin gene for cyclophilin (EC 5.2.1.8)

25. X63422 at "ATP5D ATP synthase, H+ transporting, mitochondrial F1 complex, delta subunit"
26. X83218 at "ATP5O ATP synthase, H+ transporting, mitochondrial F1 complex, O subunit (oligomycin sensitivity conferring protein)"
27. Z14244 at COX7B Cytochrome c oxidase subunit VIIb
28. Z69043 s at mRNA translocon-associated protein delta subunit precursor B.12 LG12
1. AF006084 at Arp2/3 protein complex subunit p41-Arc (ARC41) mRNA
2. D16217 at CAST Calpastatin
3. D21260 at 60S RIBOSOMAL PROTEIN L23
4. D38551 at KIAA0078 gene
5. HG2059-HT2114 at "Arrestin, Beta 2"
6. HG2279-HT2375 at Triosephosphate Isomerase
7. J02923 at LCP1 Lymphocyte cytosolic protein 1 (L-plastin)
8. J04173 at PGAM1 Phosphoglycerate mutase 1 (brain)
9. L10284 at CANX Calnexin
10. M23254 at "CAPN2 Calpain, large polypeptide L2"
11. U44772 at Palmitoyl protein thioesterase mRNA
12. X14046 at CD37 CD37 antigen
13. X16663 at HEMATOPOIETIC LINEAGE CELL SPECIFIC PROTEIN
14. X56494 at "PKM2 Pyruvate kinase, muscle"
15. X62320 at GRN Granulin
16. X75861 at TEGT Testis enhanced gene transcript
17. X90872 at Gp25L2 protein
18. X95404 at CFL1 Cofilin 1 (non-muscle)
19. X98085 at "TNR Tenascin R (restrictin, janusin)"
20. Z29505 at Alpha-CP1 mRNA
21. U41654 at RagA protein
22. U53204 at Plectin (PLEC1) mRNA
23. X56841 at HLA-E MHC class I antigen HLA-E
24. Y00097 s at ANX6 Annexin VI (p68)
25. U01691 s at "Annexin V (ANX5) gene, 5'-untranslated region"
26. L35249 s at "ATP6B2 ATPase, H+ transporting, lysosomal (vacuolar proton pump), beta polypeptide, 56/58 kD, isoform 2"
27. M36430 s at "GNB1 Guanine nucleotide binding protein (G protein), beta polypeptide 1"

B.13 LG13
1. D63506 at Unc-18homologue
2. D86964 at "KIAA0209 gene, partial cds"
3. J03459 at LTA4H Leukotriene A4 hydrolase
4. M14676 at "FYN FYN oncogene related to SRC, FGR, YES"
5. M60922 at Surface antigen mRNA
6. M62783 at "NAGA N-acetylgalactosarninidase, alpha-"
7. U12255 at IgG Fc receptor hFcRn mRNA
8. U31383 at G protein gamma-10 subunit mRNA
9. U40282 at Integrin-linked kinase (ILK) mRNA
10. U48263 at Pre-pro-orphanin FQ (OFQ) mRNA
11. U56637 at Capping protein alpha subunit isoform 1 mRNA
12. U65928 at JUN V-jun avian sarcoma virus 17 oncogene homolog
13. U97105 at Dihydropyrimidinase related protein-2
14. X82456 at MLN50 mRNA
15. X97074 at EEF2 Eukaryotic translation elongation factor 2
16. X98411 at GB DEF=Myosin-IE
17. Z36531 at FGL1 Fibrinogen-like 1
18. L10413 at "FNTA Farnesyltransferase, CAAX box, alpha"
19. L11284 at DUAL SPECIFICITY MITOGEN-ACTIVATED PROTEIN KINASE KINASE 1
20. L33075 at Ras GTPase-activating-like protein (IQGAP1) mRNA
21. HG2090-HT2152 s at "External Membrane Protein, 130 Kda (Gb:Z22971)"
22. M37238 s at "PLCG2 Phospholipase C, gamma 2 (phosphatidylinositol-specific)"
23. X59932 s at CSK C-src tyrosine kinase B.14 LS1
1. 5 ALL BM B-cell0.89 DFCI
2. 6 ALL BM T-cell-M 0.76 DFCI
3. 10 ALL BM T-cell Jul. 23, 1987-M 0.56 DFCI
4. 11 ALL BM T-cell Jun. 25, 1985-M 0.74 DFCI
5. 12 ALL BM B-cell Sep. 17, 1985-F 0.20 DFCI
6. 13 ALL BM B-cell Jul. 27, 1988-F 1.00 DFCI
7. 14 ALL BM T-cell Nov. 27, 1987-M 0.73 DFCI
8. 15 ALL BM B-cell Mar. 25, 1989-F 0.98 DFCI
9. 16 ALL BM B-cell Feb. 12, 1990-M 0.95 DFCI
10. 18 ALL BM B-cell-F 0.59 DFCI
11. 21 ALL BM B-cell Jan. 24, 1984-M 0.76 DFCI
12. 22 ALL BM B-cell May 27, 1988-M 0.37 DFCI
13. 23 ALL BM T-cell Jul. 9, 1991-M 0.77 DFCI
14. 24 ALL BM B-cell May 19, 1981-M 0.92 DFCI
15. 25 ALL BM B-cell Feb. 18, 1982-M 0.43 DFCI
16. 26 ALL BM B-cell-F 0.89 DFCI
17. 39 ALL BM B-cell-F 0.78 DFCI
18. 40 ALL BM B-cell May 16, 1980-F 0.68 DFCI
19. 41 ALL BM B-cell-F 0.99 DFCI
20. 44 ALL BM B-cell Nov. 19, 1998-F 0.97 DFCI
21. 45 ALL BM B-cell Nov. 19, 1998-M 0.88 DFCI
22. 46 ALL BM B-cell Jan. 8, 1999-F 0.84 DFCI
23. 47 ALL BM B-cell Sep. 5, 1986-M 0.81 DFCI
24. 48 ALL BM B-cell Feb. 28, 1992-F 0.94 DFCI
25. 52 AML PB M4 86 Success 0.61 CALGB
26. 55 ALL BM B-cell-F 0.73 St-Jude
27. 57 AML BM M2-F 0.22 St-Jude
28. 59 ALL BM B-cell-F 0.68 St-Jude
29. 60 AML BM M2-M 0.06 St-Jude
30. 62 AML PB-M 0.58 CCG
31. 65 AML BM-M 0.60 CCG
32. 67 ALL PB T-cell May 21, 1997-M 0.15 DFCI
33. 68 ALL PB B-cell Apr. 6, 1998-M 0.80 DFCI
34. 69 ALL PB B-cell Sep. 15, 1998-M 0.85 DFCI
35. 70 ALL PB B-cell Dec. 11, 1998-F 0.73 DFCI
36. 71 ALL PB B-cell Jul. 18, 1998 0.30 DFCI
37. 72 ALL PB B-cell Jul. 28, 1998 0.77 DFCI B.15 LS2
1. 28 AML BM M2 79 Failure 0.44 CALGB
2. 29 AML BM M2 34 Failure 0.74 CALGB
3. 30 AML BM M5 93 Failure 0.80 CALGB
4. 31 AML BM M4 77 Failure 0.61 CALGB
5. 32 AML BM M1 86 Failure 0.47 CALGB
6. 33 AML BM M2 70 Failure 0.89 CALGB
7. 34 AML BM M2 77 Success 0.64 CALGB
8. 36 AML BM M5 76 Success 0.94 CALGB
9. 37 AML BM M2 44 Success 0.95 CALGB
10. 38 AML BM M1 80 Success 0.73 CALGB
11. 50 AML BM M4 93 Failure 0.97 CALGB
12. 51 AML BM M2 57 Failure 1.00 CALGB
13. 52 AML PB M4 86 Success 0.61 CALGB
14. 53 AML BM M2 76 Success 0.89 CALGB
15. 63 AML PB-F 0.69 CCG
16. 65 AML BM-M 0.60 CCG B.16 LS3
1. 1 ALL BM B-cell Sep. 4, 1996-M 1.00 DFCI
2. 2 ALL BM T-cell-M 0.41 DFCI
3. 3 ALL BM T-cell-M 0.87 DFCI
4. 4 ALL BM B-cell0.91 DFCI
5. 5 ALL BM B-cell0.89 DFCI
6. 6 ALL BM T-cell-M 0.76 DFCI
7. 7 ALL BM B-cell Mar. 25, 1983-F 0.78 DFCI
8. 8 ALL BM B-cell-F 0.77 DFCI
9. 9 ALL BM T-cell-M 0.89 DFCI
10. 10 ALL BM T-cell Jul. 23, 1987-M 0.56 DFCI
11. 11 ALL BM T-cell Jun. 25, 1985-M 0.74 DFCI
12. 12 ALL BM B-cell Sep. 17, 1985-F 0.20 DFCI
13. 13 ALL BM B-cell Jul. 27, 1988-F 1.00 DFCI
14. 14 ALL BM T-cell Nov. 27, 1987-M 0.73 DFCI
15. 15 ALL BM B-cell Mar. 25, 1989-F 0.98 DFCI
16. 16 ALL BM B-cell Feb. 12, 1990-M 0.95 DFCI
17. 17 ALL BM B-cell Sep. 26, 1990-M 0.49 DFCI
18. 18 ALL BM B-cell-F 0.59 DFCI
19. 19 ALL BM B-cell0.80 DFCI
20. 21 ALL BM B-cell Jan. 24, 1984-M 0.76 DFCI
21. 22 ALL BM B-cell May 27, 1988-M 0.37 DFCI
22. 23 ALL BM T-cell Jul. 9, 1991-M 0.77 DFCI
23. 24 ALL BM B-cell May 19, 1981-M 0.92 DFCI
24. 25 ALL BM B-cell Feb. 18, 1982-M 0.43 DFCI
25. 26 ALL BM B-cell-F 0.89 DFCI
26. 27 ALL BM B-cell-F 0.82 DFCI
27. 28 AML BM M2 79 Failure 0.44 CALGB
28. 29 AML BM M2 34 Failure 0.74 CALGB
29. 32 AML BM M1 86 Failure 0.47 CALGB
30. 34 AML BM M2 77 Success 0.64 CALGB
31. 35 AML BM M1 67 Success 0.21 CALGB
32. 36 AML BM M5 76 Success 0.94 CALGB
33. 39 ALL BM B-cell-F 0.78 DFCI
34. 40 ALL BM B-cell May 16, 1980-F 0.68 DFCI
35. 41 ALL BM B-cell-F 0.99 DFCI
36. 44 ALL BM B-cell Nov. 19, 1998-F 0.97 DFCI
37. 45 ALL BM B-cell Nov. 19, 1998-M 0.88 DFCI
38. 46 ALL BM B-cell Jan. 8, 1999-F 0.84 DFCI
39. 47 ALL BM B-cell Sep. 5, 1986-M 0.81 DFCI
40. 48 ALL BM B-cell Feb. 28, 1992-F 0.94 DFCI
41. 49 ALL BM B-cell-M 0.84 DFCI
42. 50 AML BM M4 93 Failure 0.97 CALGB
43. 51 AML BM M2 57 Failure 1.00 CALGB
44. 52 AML PB M4 86 Success 0.61 CALGB
45. 53 AML BM M2 76 Success 0.89 CALGB
46. 54 AML BM M4-F 0.23 St-Jude
47. 55 ALL BM B-cell-F 0.73 St-Jude
48. 56 ALL BM B-cell-F 0.84 St-Jude
49. 57 AML BM M2-F 0.22 St-Jude
50. 58 AML BM M20.74 St-Jude
51. 59 ALL BM B-cell-F 0.68 St-Jude
52. 60 AML BM M2-M 0.06 St-Jude
53. 61 AML BM M10.40 St-Jude
54. 62 AML PB-M 0.58 CCG
55. 63 AML PB-F 0.69 CCG
56. 64 AML PB-M 0.52 CCG
57. 65 AML BM-M 0.60 CCG
58. 67 ALL PB T-cell May 21, 1997-M 0.15 DFCI
59. 68 ALL PB B-cell Apr. 6, 1998-M 0.80 DFCI
60. 69 ALL PB B-cell Sep. 15, 1998-M 0.85 DFCI
61. 70 ALL PB B-cell Dec. 11, 1998-F 0.73 DFCI
62. 71 ALL PB B-cell Jul. 18, 1998 0.30 DFCI
63. 72 ALL PB B-cell Jul. 28, 1998 0.77 DFCI B.17 LS4
1. 1 ALL BMB-cell Sep. 4, 1996-M 1.00 DFCI
2. 4 ALL BM B-cell0.91 DFCI
3. 5 ALL BM B-cell0.89 DFCI
4. 7 ALL BM B-cell Mar. 25, 1983-F 0.78 DFCI
5. 8 ALL BM B-cell-F 0.77 DFCI
6. 12 ALL BM B-cell Sep. 17, 1985-F 0.20 DFCI
7. 13 ALL BM B-cell Jul. 27, 1988-F 1.00 DFCI
8. 15 ALL BM B-cell Mar. 25, 1989-F 0.98 DFCI
9. 16 ALL BM B-cell Feb. 12, 1990-M 0.95 DFCI
10. 18 ALL BM B-cell-F 0.59 DFCI
11. 19 ALL BM B-cell0.80 DFCI
12. 20 ALL BM B-cell0.90 DFCI
13. 21 ALL BM B-cell Jan. 24, 1984-M 0.76 DFCI
14. 22 ALL BM B-cell May 27, 1988-M 0.37 DFCI
15. 24 ALL BM B-cell May 19, 1981-M 0.92 DFCI
16. 25 ALL BM B-cell Feb. 18, 1982-M 0.43 DFCI
17. 26 ALL BM B-cell-F 0.89 DFCI
18. 27 ALL BM B-cell-F 0.82 DFCI
19. 39 ALL BM B-cell-F 0.78 DFCI
20. 40 ALL BM B-cell May 16, 1980-F 0.68 DFCI
21. 41 ALL BM B-cell-F 0.99 DFCI
22. 42 ALL BM B-cell-F 0.42 DFCI
23. 43 ALL BM B-cell-F 0.66 DFCI
24. 44 ALL BM B-cell Nov. 19, 1998-F 0.97 DFCI
25. 45 ALL BM B-cell Nov. 19, 1998-M 0.88 DFCI
26. 46 ALL BM B-cell Jan. 8, 1999-F 0.84 DFCI
27. 47 ALL BM B-cell Sep. 5, 1986-M 0.81 DFCI
28. 48 ALL BM B-cell Feb. 28, 1992-F 0.94 DFCI
29. 49 ALL BM B-cell-M 0.84 DFCI
30. 55 ALL BM B-cell-F 0.73 St-Jude
31. 56 ALL BM B-cell-F 0.84 St-Jude
32. 59 ALL BM B-cell-F 0.68 St-Jude
33. 67 ALL PB T-cell May 21, 1997-M 0.15 DFCI
34. 68 ALL PB B-cell Apr. 6, 1998-M 0.80 DFCI
35. 69 ALL PB B-cell Sep. 15, 1998-M 0.85 DFCI
36. 70 ALL PB B-cell Dec. 11, 1998-F 0.73 DFCI
37. 71 ALL PB B-cell Jul. 18, 1998 0.30 DFCI
38. 72 ALL PB B-cell Jul. 28, 1998 0.77 DFCI B. 18 CG1
1. Hsa.10755 R78934 3' UTR 2a 146232 ENDOTHELIAL ACTIN-BINDING PROTEIN (*Homo sapiens*)
2. Hsa.1130 Z24727 gene 1 *H. sapiens* tropomyosin isoform mRNA, complete CDS.
3. Hsa.1131 T92451 3' UTR 1 118219 TROPOMYOSIN, FIBROBLAST AND EPITHELIAL MUSCLE-TYPE (HUMAN).
4. Hsa.1221 T60155 3' UTR 1 81422 ACTIN, AORTIC SMOOTH MUSCLE (HUMAN).
5. Hsa.1385 T53868 3' UTR 1 77996 Human peroxisomal enoyl-CoA hydratase-like protein (HPXEL) mRNA, complete cds.
6. Hsa.1479 X12496 gene 1 Human mRNA for erythrocyte membrane sialoglycoprotein beta (glycophorin C).
7. Hsa.14 Y00097 gene 1 Human mRNA for protein p68.
8. Hsa.15776 T79831 3' UTR 2a 114844 MAP KINASE PHOSPHATASE-1 (*Homo sapiens*)
9. Hsa.1763 M91463 gene 1 Human glucose transporter (GLUT4) gene, complete cds.
10. Hsa.1832 J02854 gene 1 MYOSIN REGULATORY LIGHT CHAIN 2, SMOOTH MUSCLE ISOFORM (HUMAN); contains element TAR1 repetitive element.
11. Hsa.2291 H06524 3' UTR 1 44386 GELSOLIN PRECURSOR, PLASMA (HUMAN).
12. Hsa.2344 X86693 gene 1 *H. sapiens* mRNA for hevin like protein.

13. Hsa.2456 U25138 gene 1 Human MaxiK potassium channel beta subunit mRNA, complete cds.
14. Hsa.2553 X74295 gene 1 *H. sapiens* mRNA for alpha 7B integrin.
15. Hsa.2560 X55187 gene 1 Human mRNA for alpha-actinin, partial cds.
16. Hsa.2747 U31525 gene 1 Human glycogenin mRNA, complete cds.
17. Hsa.27537 R48303 3' UTR 2a 153505 TYROSINE RICH ACIDIC MATRIX PROTEIN (*Bos taurus*)
18. Hsa.2794 T48904 3' UTR 1 70455 HEAT SHOCK 27 KD PROTEIN (HUMAN).
19. Hsa.28939 R60877 3' UTR 2a 42396 DELTA-CRYSTALLIN ENHANCER BINDING FACTOR (*Gallus gallus*)
20. Hsa.2939 X07767 gene 1 Human mRNA for cAMP-dependent protein kinase catalytic subunit type alpha (EC 2.7.1.37).
21. Hsa.3238 U26648 gene 1 Human syntaxin 5 mRNA, complete cds.
22. Hsa.3239 T78104 3' UTR 1 114499 Human proline-arginine-rich end leucine-rich repeat protein PRELP mRNA, complete cds.
23. Hsa.3305 X12369 gene 1 TROPOMYOSIN ALPHA CHAIN, SMOOTH MUSCLE (HUMAN).
24. Hsa.3348 X15880 gene 1 Human mRNA for collagen VI alpha-1 C-terminal globular domain.
25. Hsa.3349 X15882 gene 1 Human mRNA for collagen VI alpha-2 C-terminal globular domain.
26. Hsa.33 M64110 gene 1 Human caldesmon mRNA, complete cds.
27. Hsa.37937 R87126 3' UTR 2a 197371 MYOSIN HEAVY CHAIN, NONMUSCLE (*Gallus gallus*)
28. Hsa.41280 Z49269 gene 1 *H. sapiens* gene for chemokine HCC-1.
29. Hsa.41280 Z49269 gene 1 *H. sapiens* gene for chemokine HCC-1.
30. Hsa.41338 D31716 gene 1 Human mRNA for GC box bindig protein, complete cds.
31. Hsa.41369 X93510 gene 1 *H. sapiens* mRNA for 37 kDa LIM domain protein.
32. Hsa.43405 H81558 3' UTR 2a 238704 PROCYCLIC FORM SPECIFIC POLYPEPTIDE B1-ALPHA PRECURSOR (*Trapanosoma brucei brucei*)
33. Hsa.43431 H68239 3' UTR 2a 239077 SUPPRESSOR OF HAIRY WING PROTEIN (*Drosophila virilis*)
34. Hsa.466 U19969 gene 1 Human two-handed zinc finger protein ZEB mRNA, partial cds.
35. Hsa.467 H20709 3' UTR 1 173155 MYOSIN LIGHT CHAIN ALKALI, SMOOTH-MUSCLE ISOFORM (HUMAN).
36. Hsa.477 M28882 gene 1 Human MUC18 glycoprotein mRNA, complete cds.
37. Hsa.579 M80815 gene 1 *H. sapiens* a-L-fucosidase gene, exon 7 and 8, and complete cds.
38. Hsa.692 M76378 gene 1 Human cysteine-rich protein (CRP) gene, exons 5 and 6.
39. Hsa.692 M76378 gene 1 Human cysteine-rich protein (CRP) gene, exons 5 and 6.
40. Hsa.692 M76378 gene 1 Human cysteine-rich protein (CRP) gene, exons 5 and 6.
41. Hsa.8147 M63391 gene 1 Human desmin gene, complete cds.
42. Hsa.902 M94203 gene 1 *Homo sapiens* protein kinase gene, 3' end of cds and trinucleotide repeat region.

B.19 CG2
1. Hsa.1047 R84411 3' UTR 1 194660 SMALL NUCLEAR RIBONUCLEOPROTEIN ASSOCIATED PROTEINS B AND B' (HUMAN).
2. Hsa.1073 X12466 gene 1 Human mRNA for snRNP E protein.
3. Hsa.1143 M15841 gene 1 U2 SMALL NUCLEAR RIBONUCLEOPROTEIN B' (HUMAN).
4. Hsa.1145 T50797 3' UTR 1 78293 DEOXYURIDINE 5'-TRIPHOSPHATE NUCLEOTIDOHYDROLASE (HUMAN).
5. Hsa.1198 D38551 gene 1 Human mRNA (KIAA0078) for ORF (*s. pombe* rad21 gene product-related), complete cds.
6. Hsa.1205 R08183 3' UTR 1 127228 Q04984 10 KD HEAT SHOCK PROTEIN, MITOCHONDRIAL.
7. Hsa.1309 J04046 gene 1 Human calmodulin mRNA, complete cds.
8. Hsa.1591 T49732 3' UTR 1 67988Human SnRNP core protein Sm D2 mRNA, complete cds.
9. Hsa.1726 H24030 3' UTR 1 51695 S40237 CHAPERONIN.
10. Hsa.1765 M19156 gene 1 Human acidic keratin-10 mRNA, complete cds.
11. Hsa.1775 M77698 gene 1 TRANSCRIPTIONAL REPRESSOR PROTEIN YY1 (HUMAN); contains Alu repetitive element.
12. Hsa.2179 D49396 gene 1 Human mRNA for Apo1 Human (MER5(Aop1-Mouse)-like protein), complete cds.
13. Hsa.2316 T90280 3' UTR 1 110884 RIBOPHORIN II PRECURSOR (HUMAN).
14. Hsa.2451 U22055 gene 1 Human 100 kDa coactivator mRNA, complete cds.
15. Hsa.255 T69026 3' UTR 1 82338 60S RIBOSOMAL PROTEIN L9 (HUMAN).
16. Hsa.2582 T56934 3' UTR 1 68301 *H. sapiens* alpha NAC mRNA.
17. Hsa.2644 X54941 gene 1 *H. sapiens* ckshs1 mRNA for Cks1 protein homologue.
18. Hsa.26528 R33367 3' UTR 2a 135815 MEMBRANE COFACTOR PROTEIN PRECURSOR (*Homo sapiens*)
19. Hsa.2665 T68848 3' UTR 1 82178 PEPTIDYL-PROLYL CIS-TRANS ISOMERASE A (HUMAN).
20. Hsa.27686 H20426 3' UTR 2a 172457 NUCLEOSIDE DIPHOSPHATE KINASE (*Ginglymostoma cirratum*)
21. Hsa.2773 D63874 gene 1 Human mRNA for HMG-1.
22. Hsa.2777 Z23064 gene 1 *H. sapiens* mRNA gene for hnRNP G protein.
23. Hsa.2795 X15183 gene 1 Human mRNA for 90-kDa heat-shock protein.
24. Hsa.3152 D31885 gene 1 Human mRNA (KIAA0069) for ORF (novel proetin), partial cds.
25. Hsa.31630 R64115 3' UTR 2a 139618 ADENOSYLHOMOCYSTEINASE (*Homo sapiens*)
26. Hsa.333 1 T86473 3' UTR 1 114645 NUCLEOSIDE DIPHOSPHATE KINASE A (HUMAN).
27. Hsa.39753 R97912 3' UTR 2a 200181 SERINE/THREONINE-PROTEIN KINASE IPL1 (*Saccharomyces cerevisiae*)
28. Hsa.41283 U21090 gene 1 Human DNA polymerase delta small subunit mRNA, complete cds.
29. Hsa.462 U09564 gene 1 Human serine kinase mRNA, complete cds.
30. Hsa.490 T70062 3' UTR 1 80945 Human nuclear factor NF45 mRNA, complete cds.

31. Hsa.5971 U30825 gene 1 Human splicing factor SRp30c mRNA, complete cds.
32. Hsa.601 J05032 gene 1 Human aspartyl-tRNA synthetase alpha-2 subunit mRNA, complete cds.
33. Hsa.7395 R10066 3' UTR 2a 128808 PROHIBITIN (*Homo sapiens*)
34. Hsa.7652 R16156 3' UTR 2a 53170 RED CELL ACID PHOSPHATASE 1, ISOZYME F (*Homo sapiens*)
35. Hsa.773 H40095 3' UTR 1 175181 MACROPHAGE MIGRATION INHIBITORY FACTOR (HUMAN).
36. Hsa.831 M22382 gene 1 MITOCHONDRIAL MATRIX PROTEIN P1 PRECURSOR (HUMAN).
37. Hsa.852 M88279 gene 1 P59 PROTEIN (HUMAN).
38. Hsa.951 M36981 gene 1 Human putative NDP kinase (nm23-H2S) mRNA, complete cds.
39. Hsa.957 M26697 gene 1 Human nucleolar protein (B23) mRNA, complete cds.

B.20 CG3
1. Hsa.120 D14662 gene 1 Human mRNA for ORF, complete cds.
2. Hsa.1276 U05681 gene 1-Human proto-oncogene (BCL3) gene, exons 3-9 and complete cds.
3. Hsa.1278 R80966 3' UTR1 147324 CLATHRIN LIGHT CHAIN B (HUMAN).
4. Hsa.1280 X16354 gene 1 Human mRNA for transmembrane carcinoembryonic antigen BGPa (formerly TM1-CEA).
5. Hsa.1387 U14631 gene 1 Human 11 beta-hydroxysteroid dehydrogenase type II mRNA, complete cds.
6. Hsa.1579 D42047 gene 1 Human mRNA (KIAA0089) for ORF (mouse glycerophosphate dehydrogenase-related), partial cds.
7. Hsa.1804 M93010 gene 1 Human epithelial cell markerprotein 1 (HMe1) mRNA, complete cds.
8. Hsa.1902 L05144 gene 1 PHOSPHOENOLPYRUVATE CARBOXYKINASE, CYTOSOLIC (HUMAN); contains Alu repetitive element; contains element PTR5 repetitive element.
9. Hsa.19843 T98835 3' UTR 2a 122341 80.7 KD ALPHA TRANS-INDUCING PROTEIN (*Bovine herpesvirus type 1*)
10. Hsa.2092 L06328 gene 1 Human voltage-dependent anion channel isoform 2 (VDAC) mRNA, complete cds.
11. Hsa.2097 M36634 gene 1 Human vasoactive intestinal peptide (VIP) mRNA, complete cds.
12. Hsa.2243 L40380 gene 1 *Homo sapiens* thyroid receptor interactor (TRIP11) mRNA, 3' end of cds.
13. Hsa.2255 L40904 gene 1 *H. sapiens* peroxisome proliferator activated receptor gamma, complete cds.
14. Hsa.2467 U12387 gene 1 Human thiopurine methyltransferase (TPMT) mRNA, complete cds.
15. Hsa.25322 R44301 3' UTR 2a 34262 MINERALOCORTICOID RECEPTOR (*Homo sapiens*)
16. Hsa.2547 T62904 3' UTR 1 86074 3-KETOACYL-COA THIOLASE PEROXISOMAL PRECURSOR (HUMAN).
17. Hsa.2551 X57348 gene 1 *H. sapiens* mRNA (clone 9112).
18. Hsa.28390 H06189 3' UTR 2a 43718 CELL DIVISION CONTROL PROTEIN 2 HOMOLOG (*Zea mays*)
19. Hsa.2951 M60484 gene 1 Human protein phosphatase 2A catalytic subunit-beta gene, complete cds.
20. Hsa.3068 X16356 gene 1 Human mRNA for transmembrane carcinoembryonic antigen BGPC (part.) (formerly TM3-CEA).
21. Hsa.3299 X02875 gene 1 Human mRNA (3'-fragment) for (2'-5') oligo A synthetase E (1,8 kb RNA).
22. Hsa.329 D15049 gene 1 Human mRNA for protein tyrosine phosphatase.
23. Hsa.335 U02082 gene 1 Human guanine nucleotide regulatory protein (tim1) mRNA, complete cds.
24. Hsa.34312 H87366 3' UTR 2a 252444 CENTROMERIC PROTEIN E (*Homo sapiens*)
25. Hsa.34776 H14372 3' UTR 2a 48518 ATP-BINDING CASSETTE TRANSPORTER 1 (*Mus musculus*)
26. Hsa.36710 U33849 gene 1 Human lymphoma proprotein convertase (LPC) mRNA, complete cds.
27. Hsa.41239 X73424 gene 1 PROPIONYL-COA CARBOXYLASE BETA CHAIN (HUMAN).
28. Hsa.41282 X87159 gene 1 *H. sapiens* mRNA for beta subunit of epithelial amiloride-sensitive sodium channel.
29. Hsa.421 D16294 gene 1 Human mRNA for mitochondrial 3-oxoacyl-CoA thiolase, complete cds.
30. Hsa.422 T64467 3' UTR 1 80480 P33477 ANNEXIN XI.
31. Hsa.43201 H69695 3' UTR 2a 212787 EBNA-2 NUCLEAR PROTEIN (Epstein-barr virus)
32. Hsa.43279 H64489 3' UTR 2a 238846 LEUKOCYTE ANTIGEN CD37 (*Homo sapiens*)
33. Hsa.51 D11466 gene 1 N-ACETYLGLUCOSAMINYL-PHOSPHATIDYLINOSITOL BIOSYNTHETIC (HUMAN).
34. Hsa.570 L12168 gene 1 *Homo sapiens* adenylyl cyclase-associated protein (CAP) mRNA, complete cds.
35. Hsa.667 L25616 gene 1 Human CG1 protein mRNA, complete cds.
36. Hsa.694 M61199 gene 1 Human cleavage signal 1 protein mRNA, complete cds.
37. Hsa.8175 H49870 3' UTR 2a 178915 MAD PROTEIN (*Homo sapiens*)
38. Hsa.84 D11086 gene 1 Human mRNA for interleukin 2 receptor gamma chain.
39. Hsa.865 M84490 gene 1 Human extracellular signal-regulated kinase 1 mRNA, 3' end.
40. Hsa.9994 T51539 3' UTR 2a 72395 HEPATOCYTE GROWTH FACTOR-LIKE PROTEIN PRECURSOR (*Homo sapiens*)—68dd 5699-4733 4d62-1290 1927 Content-Type: application/octet-stream Content-Transfer-Encoding: 7bit Content-MD5: NAIwVJQ4msWkg7LKaY/Asw==Content-Description: rank2b.info B.21 CG4
1. Hsa.10358 T53694 3' UTR 2a 69762 COMPLEMENT C1Q SUBCOMPONENT, A CHAIN PRECURSOR (*Homo sapiens*)
2. Hsa.10522 T54767 3' UTR 2a 73802 SPARC PRECURSOR (*Homo sapiens*)
3. Hsa.1066 M14676 gene 1 PROTO-ONCOGENE TYROSINE-PROTEIN KINASE FYN (HUMAN).
4. Hsa.10755 R78934 3' UTR 2a 146232 ENDOTHELIAL ACTIN-BINDING PROTEIN (*Homo sapiens*)
5. Hsa.108 D13665 gene 1 Human mRNA for osteoblast specific factor 2 (OSF-2p1).
6. Hsa.1130 Z24727 gene 1 *H. sapiens* tropomyosin isoform mRNA, complete CDS.
7. Hsa.1131 T92451 3' UTR 1 118219 TROPOMYOSIN, FIBROBLAST AND EPITHELIAL MUSCLE-TYPE (HUMAN).
8. Hsa.1139 T88723 3' UTR 1 109876 UBIQUITIN (HUMAN).

9. Hsa.114 L10717 gene 1 TYROSINE-PROTEIN KINASE LYK (HUMAN); contains Alu repetitive element.
10. Hsa.11582 T61333 3' UTR 2a 78034 METALLOPROTEINASE INHIBITOR 3 PRECURSOR (*Gallus gallus*)
11. Hsa.11616 T60778 3' UTR 2a 76539 MATRIX GLA-PROTEIN PRECURSOR (*Rattus norvegicus*)
12. Hsa.11854 T62067 3' UTR 2a 85658 COMPLEMENT C3 PRECURSOR (*Mus musculus*)
13. Hsa.11850 T93284 3' UTR 2a 118800 COMPLEMENT C1S COMPONENT PRECURSOR (*Homo sapiens*)
14. Hsa.1221 T60155 3' UTR 1 81422 ACTIN, AORTIC SMOOTH MUSCLE (HUMAN).
15. Hsa.1288 T53889 3' UTR 1 78017 COMPLEMENT C1R COMPONENT PRECURSOR (HUMAN).
16. Hsa.1308 M60335 gene 1 Human vascular cell adhesion molecule 1 mRNA, complete cds.
17. Hsa.1331 T51558 3' UTR 1 72223 PROCOLLAGEN ALPHA 1(I) CHAIN PRECURSOR (HUMAN).
18. Hsa.1346 T78323 3' UTR 1 114526 PROCOLLAGEN ALPHA 1(IV) CHAIN PRECURSOR (HUMAN).
19. Hsa.1347 X05610 gene 1 Human mRNA for type IV collagen alpha (2) chain.
20. Hsa.1385 T53868 3' UTR 1 77996 Human peroxisomal enoyl-CoA hydratase-like protein (HPXEL) mRNA, complete cds.
21. Hsa.1444 M14539 gene 1 Human factor XII subunit a mRNA, 3' end.
22. Hsa.1464 M35878 gene 1 Human insulin-like growth factor-binding protein-3 gene, complete cds, clone HL1006d.
23. Hsa.1479 X12496 gene 1 Human mRNA for erythrocyte membrane sialoglycoprotein beta (glycophorin C).
24. Hsa.14 Y00097 gene 1 Human mRNA for protein p68.
25. Hsa.15101 T75577 3' UTR 2a 112940 1D-MYO-INOSITOL-TRISPHOSPHATE 3-KINASE B (*Homo sapiens*)
26. Hsa.1515 M85289 gene 1 Human heparan sulfate proteoglycan (HSPG2) mRNA, complete cds.
27. Hsa.1532 U20982 gene 1 Human insulin-like growth factor binding protein-4 (IGFBP4) gene, promoter and complete cds.
28. Hsa.1569 X86809 gene 1 *H. sapiens* mRNA for major astrocytic phosphoprotein PEA-15.
29. Hsa.15776 T79831 3' UTR 2a 114844 MAP KINASE PHOSPHATASE-1 (*Homo sapiens*)
30. Hsa.1610 M96233 gene 1 Human glutathione transferase class mu number 4 (GSTM4) gene, complete cds.
31. Hsa.1687 R73052 3' UTR 1 156448 *Homo sapiens* growth-arrest-specific protein (gas) mRNA, complete cds.
32. Hsa.1763 M91463 gene 1 Human glucose transporter (GLUT4) gene, complete cds.
33. Hsa.1768 M63509 gene 1 Human glutathione transferase M2 (GSTM2) nRNA, complete cds.
34. Hsa.1806 M69135 gene 1 Human monoamine oxidase B (MAOB) gene, exon 15.
35. Hsa.1832 J02854 gene 1 MYOSIN REGULATORY LIGHT CHAIN 2, SMOOTH MUSCLE ISOFORM (HUMAN); contains element TAR1 repetitive element.
36. Hsa.18321 R44887 3' UTR 2a 33869 NEDD5 PROTEIN (*Mus musculus*)
37. Hsa.18790 T94993 3' UTR 2a 119988 FIBROBLAST GROWTH FACTOR RECEPTOR 2 PRECURSOR (*Homo sapiens*)
38. Hsa.1939 X17042 gene 1 Human mRNA for hematopoetic proteoglycan core protein.
39. Hsa.1939 X17042 gene 1 Human mRNA for hematopoetic proteoglycan core protein.
40. Hsa.2014 J03040 gene 1 SPARC PRECURSOR (HUMAN); contains MSR1 repetitive element.
41. Hsa.205 L12350 gene 1 THROMBOSPONDIN 2 PRECURSOR (HUMAN).
42. Hsa.2095 T51852 3' UTR 1 75026 VIMENTIN (HUMAN).
43. Hsa.2126 D26129 gene 1 RIBONUCLEASE PANCREATIC PRECURSOR (HUMAN); contains element MER21 repetitive element.
44. Hsa.2135 U21128 gene 1 Human lumican mRNA, complete cds.
45. Hsa.21757 R72104 3' UTR 2a 155771 BONE MORPHOGENETIC PROTEIN 1 PRECURSOR (*Homo sapiens*)
46. Hsa.2291 H06524 3' UTR 1 44386 GELSOLIN PRECURSOR, PLASMA (HUMAN).
47. Hsa.230 U05291 gene 1 Human fibromodulin mRNA, partial cds.
48. Hsa.2337 X06700 gene 1 Human mRNA 3' region for pro-alpha1(III) collagen.
49. Hsa.2344 X86693 gene 1 *H. sapiens* mRNA for hevin like protein.
50. Hsa.24506 R44418 3' UTR 2a 34853 EBNA-2 NUCLEAR PROTEIN (Epstein-barr virus)
51. Hsa.2456 U25138 gene 1 Human MaxiK potassium channel beta subunit mRNA, complete cds.
52. Hsa.2553 X74295 gene 1 *H. sapiens* mRNA for alpha 7B integrin.
53. Hsa.2560 X55187 gene 1 Human mRNA for alpha-actinin, partial cds.
54. Hsa.2614 X79981 gene 1 *H. sapiens* VE-cadherin mRNA.
55. Hsa.2747 U31525 gene 1 Human glycogenin mRNA, complete cds.
56. Hsa.2748 X54232 gene 1 Human mRNA for heparan sulfate proteaglycan (glypican).
57. Hsa.27537 R48303 3' UTR 2a 153505 TYROSINE RICH ACIDIC MATRIX PROTEIN (*Bos taurus*)
58. Hsa.2794 T48904 3' UTR 1 70455 HEAT SHOCK 27 KD PROTEIN (HUMAN).
59. Hsa.28608 R603 18 3' UTR 2a 42159 LEUKOCYTE SURFACE ANTIGEN CD53 (*Homo sapiens*)
60. Hsa.28939 R60877 3' UTR 2a 42396 DELTA-CRYSTALLIN ENHANCER BINDING FACTOR (*Gallus gallus*)
61. Hsa.2939 X07767 gene 1 Human mRNA for cAMP-dependent protein kinase catalytic subunit type alpha (EC 2.7.1.37).
62. Hsa.313 U14394 gene 1 Human tissue inhibitor of metalloproteinases-3 mRNA, complete cds.
63. Hsa.31933 R67343 3' UTR 2a 140965 IMMEDIATE-EARLY REGULATORY PROTEIN IE-N (*Autographa californica* nuclear polyhedrosis virus)
64. Hsa.3238 U26648 gene 1 Human syntaxin 5 mRNA, complete cds.
65. Hsa.3239 T78104 3' UTR 1 114499 Human proline-arginine-rich end leucine-rich repeat protein PRELP mRNA, complete cds.
66. Hsa.3305 X12369 gene 1 TROPOMYOSIN ALPHA CHAIN, SMOOTH MUSCLE (HUMAN).
67. Hsa.3348 X15880 gene 1 Human mRNA for collagen VI alpha-1 C-terminal globular domain.

68. Hsa.3349 X15882 gene 1 Human mRNA for collagen VI alpha-2 C-terminal globular domain.
69. Hsa.33 M64110 gene 1 Human caldesmon mRNA, complete cds.
70. Hsa.36689 Z50753 gene 1 *H. sapien* mRNA for GCAP-II/uroguanylin precursor.
71. Hsa.36694 D25217 gene 1 Human mRNA (KIAA0027) for ORF, partial cds.
72. Hsa.36952 H43887 3' UTR 2a 183264 COMPLEMENT FACTOR D PRECURSOR (*Homo sapiens*)
73. Hsa.3764 H02540 3' UTR 1 151270 CATHEPSIN L PRECURSOR (HUMAN).
74. Hsa.37715 H62466 3' UTR 2a 209654 COLLAGEN ALPHA 3(VI) CHAIN (*Gallus gallus*)
75. Hsa.37937 R87126 3' UTR 2a 197371 MYOSIN HEAVY CHAIN, NONMUSCLE (*Gallus gallus*)
76. Hsa.3852 R49855 3' UTR 2a 152637 COAGULATION FACTOR V PRECURSOR (*Homo sapiens*)
77. Hsa.400 D30755 gene 1 Human mRNA (HA1652) for ORF, partial cds.
78. HSAC07
79. Hsa.41280 Z49269 gene 1 *H. sapiens* gene for chemokine HCC-1.
80. Hsa.41280 Z49269 gene 1 *H. sapiens* gene for chemokine HCC-1.
81. Hsa.41338 D31716 gene 1 Human mRNA for GC box bindig protein, complete cds.
82. Hsa.41369 X93510 gene 1 *H. sapiens* mRNA for 37 kDa LIM domain protein.
83. Hsa.43405 H81558 3' UTR 2a 238704 PROCYCLIC FORM SPECIFIC POLYPEPTIDE B1-ALPHA PRECURSOR (*Trapanosoma brucei brucei*)
84. Hsa.43431 H68239 3' UTR 2a 239077 SUPPRESSOR OF HAIRY WING PROTEIN (*Drosophila Virilis*)
85. Hsa.44350 H79136 3' UTR2a235022 ALPHA-2-MACROGLOBULIN PRECURSOR (*Homo sapiens*)
86. Hsa.466 U19969 gene 1 Human two-handed zinc finger protein ZEB mRNA, partial cds.
87. Hsa.467 H20709 3' UTR 1 173155 MYOSIN LIGHT CHAIN ALKALI, SMOOTH-MUSCLE ISOFORM (HUMAN).
88. Hsa.477 M28882 gene 1 Human MUC18 glycoprotein mRNA, complete cds.
89. Hsa.579 M80815 gene 1 *H. sapiens* a-L-fucosidase gene, exon 7 and 8, and complete cds.
90. Hsa.628 H80975 3' UTR 1 240954 PLASMA PROTEASE C1 INHIBITOR PRECURSOR (HUMAN).
91. Hsa.6484 T95046 3' UTR 2a 120085 PROTEASE DO PRECURSOR (*Escherichia coli*)
92. Hsa.6633 R61359 3' UTR 2a 37866 BASIGIN PRECURSOR (*Gallus gallus*)
93. Hsa.680 J03210 gene 1 Human collagenase type IV mRNA, 3' end.
94. Hsa.692 M76378 gene 1 Human cysteine-rich protein (CRP) gene, exons 5 and 6.
95. Hsa.692 M76378 gene 1 Human cysteine-rich protein (CRP) gene, exons 5 and 6.
96. Hsa.692 M76378 gene 1 Human cysteine-rich protein (CRP) gene, exons 5 and 6.
97. Hsa.8007 R32804 3' UTR 1 135146 GLUCOSE TRANSPORTER TYPE 3, BRAIN (HUMAN); contains Alu repetitive element.
98. Hsa.806 M64098 gene 1 Human high density lipoprotein binding protein (HBP) mRNA, complete cds.
99. Hsa.8125 T71025 3' UTR 1 84103 Human (HUMAN).
100. Hsa.8147 M63391 gene 1 Human desmin gene, complete cds.
101. Hsa.879 H41129 3' UTR 1 175539 GALECTIN-1 (HUMAN); contains Alu repetitive element.
102. Hsa.8 U01691 gene 1 Human annexin V (ANX5) gene, exon 13 and 3'-untranslated region.
103. Hsa.902 M94203 gene 1 *Homo sapiens* protein kinase gene, 3' end of cds and trinucleotide repeat region.
104. Hsa.9103 T67406 3' UTR 2a 81780 COMPLEMENT C4 PRECURSOR (*Homo sapiens*)
105. Hsa.9153 T47069 3' UTR 2a 71011 ATP SYNTHASE A CHAIN (*Trypanosoma brucei brucei*)
106. Hsa.925 M69066 gene 1 MOESIN (HUMAN); contains PTR5 repetitive element.
107. Hsa.981 L11373 gene 1 Human protocadherin 43 mRNA, complete cds for abbreviated PC43.
108. Hsa.984 M33210 gene 1 Human colony stimulating factor 1 receptor (CSF1R) gene, exon 5.

B.22 CG5
1. Hsa.11712 T61446 3' UTR 2a 79900 PUTATIVE DNA BINDING PROTEIN A20 (*Homo sapiens*)
2. Hsa.1312 J05158 gene 1 Human carboxypeptidase N mRNA, 3' end.
3. Hsa.176 L20469 gene 1 Human truncated dopamine D3 receptor mRNA, complete cds.
4. Hsa.17822 T89422 3' UTR2a 116291 CELL DIVISION CONTROL PROTEIN 3 (*Saccharomyces cerevisiae*)
5. Hsa.19143 H02258 3' UTR 2a 150726 VERPROLIN (*Saccharomyces cerevisiae*)
6. Hsa.21868 H73943 3' UTR 2a 232777 40 KD PROTEIN KINASE (*Xenopus laevis*)
7. Hsa.2409 U24077 gene 1 Human p58 natural killer cell receptor precursor mRNA, clone cl-39, complete cds.
8. Hsa.26945 R35665 3' UTR 2a 137017 EPIDERMAL GROWTH FACTOR RECEPTOR PRECURSOR (*Homo sapiens*)
9. Hsa.27560 R72164 3' UTR 2a 155799 HYPOTHETICAL 76.3 KD PROTEIN K04H4.2 IN CHROMOSOME III (*Caenorhabditis elegans*)
10. Hsa.2985 X69550 gene 1 *H. sapiens* mRNA for rho GDP-dissociation Inhibitor 1.
11. Hsa.30310 H06877 3' UTR 2a 44550 GTP-BINDING PROTEIN HFLX (*Escherichia coli*)
12. Hsa.3225 U27699 gene 1 Human pephBGT-1 betaine-GABA transporter mRNA, complete cds.
13. Hsa.32358 R70535 3' UTR 2a 142310 T-CELL RECEPTOR GAMMA CHAIN PRECURSOR V REGION (*Mus musculus*)
14. Hsa.33699 H02630 3' UTR 2a 151355 TRANSCRIPTIONAL REPRESSOR PROTEIN YY1 (*Homo sapiens*)
15. Hsa.33982 H05966 3' UTR 2a 43697 REGULATOR OF CHROMOSOME CONDENSATION (*Homo sapiens*)
16. Hsa.34351 H08678 3' UTR 2a 46062 INSULIN-LIKE GROWTH FACTOR BINDING PROTEIN COMPLEX ACID LABILE CHAIN PRECURSOR (*Rattus norvegicus*)
17. Hsa.35201 H19272 3' UTR 2a 171859 CIRCUMSPOROZOITE PROTEIN PRECURSOR (*Plasmodium berghei yoelii*)
18. Hsa.35518 H22842 3' UTR 2a 51383 COMPLEMENT RECEPTOR TYPE 1 PRECURSOR (*Homo sapiens*)
19. Hsa.35528 H22939 3' UTR 2a 51719 GLYCOGENIN (*Homo sapiens*)
20. Hsa.36657 U20659 gene 1 Human RNA polymerase II subunit hsRPB7 mRNA, complete cds.

21. Hsa.37058 H46136 3' UTR 2a 177791 HOMEOBOX PROTEIN HOX-A10 (*Homo sapiens*)
22. Hsa.3969 R55778 3' UTR 2a 40736 NEDD5 PROTEIN (*Mus musculus*)
23. Hsa.41123 J00277 gene 1 Human (genomic clones lambda-[SK2-T2, HS578T]; cDNA clones RS-[3,4, 6]) c-Ha-ras1 proto-oncogene, complete coding sequence.
24. Hsa.41136 J00073 gene 1 Human alpha-cardiac actin gene, exon 6 and 3' flank.
25. Hsa.41164 U07664 gene 1 Human HB9 homeobox gene, exons 2 and 3 and complete cds.
26. Hsa.42738 H70609 3' UTR 2a 234133 CA2+/CALMODULIN-RESPONSIVE ADENYLATE CYCLASE (*Drosophila melanogaster*)
27. Hsa.4907 R83354 3' UTR 2a 186615 GDP DISSOCIATION INHIBITOR FOR RHO PROTEIN (*Bos taurus*)
28. Hsa.6048 H87465 3' UTR 2a 252514 PRE-MRNA SPLICING FACTOR SRP75 (*Homo sapiens*)
29. Hsa.848 X04500 gene 1 Human gene for prointerleukin 1 beta.

B.23 CG6
1. Hsa.1000 M95678 gene 1 *Homo sapiens* phospholipase C-beta-2 mRNA, complete cds.
2. Hsa.1163 L36818 gene 1 Human (clone 51C-3) 51C protein mRNA, complete cds.
3. Hsa.142 L19956 gene 1 Human aryl sulfotransferase mRNA, complete cds.
4. Hsa.1554 M80613 gene 1 Human homolog of *Drosophila* female sterile homeotic mRNA, complete cds.
5. Hsa.1556 L13738 gene 1 Human activated p21cdc42Hs kinase (ack) mRNA, complete cds.
6. Hsa.166 U00968 gene 1 STEROL REGULATORY ELEMENT BINDING PROTEIN 1 (HUMAN).
7. Hsa.1672 M98343 gene 1 *Homo sapiens* amplaxin (EMS1) mRNA, complete cds.
8. Hsa.1724 M87503 gene 1 TRANSCRIPTIONAL REGULATOR ISGF3 GAMMA SUBUNIT (HUMAN).
9. Hsa.18462 H53092 3' UTR 2a 202444 PROBABLE SERINE/THREONINE-PROTEIN KINASE C16C9.07 (*Schizosaccharomyces pombe*)
10. Hsa.2015 M77693 gene 1 Spermidine/spermine N1-acetyltransferase mRNA, complete cds.
11. Hsa.21859 R09468 3' UTR 2a 128032 PROTEIN-TYROSINE PHOSPHATASE PTP-S (*Rattus norvegicus*)
12. Hsa.2199 U18299 gene 1 Human damage-specific DNA binding protein DDBa p127 subunit (DDB1) mRNA, complete cds.
13. Hsa.2386 X86018 gene 1 *H. sapiens* mRNA for MUF1 protein.
14. Hsa.24490 R49719 3' UTR 2a 38755 GAMMA-AMINOBUTYRIC-ACID RECEPTOR BETA-4 SUBUNIT PRECURSOR (*Gallus gallus*)
15. Hsa.256 L10911 gene 1 *Homo sapiens* splicing factor (CC1.4) mRNA, complete cds.
16. Hsa.25762 R67987 3' UTR 2a 138233 PRE-MRNA SPLICING FACTOR SRP75 (*Homo sapiens*)
17. Hsa.26719 H15069 3' UTR 2a 49237 PROTEIN KINASE CLK (*Mus musculus*)
18. Hsa.27324 R54837 3' UTR 2a 154443 INTERFERON ALPHA-6 PRECURSOR (*Homo sapiens*)
19. Hsa.27491 R98959 3' UTR 1 200858 *Homo sapiens* very long chain acyl-CoA dehydrogenase gene, exons 1-20, complete cds.
20. Hsa.3022 X68148 gene 1 *H. sapiens* SHC mRNA.
21. Hsa.3104 X79353 gene 1 *H. sapiens* XAP-4 mRNA for GDP-dissociation inhibitor.
22. Hsa.3166 X78817 gene 1 *H. sapiens* partial C1 mRNA.
23. Hsa.3280 L40392 gene 1 *Homo sapiens* (clone S164) mRNA, 3' end of cds.
24. Hsa.33277 R80779 3' UTR 2a 146868 MIXED LINEAGE KINASE 1 (*Homo sapiens*)
25. Hsa.35804 H28373 3' UTR 2a 161909 T-CELL PROTEIN-TYROSINE PHOSPHATASE (*Homo sapiens*)
26. Hsa.36528 R85479 3' UTR 2a 180094 TRANSCRIPTIONAL ACTIVATOR FE65 (*Rattus norvegicus*)
27. Hsa.39432 R95874 3' UTR 2a 199264 RETROVIRUS-RELATED ENV POLYPROTEIN (*Homo sapiens*)
28. Hsa.3952 H40891 3' UTR 2a 175983 NODULATION PROTEIN Q (*Azospirillum brasilense*)
29. Hsa.39621 R96909 3' UTR 2a 200337 IMMEDIATE-EARLY PROTEIN IE180 (Pseudorabies virus)
30. Hsa.41259 Z14000 gene 1 RING1 PROTEIN (HUMAN).
31. Hsa.5141 D63876 gene 1 Human mRNA for ORF.
32. Hsa.5633 R59097 3' UTR 2a 42048 TYROSINE-PROTEIN KINASE RECEPTOR TIE-1 PRECURSOR (*Mus musculus*)
33. Hsa.6353 R62438 3' UTR 2a 36234 PARANEOPLASTIC ENCEPHALOMYELITIS ANTIGEN HUD (*Homo sapiens*)
34. Hsa.6422 T71643 3' UTR 2a 110357 CYCLIC-AMP-DEPENDENT TRANSCRIPTION FACTOR ATF-4 (*Homo sapiens*)
35. Hsa.6438 R61324 3' UTR 2a 42469 GALACTOSYLTRANSFERASE ASSOCIATED PROTEIN KINASE P58/GTA (*Homo sapiens*)
36. Hsa.661 X80230 gene 1 *H. sapiens* mRNA (clone C-2k) mRNA for serine/threonine protein kinase.
37. Hsa.68 M86842 gene 1 Human cAMP response element regulatory protein (CREB2) mRNA, complete cds.
38. Hsa.7671 T65594 3' UTR 2a 21833 SRC SUBSTRATE P80/85 PROTEINS (*Gallus gallus*)
39. Hsa.8301 T64974 3' UTR 2a 66833 BETA-3 ADRENERGIC RECEPTOR (*Homo sapiens*)
40. Hsa.8551 R56443 3' UTR 2a 40981 TRANS-ACTING TRANSCRIPTIONAL PROTEIN ICPO (Herpes simplex virus)
41. Hsa.855 L25851 gene 1 INTEGRIN ALPHA-E PRECURSOR (HUMAN); contains Alu repetitive element.
42. Hsa.8736 D63878 gene 1 Human mRNA for ORF.
43. Hsa.9631 T49397 3' UTR 2a 67478 SHC TRANSFORMING PROTEINS 46.8 KD AND 51.7 KD PRECURSOR (*Homo sapiens*)
44. Hsa.9667 H47646 3' UTR 1 193666 Human mRNA for ZFM1 protein, complete cds.
45. Hsa.9744 R52081 3' UTR 2a 40295 TRANSCRIPTIONAL ACTIVATOR GCN5 (*Saccharomyces cerevisiae*)

B.24 CG7
1. Hsa.11839 T62191 3' UTR 2a 79090 FRUCTOSE-1,6-BISPHOSPHATASE (*Sus scrofa*)
2. Hsa.1228 X56411 gene 1 *H. sapiens* ADH4 gene for class II alcohol dehydrogenase (pi subunit), exon 1.
3. Hsa.1274 D90391 gene 1 Human gene for branched chain alpha-keto acid dehydrogenase (EC 1.2.4.4) E-1-beta subunit, exon 10 and 3' flanking region.
4. Hsa.1373 K03192 gene 1 Human cytochrome P-450 mRNA, partial.
5. Hsa.1373 K03192 gene 1 Human cytochrome P-450 mRNA, partial.

6. Hsa.1453 M86868 gene 1 Human gamma amino butyric acid (GABA rho2) gene mRNA, complete cds.
7. Hsa.1670 M23419 gene 1 INITIATION FACTOR 5A (HUMAN); contains element PTR5 repetitive element.
8. Hsa.16742 R38513 3' UTR 2a 26871 FIBROBLAST GROWTH FACTOR RECEPTOR 2 PRECURSOR (*Homo sapiens*)
9. Hsa.168 U02493 gene 1 Human 54 kDa protein mRNA, complete cds.
10. Hsa.17091 T89175 3' UTR 2a 110022 G1/S-SPECIFIC CYCLIN D1 (*Homo sapiens*)
11. Hsa.1774 X12876 gene 1 Human mRNA fragment for cytokeratin 18.
12. Hsa.1860 M65105 gene 1 SODIUM-DEPENDENT NORADRENALINE TRANSPORTER (HUMAN); contains Alu repetitive element.
13. Hsa.2626 X57110 gene 1 PROTO-ONCOGENE C-CBL (HUMAN); contains Alu repetitive element.
14. Hsa.33277 R80779 3' UTR 2a 146868 MIXED LINEAGE KINASE 1 (*Homo sapiens*)

B.25 CG8
1. Hsa.10807 T56460 3' UTR 2a 72960 HLA CLASS II HISTOCOMPATIBILITY ANTIGEN, GAMMA CHAIN PRECURSOR (*Homo sapiens*)
2. Hsa.42746 H70635 3' UTR 2a 234198 EXTRACELLULAR SIGNAL-REGULATED KINASE 1 (*Candida albicans*)
3. Hsa.32463 R71875 3' UTR 2a 155731 GLYCOGENIN (*Oryctolagus cuniculus*)
4. Hsa.36019 H27921 3' UTR 2a 162430 ATRIAL NATRIURETIC PEPTIDE RECEPTOR A PRECURSOR (*Homo sapiens*)
5. Hsa.301 U18934 gene 1 Human receptor tyrosine kinase (DTK) mRNA, complete cds.
6. Hsa.36694 D25217 gene 1 Human mRNA (KIAA0027) for ORF, partial cds.
7. Hsa.40177 H56686 3' UTR 2a 203961 GENOME POLYPROTEIN (Hog cholera virus)
8. Hsa.422 T64467 3' UTR 1 80480 P33477 ANNEXIN XI.
9. Hsa.2952 X72389 gene 1 *H. sapiens* mRNA for 4-hydroxyphenylpyruvate dioxygenase.
10. Hsa.3045 X66363 gene 1 SERINE/THREONINE-PROTEIN KINASE PCTAIRE-1 (HUMAN); contains MER22 repetitive element.
11. Hsa.3165 X68149 gene 1 *H. sapiens* BLR1 gene for Burkitt's lymphoma receptor 1.
12. Hsa.32319 R70253 3' UTR 2a 155165 GUANINE NUCLEOTIDE DISSOCIATION STIMULATOR RALGDSA (*Mus musculus*)
13. Hsa.37937 R87126 3' UTR 2a 197371 MYOSIN HEAVY CHAIN, NONMUSCLE (*Gallus gallus*)
14. Hsa.31933 R67343 3' UTR 2a 140965 IMMEDIATE-EARLY REGULATORY PROTEIN IE-N (*Autographa californica* nuclear polyhedrosis virus)
15. Hsa.36689 Z50753 gene 1 *H. sapiens* mRNA for GCAP-II/uroguanylin precursor.
16. Hsa.28186 H05910 3' UTR 2a 43545
17. Hsa.3138 D21239 gene 1 Human mRNA for C3G protein, complete cds.
18. Hsa.40595 H51015 3' UTR 2a 179925 PROTO-ONCOGENE DBL PRECURSOR (*Homo sapiens*)
19. Hsa.3271 X89416 gene 1 *H. sapiens* mRNA for protein phosphatase 5.
20. Hsa.33277 R80779 3' UTR 2a 146868 MIXED LINEAGE KINASE 1 (*Homo sapiens*)
21. Hsa.3048 X66362 gene 1 SERINE/THREONINE PROTEIN KINASE PCTAIRE-3 (HUMAN); contains Alu repetitive element.
22. Hsa.3072 X07948 gene 1 Human mRNA for transition protein 1 (TP1).
23. Hsa.307 L22214 gene 1 Human adenosine A1 receptor (ADORA1) mRNA exons 1-6, complete cds.
24. Hsa.3933 T97473 3' UTR 1 121460 MITOCHONDRIAL 2-OXOGLUTARATEIMALATE CARRIER PROTEIN (HUMAN).
25. Hsa.9246 T47383 3' UTR 2a 71046 ALKALINE PHOSPHATASE, PLACENTAL TYPE 1 PRECURSOR (*Homo sapiens*)
26. Hsa.3328 L42611 gene 1 *Homo sapiens* keratin 6 isoform K6e (KRT6E) mRNA, complete cds.
27. Hsa.3351 X15149 gene 1 Human mRNA for dystrophin isoform (partial).
28. Hsa.359 U09413 gene 1 Human zinc finger protein-ZNF135 mRNA, complete cds.
29. Hsa.32389 R70939 3' UTR2a 142680 TRANSCRIPTION FACTOR TAU 131 KD SUBUNIT (*Saccharomyces cerevisiae*)
30. Hsa.360 U09414 gene 1 Human zinc finger protein ZNF137 mRNA, complete cds.
31. Hsa.33576 H01418 3' UTR 2a 147382 SON OF SEVENLESS PROTEIN (*Drosophila melanogaster*)
32. Hsa.37818 H47650 3' UTR 2a 193667 PTS SYSTEM, SUCROSE-SPECIFIC IIABC COMPONENT (*Pediococcus pentosaceus*)
33. Hsa.35496 H22579 3' UTR 2a 159812 INTEGRIN ALPHA-6 PRECURSOR (*Homo sapiens*)
34. Hsa.36218 H29895 3' UTR 2a 190321 GUANINE NUCLEOTIDE-BINDING PROTEIN G(T) GAMMA-1 SUBUNIT (*Homo sapiens*)
35. Hsa.2943 Z15114 gene 1 *H. sapiens* mRNA for protein kinase C gamma (partial).
36. Hsa.3069 M37984 gene 1 Human slow twitch skeletal muscle/cardiac muscle troponin C gene, complete cds.
37. Hsa.37041 H45807 3' UTR 2a 188150 PROBABLE NUCLEAR ANTIGEN (Pseudorabies virus)
38. Hsa.37169 R83285 3' UTR 2a 194245 BUTYROPHILIN PRECURSOR (*Bos taurus*)
39. Hsa.40206 R99916 3' UTR 2a 201708 GENOME POLYPROTEIN (Human *rhinovirus* 89)
40. Hsa.28145 R56070 3' UTR 2a 40682 PLATELET-ACTIVATING FACTOR ACETYLHYDROLASE 45 KD SUBUNIT (*Homo sapiens*)
41. Hsa.31395 H06061 3' UTR 2a 43276 VOLTAGE-DEPENDENT ANION-SELECTIVE CHANNEL PROTEIN 1 (*Homo sapiens*)
42. Hsa.40009 R98441 3' UTR 2a 206999 GLYCOPHORIN E PRECURSOR (*Homo sapiens*)
43. Hsa.28895 R60508 3' UTR 2a 43155 CLEAVAGE STIMULATION FACTOR, 50 KD SUBUNIT (*Homo sapiens*)
44. Hsa.3182 X85786 gene 1 *H. sapiens* mRNA for DNA binding regulatory factor.
45. Hsa.35652 H23975 3' UTR 2a 159806 IG ALPHA-1 CHAIN C REGION (*Gorilla gorilla gorilla*)
46. Hsa.35652 H23975 3' UTR 2a 159806 IG ALPHA-1 CHAIN C REGION (*Gorilla gorilla gorilla*)
47. Hsa.34562 H11324 3' UTR 2a 47625 CELLULAR RETINALDEHYDE-BINDING PROTEIN (*Bos taurus*)
48. Hsa.28784 R59583 3' UTR 2a 41999 PRE-MRNA SPLICING FACTOR SRP75 (*Homo sapiens*)

49. Hsa.36354 H30734 3' UTR 2a 190187 RYANODINE RECEPTOR, SKELETAL MUSCLE (*Homo sapiens*)
50. Hsa.32730 H13194 3' UTR 2a 158868 ADP-RIBOSYLATION FACTOR-LIKE PROTEIN 2 (*Homo sapiens*)
51. Hsa.3274 L41268 gene 1 *Homo sapiens* natural killer-associated transcript 2 (NKAT2) mRNA, complete cds.
52. Hsa.33572 H01346 3' UTR 2a 147419 EUKARYOTIC INITIATION FACTOR 4 GAMMA (*Homo sapiens*)
53. Hsa.37192 R83349 3' UTR 2a 186603 EUKARYOTIC INITIATION FACTOR 4B (*Homo sapiens*)
54. Hsa.41189 X15943 gene 1 Human calcitonin/alpha-CGRP gene.
55. Hsa.3069 M37984 gene 1 Human slow twitch skeletal muscle/cardiac muscle troponin C gene, complete cds.
56. Hsa.3015 Z18948 gene 1 S-100E PROTEIN (HUMAN).
57. Hsa.1655 M77829 gene 1 Human channel-like integral membrane protein (CHIP28) mRNA, complete cds.
58. Hsa.2742 X07384 gene 1 Human mRNA for GLI protein.
59. Hsa.40957 H54091 3' UTR 2a 202915 CASEIN KINASE I HOMOLOG HHP2 (*Schizosaccharomyces pombe*)
60. Hsa.41163 U06088 gene 1 Human N-acetylgalactosamine 6-sulphatase (GALNS) gene, exon 14.

B.26 CG9

1. Hsa.1977 T51496 3' UTR 1 71488 60S RIBOSOMAL PROTEIN L37A (HUMAN).
2. Hsa.27685 R50158 3' UTR 2a 153229 MITOCHONDRIAL LON PROTEASE HOMOLOG PRECURSOR (*Homo sapiens*)
3. Hsa.2019 T51560 3' UTR 1 72227 40S RIBOSOMAL PROTEIN S16 (HUMAN).
4. Hsa.4689 T95018 3' UTR 2a 120032 40S RIBOSOMAL PROTEIN S18 (*Homo sapiens*)
5. Hsa.539 U14971 gene 1 Human ribosomal protein S9 mRNA, complete cds.
6. Hsa.3409 T53396 3' UTR 2a 68775 60S ACIDIC RIBOSOMAL PROTEIN P1 (*Polyorchis penicillatus*)
7. Hsa.1978 T72879 3' UTR 1 84299 60S RIBOSOMAL PROTEIN L7A (HUMAN).
8. Hsa.24464 H09263 3' UTR 2a 46514 ELONGATION FACTOR 1-ALPHA 1 (*Homo sapiens*)
9. Hsa.41126 K03460 gene 1 Human alpha-tubulin isotype H2-alpha gene, last exon.
10. Hsa.2597 T49423 3' UTR 1 67494 BREAST BASIC CONSERVED PROTEIN 1 (HUMAN).
11. Hsa.3004 H55933 3' UTR 1 203417 *H. sapiens* mRNA for homologue to yeast ribosomal protein L41.
12. Hsa.3006 T61602 3' UTR 1 78084 40S RIBOSOMAL PROTEIN S11 (HUMAN).
13. Hsa.3017 T95063 3' UTR 1 120122 40S RIBOSOMAL PROTEIN S26 (HUMAN).
14. Hsa.41124 M32405 gene 1 Human homologue of rat insulinoma gene (rig), exons 1-4.
15. Hsa.541 U14973 gene 1 Human ribosomal protein S29 mRNA, complete cds.
16. Hsa.36665 U31215 gene 1 Human metabotropic glutamate receptor 1 alpha (mGluR1alpha) mRNA, complete cds.
17. Hsa.2948 H54676 3' UTR 1 203220 60S RIBOSOMAL PROTEIN L18A (HUMAN).
18. Hsa.3094 H77302 3' UTR 1 233465 60S RIBOSOMAL PROTEIN (HUMAN).
19. Hsa.3835 H79852 3' UTR 2a 239944 60S ACIDIC RIBOSOMAL PROTEIN P2 (*Babesia bovis*)
20. Hsa.8583 R44770 3' UTR 2a 32991 METABOTROPIC GLUTAMATE RECEPTOR 2 PRECURSOR (*Rattus norvegicus*)
21. Hsa.73 R85464 3' UTR 1 179999 ATP SYNTHASE LIPID-BINDING PROTEIN P2 PRECURSOR (HUMAN).
22. Hsa.2440 T54341 3' UTR 1 69270 P25886 60S RIBOSOMAL PROTEIN L29.
23. Hsa.11232 T58645 3' UTR 2a 69351 P-SELECTIN PRECURSOR (*Homo sapiens*)
24. Hsa.1400 T63258 3' UTR 1 80068 ELONGATION FACTOR 1-ALPHA 1 (HUMAN).
25. Hsa.3409 T53396 3' UTR 2a 68775 60S ACIDIC RIBOSOMAL PROTEIN P1 (*Polyorchis penicillatus*)
26. Hsa.538 T56940 3' UTR 1 68306 P24050 40S RIBOSOMAL PROTEIN.
27. Hsa.15844 T80178 3' UTR 2a 115041 SERUM ALBUMIN PRECURSOR (*Homo sapiens*)
28. Hsa.30128 H49587 3' UTR 2a 178757 INTERFERON-INDUCED, DOUBLE-STRANDED RNA-ACTIVATED PROTEIN KINASE (*Homo sapiens*)
29. Hsa.3087 T65938 3' UTR 1 81639 TRANSLATIONALLY CONTROLLED TUMOR PROTEIN (HUMAN).
30. Hsa.35471 H46994 3' UTR 2a 178093 VERPROLIN (*Saccharomyces cerevisiae*)
31. Hsa.4252 T51529 3' UTR 2a 72384 ELONGATION FACTOR 1-DELTA (*Artemia salina*)
32. Hsa.489 T47144 3' UTR 1 74837 JN0549 RIBOSOMAL PROTEIN YL30.
33. Hsa.5398 T58861 3' UTR 2a 77563 60S RIBOSOMAL PROTEIN L30E (*Kluyveromyces lactis*)
34. Hsa.2221 T52015 3' UTR 1 72642 ELONGATION FACTOR 1-GAMMA (HUMAN).
35. Hsa.878 T61609 3' UTR 1 78081 LAMININ RECEPTOR (HUMAN).
36. Hsa.3002 R22197 3' UTR 1 130829 60S RIBOSOMAL PROTEIN L32 (HUMAN).
37. Hsa.823 M16937 gene 1 Human homeo box c1 protein, mRNA, complete cds.
38. Hsa.8068 T57619 3' UTR 2a 75437 40S RIBOSOMAL PROTEIN S6 (*Nicotiana tabacum*)
39. Hsa.20836 R02593 3' UTR 2a 124094 60S ACIDIC RIBOSOMAL PROTEIN P1 (*Polyorchis penicillatus*)
40. Hsa.20836 R02593 3' UTR 2a 124094 60S ACIDIC RIBOSOMAL PROTEIN P1 (*Polyorchis penicillatus*)
41. Hsa.121 R44884 3' UTR 1 33865 ADP,ATP CARRIER PROTEIN, LIVER ISOFORM T2 (HUMAN).
42. Hsa.1985 T52185 3' UTR 1 71940 P17074 40S RIBOSOMAL PROTEIN.
43. Hsa.5363 R01182 3' UTR 1 123748 60S RIBOSOMAL PROTEIN L38 (HUMAN).
44. Hsa.1216 M63959 gene 1 Human alpha-2-macroglobulin receptor-associated protein mRNA, complete cds.
45. Hsa.13702 T64983 3' UTR 2a 66854 TRANSFERRIN RECEPTOR PROTEIN (*Homo sapiens*)
46. Hsa.5392 T62947 3' UTR 2a 79366 60S RIBOSOMAL PROTEIN L24 (*Arabidopsis thaliana*)
47. Hsa.12260 R81170 3' UTR 2a 147439 TRANSLATIONALLY CONTROLLED TUMOR PROTEIN (*Homo sapiens*)
48. Hsa.9691 T49703 3' UTR 2a 67944 60S ACIDIC RIBOSOMAL PROTEIN P1 (*Polyorchis penicillatus*)
49. Hsa.153 T72503 3' UTR 1 82534 60S RIBOSOMAL PROTEIN L7 (HUMAN).
50. Hsa.1885 M62762 gene 1 VACUOLAR ATP SYNTHASE 16 KD PROTEOLIPID SUBUNIT (HUMAN).

51. Hsa.45499 H87344 3' UTR 2a 252396 SERUM ALBUMIN PRECURSOR (*Homo sapiens*)
52. Hsa.13183 T74257 3' UTR 2a 84713 ALKALINE PHOSPHATASE, PLACENTAL TYPE 1 PRECURSOR (*Homo sapiens*)
53. Hsa.44472 H80240 3' UTR 2a 240814 INTER-ALPHA-TRYPSIN INHIBITOR COMPLEX COMPONENT II PRECURSOR (*Homo sapiens*)
54. Hsa.44472 H80240 3' UTR 2a 240814 INTER-ALPHA-TRYPSIN INHIBITOR COMPLEX COMPONENT II PRECURSOR (*Homo sapiens*)
55. Hsa.2119 L08187 gene 1 Human cytokine receptor (EB13) mRNA, complete cds.
56. Hsa.364 U09848 gene 1 Human zinc finger protein (ZNF139) mRNA, partial cds.
57. Hsa.3174 X83412 gene 1 *H. sapiens* B1 mRNA for mucin.
58. Hsa.19249 T96832 3' UTR 2a 121265 INTERFERON-ALPHA RECEPTOR PRECURSOR (*Homo sapiens*)
59. Hsa.21339 R07007 3' UTR 2a 126689 RNA-BINDING PROTEIN FUS/TLS (*Homo sapiens*)
60. Hsa.652 M86553 gene 1 Human cathepsin S mRNA, complete cds.
61. Hsa.3056 X59871 gene 1 Human TCF-1 mRNA for T cell factor 1 (splice form C).
62. Hsa.45293 H86060 3' UTR 2a 222326 NEGATIVE FACTOR (Simian immunodeficiency virus)
63. Hsa.45222 H85596 3' UTR 2a 223220 CALCIUM/CALMODULIN-DEPENDENT PROTEIN KINASE TYPE II DELTA CHAIN (*Rattus norvegicus*)
64. Hsa.9304 T47645 3' UTR 2a 71309 GONADOTROPIN-RELEASING HORMONE RECEPTOR (*Homo sapiens*)
65. Hsa.13491 R39465 3' UTR 2a 23933 EUKARYOTIC INITIATION FACTOR 4A (*Oryctolagus cuniculus*)
66. Hsa.13491 R39465 3' UTR 2a 23933 EUKARYOTIC INITIATION FACTOR 4A (*Oryctolagus cuniculus*)
67. Hsa.44403 H79575 3' UTR 2a 239681 BOTULINUM NEUROTOXIN TYPE C1 PRECURSOR (*Clostridium botulinum*)
68. Hsa.45293 H86060 3' UTR 2a 222326 NEGATIVE FACTOR (Simian immunodeficiency virus)
69. Hsa.2950 Y00345 gene 1 Human mRNA for polyA binding protein.
70. Hsa.668 T65003 3' UTR 1 66879 P29316 60S RIBOSOMAL PROTEIN.
71. Hsa.1562 U15212 gene 1 Human caudal-type homeobox protein (CDX1) mRNA, partial cds.
72. Hsa.2800 X55715 gene 1 Human Hums3 mRNA for 40S ribosomal protein s3.
73. Hsa.286 T57483 3' UTR 1 75189 60S RIBOSOMAL PROTEIN L4 (HUMAN).
74. Hsa.5444 T48804 3' UTR 1 70269 40S RIBOSOMAL PROTEIN S24 (HUMAN).
75. Hsa.1422 M13450 gene 1 Human esterase D mRNA, 3'end.
76. Hsa.654 L33930 gene 1 *Homo sapiens* CD24 signal transducer mRNA, complete cds and 3' region.
77. Hsa.27721 R50505 3' UTR 2a 153149 60S ACIDIC RIBOSOMAL PROTEIN P1 (*Gallus gallus*)
78. Hsa.858 M25108 gene 1 Human integrin beta-3 subunit mRNA, 3' end.

B.27 CG10

1. Hsa.42186 H61410 3' UTR 2a 211590 PLATELET GLYCOPROTEIN IV (*Homo sapiens*)
2. Hsa.42949 H67764 3' UTR 2a 229939 ESTROGEN SULFOTRANSFERASE (*Bos taurus*)
3. Hsa.44067 H75867 3' UTR 2a 230561 ALPHA-1-ANTITRYPSIN PRECURSOR (*Homo sapiens*)
4. Hsa.1920 X06614 gene 1 Human mRNA for receptor of retinoic acid.
5. Hsa.41314 U31248 gene 1 Human zinc finger protein (ZNF174) mRNA, complete cds.
6. Hsa.447 U06698 gene 1 Human neuronal kinesin heavy chain mRNA, complete cds.
7. Hsa.231 X54163 gene 1 TROPONIN I, CARDIAC MUSCLE (HUMAN); contains element MER22 repetitive element.
8. Hsa.1920 X06614 gene 1 Human mRNA for receptor of retinoic acid.
9. Hsa.23699 R16665 3' UTR 2a 129642 ADENYLATE CYCLASE, TYPE V (*Canis familiaris*)
10. Hsa.6317 R39209 3' UTR 2a 23464 HUMAN IMMUNODEFICIENCY VIRUS TYPE I ENHANCER-BINDING PROTEIN 2 (*Homo sapiens*)
11. Hsa.6317 R39209 3' UTR 2a 23464 HUMAN IMMUNODEFICIENCY VIRUS TYPE I ENHANCER-BINDING PROTEIN 2 (*Homo sapiens*)
12. Hsa.41314 U31248 gene 1 Human zinc finger protein (ZNF174) mRNA, complete cds.
13. Hsa.1955 M83738 gene 1 Human protein-tyrosine phosphatase (PTPase MEG2) mRNA, complete cds.
14. Hsa.3020 X57830 gene 1 *H. sapiens* serotonin 5-HT2 receptor mRNA.
15. Hsa.732 M28129 gene 1 *Homo sapiens* eosinophil-derived neurotoxin (EDN) mRNA, complete cds.
16. Hsa.1373 K03192 gene 1 Human cytochrome P-450 mRNA, partial.
17. Hsa.1373 K03192 gene 1 Human cytochrome P-450 mRNA, partial.
18. Hsa.2626 X57110 gene 1 PROTO-ONCOGENE C-CBL (HUMAN); contains Alu repetitive element.
19. Hsa.10171 R70008 3' UTR 2a 142450 VASCULAR ENDOTHELIAL GROWTH FACTOR PRECURSOR (*Rattus norvegicus*)
20. Hsa.1147 M98326 gene 1 VALYL-TRNA SYNTHETASE (HUMAN).
21. Hsa.1670 M23419 gene1 INITIATION FACTOR 5A (HUMAN); contains element PTR5 repetitive element.
22. Hsa.168 U02493 gene 1 Human 54 kDa protein mRNA, complete cds.
23. Hsa.1774 X12876 gene 1 Human mRNA fragment for cytokeratin 18.
24. Hsa.1598 L38503 gene 1 *Homo sapiens* glutathione S-transferase theta 2 (GSTT2) mRNA, complete cds.
25. Hsa.2347 X51985 gene 1 Human LAG-3 mRNA for CD4-related protein involved in lymphocyte activation.
26. Hsa.2343 X53179 gene 1 Human mRNA for neuronal nicotinic acetylcholine receptor beta-2 subunit.
27. Hsa.1803 M29273 gene 1 MYELIN-ASSOCIATED GLYCOPROTEIN PRECURSOR (HUMAN).
28. Hsa.2610 X59511 gene 1 *H. sapiens* mRNA for beta-spectrin (3' partial).
29. Hsa.1454 M82919 gene 1 Human gamma amino butyric acid (GABAA) receptor beta-3 subunit mRNA, complete cds.
30. Hsa.16164 T81919 3' UTR 2a 109677 CREB-BINDING PROTEIN (*Mus musculus*)
31. Hsa.17091 T89175 3' UTR 2a 110022 G1/S-SPECIFIC CYCLIN D1 (*Homo sapiens*)

32. Hsa.17901 T89666 3' UTR 2a 116364 INTERLEUKIN-6 RECEPTOR BETA CHAIN PRECURSOR (*Homo sapiens*)
33. Hsa.41198 L49218 gene 1 *Homo sapiens* retinoblastoma susceptibility protein (RB1) E413K 1 bp deletion mutant (resulting in premature stop at amino acid 416) gene, exon 13 (L11910 bases 73717-73901).
34. Hsa.2410 L41067 gene 1 *Homo sapiens* NF-AT4c mRNA, complete cds.
35. Hsa.26747 R49169 3' UTR 2a 36905 HLA CLASS I HISTOCOMPATIBILITY ANTIGEN, C-4 ALPHA CHAIN (*Homo sapiens*)
36. Hsa.2008 M81758 gene 1 *Homo sapiens* skeletal muscle voltage-dependent sodium channel alpha subunit (SkM1) mRNA, complete cds.
37. Hsa.20164 R00285 3' UTR 2a 123267 PROTEIN KINASE CEK1 (*Schizosaccharomyces pombe*)
38. Hsa.22614 R37276 3' UTR 2a 25988 EUKARYOTIC INITIATION FACTOR 4 GAMMA (*Homo sapiens*)
39. Hsa.7700 R89067 3' UTR 2a 195723 KININOGEN, LMW PRECURSOR (*Homo sapiens*)
40. Hsa.11340 T59354 3' UTR 2a 75292 EBNA-2 NUCLEAR PROTEIN (Epstein-barr virus)
41. Hsa.41083 D00749 gene 1 Human T cell surface antigen CD7 gene, exon 4.
42. Hsa.1079 M64231 gene 1 Human spermidine synthase gene, complete cds.
43. Hsa.17213 R35903 3' UTR 2a 137063 INTERLEUKIN-1 RECEPTOR, TYPE II PRECURSOR (*Mus musculus*)
44. Hsa.23677 R16543 3' UTR 2a 129600 PROBABLE NUCLEAR ANTIGEN (Pseudorabies virus)
45. Hsa.26698 R48936 3' UTR 2a 36885 GLYCOPROTEIN VP7 (Chicken rotavirus a)
46. Hsa.27738 H21532 3' UTR 2a 159978 RETINOIC ACID RECEPTOR ALPHA-1 (*Homo sapiens*)
47. Hsa.14896 T71207 3' UTR 2a 110162 RAS-RELATED C3 BOTULINUM TOXIN SUBSTRATE 2 (*Homo sapiens*)
48. Hsa.2618 X67699 gene 1 *H. sapiens* HE5 mRNA for CDw52 antigen.
49. Hsa.22461 R36973 3' UTR 2a 25940 IRON-RESPONSIVE ELEMENT BINDING PROTEIN (*Oryctolagus cuniculus*)
50. Hsa.2309 Y00796 gene 1 Human mRNA for leukocyte-associated molecule-1 alpha subunit (LFA-1 alpha subunit).
51. Hsa.10784 T56350 3' UTR 2a 73066 NUCLEOLIN (*Rattus norvegicus*)
52. Hsa.36161 H29546 3' UTR 2a 52669 NEUROTENSIN RECEPTOR (*Homo sapiens*)
53. Hsa.638 L06111 gene 1 Human L-type voltage-gated calcium channel B subunit mRNA for isoform b, complete cds.
54. Hsa20883 R05291 3' UTR 2a 125114 SEROTRANSFERRIN PRECURSOR (*Homo sapiens*)
55. Hsa.2191 T40645 3' UTR 1 60737 Human Wiskott-Aldrich syndrome (WAS) mRNA, complete cds.
56. Hsa.1860 M65105 gene 1 SODIUM-DEPENDENT NORADRENALINE TRANSPORTER (HUMAN); contains Alu repetitive element.
57. Hsa.2084 M63239 gene 1 Human tyrosinase gene, exon 5.
58. Hsa.5122 X05196 gene 1 Human aldolase C gene.
59. Hsa.12754 T67921 3' UTR 1 81975 ASIALOGLYCOPROTEIN RECEPTOR R2/3 (*Rattus norvegicus*)
60. Hsa.24290 R44072 3' UTR 2a 33503 XYLOSE REPRESSOR (*Bacillus subtilis*)
61. Hsa.2486 D14695 gene 1 Human mRNA (KIAA0025) for ORF (complete cds) and PIGHEP3 homologous region.
62. Hsa.3132 U11037 gene 1 Human Ibd2 mRNA, complete cds.

B.28 CG11
1. Hsa.3118 M55543 gene 1 INTERFERON-INDUCED GUANYLATE-BINDING PROTEIN 2 (HUMAN).
2. Hsa.919 H66976 3' UTR 1 212229 HLA CLASS II HISTOCOMPATIBILITY ANTIGEN, DP(1) ALPHA CHAIN (HUMAN).
3. Hsa.39809 R98189 3' UTR 2a 200776 HLA CLASS II HISTOCOMPATIBILITY ANTIGEN, GAMMA CHAIN PRECURSOR (*Homo sapiens*)
4. Hsa.818 X02228 gene 1 Human HLA-DP-beta 1 gene and HLA-DP-alpha-1 gene exon 1.
5. Hsa.918 K01144 gene 1 Human major histocompatibility class II antigen gamma chain mRNA, complete cds.
6. Hsa.35955 H26965 3' UTR 2a 182171 HLA CLASS II HISTOCOMPATIBILITY ANTIGEN, GAMMA CHAIN PRECURSOR (*Homo sapiens*)
7. Hsa.5514 M13560 gene 1 Human Ia-associated invariant gamma-chain gene, exon 8, clones lambda-y(1,2,3).
8. Hsa.25142 R71401 3' UTR 2a 155096 HEMOGLOBIN ALPHA-1, ALPHA-2, AND ALPHA-3 CHAINS (*Macaca assamenses*)
9. Hsa.3105 X04011 gene 1 Human mRNA of X-CGD gene involved in chronic granulomatous disease located on chromosome X.
10. Hsa.914 V00523 gene 1 Human mRNA for histocompatibility antigen HLA-DR (fragment). The alpha chain.
11. Hsa.1825 T62633 3' UTR 1 79623 HLA CLASS II HISTOCOMPATIBILITY ANTIGEN, DR-1 BETA CHAIN (HUMAN).
12. Hsa.916 V00522 gene 1 Human mRNA encoding major histocompatibility complex gene HLA-DR beta-1.
13. Hsa.1829 X00700 gene 1 Human mRNA fragment for class II histocompatibility antigen beta-chain (pII-beta-4).
14. Hsa.41357 M27635 gene 1 *Homo sapiens* MHC HLA-DRw12 allele mRNA, beta-1 chain, complete cds.
15. Hsa.912 X03068 gene 1 Human mRNA for HLA-D class II antigen DQw1.1 beta chain.
16. Hsa.10358 T53694 3' UTR 2a 69762 COMPLEMENT C1Q SUBCOMPONENT, A CHAIN PRECURSOR (*Homo sapiens*)
17. Hsa.1220 X14618 gene 1 Human mRNA for acid phosphatase type 5 (EC 3.1.3.2).
18. Hsa.767 J04162 gene 1 Human leukocyte IgG receptor (Fc-gamma-R) mRNA, complete cds.
19. Hsa.1260 M10065 gene 1 Human apolipoprotein E (epsilon-4 allele) gene, complete cds.
20. Hsa.847 R73660 3' UTR 1 143143 GAMMA-INTERFERON-INDUCIBLE PROTEIN IP-30 PRECURSOR (HUMAN).
21. Hsa.855 L25851 gene 1 INTEGRIN ALPHA-E PRECURSOR (HUMAN); contains Alu repetitive element.
22. Hsa.36897 H42884 3' UTR 2a 183086 INTERFERON REGULATORY FACTOR 1 (*Homo sapiens*)
23. Hsa.504 Z22936 gene 1 *H. sapiens* TAP2E mRNA, complete CDS.

24. Hsa.10510 T54650 3' UTR 2a 73757 HLA CLASS I HISTOCOMPATIBILITY ANTIGEN, F ALPHA CHAIN PRECURSOR (*Homo sapiens*)
25. Hsa.10706 R42244 3' UTR1 30543 ANTIGEN PEPTIDE TRANSPORTER 1 (HUMAN).
26. Hsa.12209 H65182 3' UTR 2a 238736 SIGNAL TRANSDUCER AND ACTIVATOR OF TRANSCRIPTION 1-ALPHA/BETA (*Homo sapiens*)
27. Hsa.1567 T54276 3' UTR 1 69195 PROTEASOME COMPONENT C13 (HUMAN).
28. Hsa.268 R09400 3' UTR 1 127605 S39423 PROTEIN I-5111, INTERFERON-GAMMA-INDUCED.
29. Hsa.1917 L27841 gene 1 Human autoantigen pericentriol material 1 (PCM-1) mRNA, complete cds.
30. Hsa.2192 U14391 gene 1 Human myosin-IC mRNA, complete cds.
31. Hsa.2209 M59819 gene 1 Human granulocyte colony-stimulating factor receptor (G-CSFR-2) mRNA, complete cds.
32. Hsa.41442 H56077 3' UTR 2a 203750 GTP CYCLOHYDROLASE I (*Homo sapiens*)
33. Hsa.9174 D28137 gene 1 Human mRNA for BST-2, complete cds.
34. Hsa.949 M59807 gene 1 NATURAL KILLER CELLS PROTEIN 4 PRECURSOR (HUMAN); contains element MSR1 repetitive element.

B.29 CG12
1. Hsa.1977 T51496 3' UTR 1 71488 60S RIBOSOMAL PROTEIN L37A (HUMAN).
2. Hsa.27685 R50158 3' UTR 2a 153229 MITOCHONDRIAL LON PROTEASE HOMOLOG PRECURSOR (*Homo sapiens*)
3. Hsa.2019 T51560 3' UTR 1 72227 40S RIBOSOMAL PROTEIN S16 (HUMAN).
4. Hsa.4689 T95018 3' UTR 2a 120032 40S RIBOSOMAL PROTEIN S18 (*Homo sapiens*)
5. Hsa.539 U14971 gene 1 Human ribosomal protein S9 mRNA, complete cds.
6. Hsa.3409 T53396 3' UTR 2a 68775 60S ACIDIC RIBOSOMAL PROTEIN P1 (*Polyorchis penicillatus*)
7. Hsa.1978 T72879 3' UTR 1 84299 60S RIBOSOMAL PROTEIN L7A (HUMAN).
8. Hsa.24464 H09263 3' UTR 2a 46514 ELONGATION FACTOR 1-ALPHA 1 (*Homo sapiens*)
9. Hsa.41126 K03460 gene 1 Human alpha-tubulin isotype H2-alpha gene, last exon.
10. Hsa.2597 T49423 3' UTR 1 67494 BREAST BASIC CONSERVED PROTEIN 1 (HUMAN).
11. Hsa.3004 H55933 3' UTR 1 203417 *H. sapiens* mRNA for homologue to yeast ribosomal protein L41.
12. Hsa.3006 T61602 3' UTR 1 78084 40S RIBOSOMAL PROTEIN S11 (HUMAN).
13. Hsa.3017 T95063 3' UTR 1 120122 40S RIBOSOMAL PROTEIN S26 (HUMAN).
14. Hsa.41124 M32405 gene 1 Human homologue of rat insulinoma gene (rig), exons 1-4.
15. Hsa.541 U14973 gene 1 Human ribosomal protein S29 mRNA, complete cds.
16. Hsa.36665 U31215 gene 1 Human metabotropic glutamate receptor 1 alpha (mGluR 1 alpha) mRNA, complete cds.
17. Hsa.2948 H54676 3' UTR 1 203220 60S RIBOSOMAL PROTEIN L18A (HUMAN).
18. Hsa.3094 H77302 3' UTR 1 233465 60S RIBOSOMAL PROTEIN (HUMAN).
19. Hsa.3835 H79852 3' UTR 2a 239944 60S ACIDIC RIBOSOMAL PROTEIN P2 (*Babesia bovis*)
20. Hsa.8583 R44770 3' UTR 2a 32991 METABOTROPIC GLUTAMATE RECEPTOR 2 PRECURSOR (*Rattus norvegicus*)
21. Hsa.73 R85464 3' UTR 1 179999 ATP SYNTHASE LIPID-BINDING PROTEIN P2 PRECURSOR (HUMAN).
22. Hsa.2440 T54341 3' UTR 1 69270 P25886 60S RIBOSOMAL PROTEIN L29.
23. Hsa.11232 T58645 3' UTR 2a 69351 P-SELECTIN PRECURSOR (*Homo sapiens*)
24. Hsa.1400 T63258 3' UTR 1 80068 ELONGATION FACTOR 1-ALPHA 1 (HUMAN).
25. Hsa.3409 T53396 3' UTR 2a 68775 60S ACIDIC RIBOSOMAL PROTEIN P1 (*Polyorchis penicillatus*)
26. Hsa.538 T56940 3' UTR 1 68306 P24050 40S RIBOSOMAL PROTEIN.
27. Hsa.15844 T80178 3' UTR 2a 115041 SERUM ALBUMIN PRECURSOR (*Homo sapiens*)
28. Hsa.30128 H49587 3' UTR 2a 178757 INTERFERON-INDUCED, DOUBLE-STRANDED RNA-ACTIVATED PROTEIN KINASE (*Homo sapiens*)
29. Hsa.3087 T65938 3' UTR 1 81639 TRANSLATIONALLY CONTROLLED TUMOR PROTEIN (HUMAN).
30. Hsa.35471 H46994 3' UTR 2a 178093 VERPROLIN (*Saccharomyces cerevisiae*)
31. Hsa.4252 T51529 3' UTR 2a 72384 ELONGATION FACTOR 1-DELTA (*Artemia salina*)
32. Hsa.489 T47144 3' UTR 1 74837 JN0549 RIBOSOMAL PROTEIN YL30.
33. Hsa.5398 T58861 3' UTR 2a 77563 60S RIBOSOMAL PROTEIN L30E (*Kluyveromyces lactis*)
34. Hsa.2221 T52015 3' UTR 1 72642 ELONGATION FACTOR 1-GAMMA (HUMAN).
35. Hsa.878 T61609 3' UTR 1 78081 LAMININ RECEPTOR (HUMAN).
36. Hsa.3002 R22197 3' UTR 1 130829 60S RIBOSOMAL PROTEIN L32 (HUMAN).
37. Hsa.823 M16937 gene 1 Human homeo box c1 protein, mRNA, complete cds.
38. Hsa.8068 T57619 3' UTR 2a 75437 40S RIBOSOMAL PROTEIN S6 (*Nicotiana tabacum*)
39. Hsa.20836 R02593 3' UTR 2a 124094 60S ACIDIC RIBOSOMAL PROTEIN P1 (*Polyorchis penicillatus*)
40. Hsa.20836 R02593 3' UTR 2a 124094 60S ACIDIC RIBOSOMAL PROTEIN P1 (*Polyorchis penicillatus*)
41. Hsa.1121 R44884 3' UTR 1 33865 ADP, ATP CARRIER PROTEIN, LIVER ISOFORM T2 (HUMAN).
42. Hsa.1985 T52185 3' UTR 1 71940 P17074 40S RIBOSOMAL PROTEIN.
43. Hsa.5363 R01182 3' UTR 1 123748 60S RIBOSOMAL PROTEIN L38 (HUMAN).
44. Hsa.1216 M63959 gene 1 Human alpha-2-macroglobulin receptor-associated protein mRNA, complete cds.
45. Hsa.13702 T64983 3' UTR 2a 66854 TRANSFERRIN RECEPTOR PROTEIN (*Homo sapiens*)
46. Hsa.5392 T62947 3' UTR 2a 79366 60S RIBOSOMAL PROTEIN L24 (*Arabidopsis thaliana*)
47. Hsa.12260 R81170 3' UTR 2a 147439 TRANSLATIONALLY CONTROLLED TUMOR PROTEIN (*Homo sapiens*)
48. Hsa.9691 T49703 3' UTR 2a 67944 60S ACIDIC RIBOSOMAL PROTEIN P1 (*Polyorchis penicillatus*)
49. Hsa.153 T72503 3' UTR 1 82534 60S RIBOSOMAL PROTEIN L7 (HUMAN).

50. Hsa.1885 M62762 gene 1 VACUOLAR ATP SYNTHASE 16 KD PROTEOLIPID SUBUNIT (HUMAN).
51. Hsa.45499 H87344 3' UTR 2a 252396 SERUM ALBUMIN PRECURSOR (*Homo sapiens*)

B.30 CG13
1. Hsa.13183 T74257 3' UTR 2a 84713 ALKALINE PHOSPHATASE, PLACENTAL TYPE 1 PRECURSOR (*Homo sapiens*)
2. Hsa.44472 H80240 3' UTR 2a 240814 INTER-ALPHA-TRYPSIN INHIBITOR COMPLEX COMPONENT II PRECURSOR (*Homo sapiens*)
3. Hsa.44472 H80240 3' UTR 2a 240814 INTER-ALPHA-TRYPSIN INHIBITOR COMPLEX COMPONENT II PRECURSOR (*Homo sapiens*)
4. Hsa.2119 L08187 gene 1 Human cytokine receptor (EB13) mRNA, complete cds.
5. Hsa.364 U09848 gene 1 Human zinc finger protein (ZNF139) mRNA, partial cds.
6. Hsa.3174 X83412 gene 1 *H. sapiens* B1 mRNA for mucin.
7. Hsa.19249 T96832 3' UTR2a 121265 INTERFERON-ALPHA RECEPTOR PRECURSOR (*Homo sapiens*)
8. Hsa.21339 R07007 3' UTR 2a 126689 RNA-BINDING PROTEIN FUS/TLS (*Homo sapiens*)
9. Hsa.652 M86553 gene 1 Human cathepsin S mRNA, complete cds.
10. Hsa.3056 X59871 gene 1 Human TCF-1 mRNA for T cell factor 1 (splice form C).
11. Hsa.45293 H86060 3' UTR 2a 222326 NEGATIVE FACTOR (Simian immunodeficiency virus)
12. Hsa.45222 H85596 3' UTR 2a 223220 CALCIUM/CALMODULIN-DEPENDENT PROTEIN KINASE TYPE II DELTA CHAIN (*Rattus norvegicus*)
13. Hsa.9304 T47645 3' UTR 2a 71309 GONADOTROPIN-RELEASING HORMONE RECEPTOR (*Homo sapiens*)
14. Hsa.13491 R39465 3' UTR 2a 23933 EUKARYOTIC INITIATION FACTOR 4A (*Oryctolagus cuniculus*)
15. Hsa.13491 R39465 3' UTR 2a 23933 EUKARYOTIC INITIATION FACTOR 4A (*Oryctolagus cuniculus*)
16. Hsa.44403 H79575 3' UTR 2a 239681 BOTULINUM NEUROTOXIN TYPE C1 PRECURSOR (*Clostridium botulinum*)
17. Hsa.45293 H86060 3' UTR 2a 222326 NEGATIVE FACTOR (Simian immunodeficiency virus)

B.31 CG14
1. Hsa.1400 T63258 3' UTR 1 80068 ELONGATION FACTOR 1-ALPHA 1 (HUMAN).
2. Hsa.3409 T53396 3' UTR 2a 68775 60S ACIDIC RIBOSOMAL PROTEIN P1 (*Polyorchis penicillatus*)
3. Hsa.538 T56940 3' UTR 1 68306 P24050 40S RIBOSOMAL PROTEIN.
4. Hsa.15844 T80178 3' UTR 2a 115041 SERUM ALBUMIN PRECURSOR (*Homo sapiens*)
5. Hsa.30128 H49587 3' UTR 2a 178757 INTERFERON-INDUCED, DOUBLE-STRANDED RNA-ACTIVATED PROTEIN KINASE (*Homo sapiens*)
6. Hsa.3087 T65938 3' UTR 1 81639 TRANSLATIONALLY CONTROLLED TUMOR PROTEIN (HUMAN).
7. Hsa.35471 H46994 3' UTR 2a 178093 VERPROLIN (*Saccharomyces cerevisiae*)
8. Hsa.4252 T51529 3' UTR 2a 72384 ELONGATION FACTOR 1-DELTA (*Artemia salina*)
9. Hsa.489 T47144 3' UTR 1 74837 JN0549 RIBOSOMAL PROTEIN YL30.
10. Hsa.5398 T58861 3' UTR 2a 77563 60S RIBOSOMAL PROTEIN L30E (*Kluyveromyces lactis*)
11. Hsa.2221 T52015 3' UTR 1 72642 ELONGATION FACTOR 1-GAMMA (HUMAN).
12. Hsa.878 T61609 3' UTR 1 78081 LAMININ RECEPTOR (HUMAN).
13. Hsa.3002 R22197 3' UTR 1 130829 60S RIBOSOMAL PROTEIN L32 (HUMAN).
14. Hsa.823 M16937 gene 1 Human homeo box c1 protein, mRNA, complete cds.
15. Hsa.8068 T57619 3' UTR 2a 75437 40S RIBOSOMAL PROTEIN S6 (*Nicotiana tabacum*)
16. Hsa.20836 R02593 3' UTR 2a 124094 60S ACIDIC RIBOSOMAL PROTEIN P1 (*Polyorchis penicillatus*)
17. Hsa.20836 R02593 3' UTR 2a 124094 60S ACIDIC RIBOSOMAL PROTEIN P1 (*Polyorchis penicillatus*)
18. Hsa.1121 R44884 3' UTR 1 33865 ADP, ATP CARRIER PROTEIN, LIVER ISOFORM T2 (HUMAN).
19. Hsa.1985 T52185 3' UTR 1 71940 P17074 40S RIBOSOMAL PROTEIN.
20. Hsa.5363 R01182 3' UTR 1 123748 60S RIBOSOMAL PROTEIN L38 (HUMAN).
21. Hsa.1216 M63959 gene 1 Human alpha-2-macroglobulin receptor-associated protein mRNA, complete cds.
22. Hsa.13702 T64983 3' UTR 2a 66854 TRANSFERRIN RECEPTOR PROTEIN (*Homo sapiens*)
23. Hsa.5392 T62947 3' UTR 2a 79366 60S RIBOSOMAL PROTEIN L24 (*Arabidopsis thaliana*)
24. Hsa.12260 R81170 3' UTR 2a 147439 TRANSLATIONALLY CONTROLLED TUMOR PROTEIN (*Homo sapiens*)
25. Hsa.9691 T49703 3' UTR 2a 67944 60S ACIDIC RIBOSOMAL PROTEIN P1 (*Polyorchis penicillatus*)
26. Hsa.153 T72503 3' UTR 1 82534 60S RIBOSOMAL PROTEIN L7 (HUMAN).
27. Hsa.1885 M62762 gene 1 VACUOLAR ATP SYNTHASE 16 KD PROTEOLIPID SUBUNIT (HUMAN).
28. Hsa.45499 H87344 3' UTR 2a 252396 SERUM ALBUMIN PRECURSOR (*Homo sapiens*)
29. Hsa.13183 T74257 3' UTR 2a 84713 ALKALINE PHOSPHATASE, PLACENTAL TYPE 1 PRECURSOR (*Homo sapiens*)
30. Hsa.44472 H80240 3' UTR 2a 240814 INTER-ALPHA-TRYPSIN INHIBITOR COMPLEX COMPONENT II PRECURSOR (*Homo sapiens*)
31. Hsa.44472 H80240 3' UTR 2a 240814 INTER-ALPHA-TRYPSIN INHIBITOR COMPLEX COMPONENT II PRECURSOR (*Homo sapiens*)
32. Hsa.2119 L08187 gene 1 Human cytokine receptor (EB13) mRNA, complete cds.
33. Hsa.364 U09848 gene 1 Human zinc finger protein (ZNF139) mRNA, partial cds.
34. Hsa.3174 X83412 gene 1 *H. sapiens* B1 mRNA for mucin.

B.32 CG15
1. Hsa.262 M69043 gene 1 MAJOR HISTOCOMPATIBILITY COMPLEX ENHANCER-BINDING PROTEIN (HUMAN).
2. Hsa.3307 U28963 gene 1 Human Gps2 (GPS2) mRNA, complete cds.
3. Hsa.542 L14848 gene 1 Human MHC class I-related protein mRNA, complete cds.
4. Hsa.44244 H78386 3' UTR 2a 233583 INTERLEUKIN-1 RECEPTOR, TYPE II PRECURSOR (*Homo sapiens*)

5. Hsa.11096 T57882 3' UTR 2a 71636 MYOSIN HEAVY CHAIN, NONMUSCLE TYPE A (*Homo sapiens*)
6. Hsa.43431 H68239 3' UTR 2a 239077 SUPPRESSOR OF HAIRY WING PROTEIN (*Drosophila virilis*)
7. Hsa.692 M76378 gene 1 Human cysteine-rich protein (CRP) gene, exons 5 and 6.
8. Hsa.1000 M95678 gene 1 *Homo sapiens* phospholipase C-beta-2 mRNA, complete cds.
9. Hsa.1768 M63509 gene 1 Human glutathione transferase M2 (GSTM2) mRNA, complete cds.
10. Hsa.17514 X89985 gene 1 *H. sapiens* mRNA for BCL7B protein.
11. Hsa.2706 X02761 gene 1 Human mRNA for fibronectin (FN precursor).
12. Hsa.964 R39130 3' UTR 1 26585 S27965 HYPOTHETICAL PROTEIN.
13. Hsa.1610 M96233 gene 1 Human glutathione transferase class mu number 4 (GSTM4) gene, complete cds.
14. Hsa.18321 R44887 3' UTR 2a 33869 NEDD5 PROTEIN (*Mus musculus*)
15. Hsa.13110 T72403 3' UTR2a 86225 HLA CLASS II HISTOCOMPATIBILITY ANTIGEN, DQ(3) ALPHA CHAIN PRECURSOR (*Homo sapiens*)
16. Hsa.1175 U13896 gene 1 Human homolog of *Drosophila* discs large protein, isoform 2 (hdlg-2) mRNA, complete cds.
17. Hsa.1516 J04621 gene 1 SYNDECAN-2 PRECURSOR (HUMAN); contains Alu repetitive element.
18. Hsa.1558 R70016 3' UTR 1 142466 Human F-actin capping protein beta subunit mRNA, complete cds.
19. Hsa.19003 Z46389 gene 1 *Homo sapiens* encoding vasodilator-stimulated phosphoprotein (VASP).
20. Hsa.1902 L05144 gene 1 PHOSPHOENOLPYRUVATE CARBOXYKINASE, CYTOSOLIC (HUMAN); contains Alu repetitive element; contains element PTR5 repetitive element.
21. Hsa.2342 X80754 gene 1 *H. sapiens* mRNA for GTP-binding protein.
22. Hsa.114 L10717 gene 1 TYROSINE-PROTEIN KINASE LYK (HUMAN); contains Alu repetitive element.
23. Hsa.4234 H05070 3' UTR 2a 43401 DNA-BINDING PROTEIN 65 (Bacteriophage t4)
24. Hsa.13670 T64941 3' UTR 2a 66800 SERINE PROTEASE HEPSIN (*Homo sapiens*)
25. Hsa.1664 U28389 gene 1 Human dematin 52 kDa subunit mRNA, complete cds.
26. Hsa.2858 Z25821 gene 1 *H. sapiens* gene for mitochondrial dodecenoyl-CoA delta-isomerase, exons 1 and 2.
27. Hsa.3129 L38696 gene 1 *Homo sapiens* autoantigen p542 mRNA, 3' end of cds.

B.33 CG16
1. Hsa.2818 Z25521 gene 1 *H. sapiens* integrin associated protein mRNA, complete CDS.
2. Hsa.8781 T40454 3' UTR 2a 60221 ANTIGENIC SURFACE DETERMINANT PROTEIN OA3 PRECURSOR (*Homo sapiens*)
3. Hsa.123 T65790 3' UTR 1 80410 FARNESYL PYROPHOSPHATE SYNTHETASE (HUMAN).
4. Hsa.275 L10413 gene 1 Human farnesyltransferase alpha-subunit mRNA, complete cds.
5. Hsa.21379 H272023' UTR 2a 158347 ADENOVIRUS E1A ENHANCER BINDING PROTEIN (*Homo sapiens*)
6. Hsa.6619 R38736 3' UTR 2a 24761 HYPOTHETICAL TRP-ASP REPEATS CONTAINING PROTEIN IN SSC3-ERS1 INTERGENIC REGION (*Saccharomyces cerevisiae*)
7. Hsa.26083 R27813 3' UTR 2a 134592 EBV-INDUCED G PROTEIN-COUPLED RECEPTOR 2 (*Homo sapiens*)
8. Hsa.6030 H72965 3' UTR 2a 213942 26S PROTEASE REGULATORY SUBUNIT 7 (*Homo sapiens*)
9. Hsa.2904 Z29505 gene 1 *H. sapiens* mRNA for nucleic acid binding protein sub2.3.
10. Hsa.3010 Z29677 gene 1 *H. sapiens* mRNA for ras-related GTP-binding protein.
11. Hsa.2756 X17644 gene 1 Human GST1-Hs mRNA for GTP-binding protein.
12. Hsa.320 M93009 gene 1 Human L-isoaspartyl/D-aspartyl protein carboxyl methyltransferase isozyme I, mRNA, 3' end.
13. Hsa.17130 U24105 gene 1 Human coatomer protein (HEPCOP) mRNA, complete cds.
14. Hsa.21660 R52271 3' UTR 2a 154410 OUTER MEMBRANE USHER PROTEIN PAPC PRECURSOR (*Escherichia coli*)
15. Hsa.20524 R01157 3' UTR 2a 124858 HLA CLASS I HISTOCOMPATIBILITY ANTIGEN, C-4 ALPHA CHAIN (*Homo sapiens*)
16. Hsa.19001 R94513 3' UTR 2a 197667 SIGNAL TRANSDUCER AND ACTIVATOR OF TRANSCRIPTION 2 (*Homo sapiens*)
17. Hsa.2484 D14689 gene 1 Human mRNA for ORF, complete cds.
18. Hsa.3876 R37114 3' UTR 2a 26050 PROBABLE SERINE/THREONINE-PROTEIN KINASE YHR102W (*Saccharomyces cerevisiae*)
19. Hsa.42382 H62885 3' UTR 2a 205685 CCAAT/ENHANCER BINDING PROTEIN BETA (*Homo sapiens*)
20. Hsa.634 L34059 gene 1 NEURAL-CADHERIN PRECURSOR (HUMAN).
21. Hsa.2154 U13991 gene 1 Human TATA-binding protein associated factor 30 kDa subunit (tafII30) mRNA, complete cds.
22. Hsa.1088 X69141 gene 1 *H. sapiens* mRNA for squalene synthase.
23. Hsa.3254 X74795 gene 1 *H. sapiens* P1-Cdc46 mRNA.
24. Hsa.1192 D38549 gene 1 Human mRNA (KIAA0068) for ORF, partial cds.
25. Hsa.2436 H80114 3' UTR 1 233334 Human nuclear localization sequence receptor hSRP1alpha mRNA, complete cds.

REFERENCES

1. D. J. Lockhart, H. Dong, M. C. Byrne et al.: Expression monitoring by hybridization to high-density oligonucleotide arrays. *Nat. Biotech.*, 14:1675-1680, 1996.
2. J. L. DeRisi, V R Iyer and P O Brown. Exploring the metabolic and genetic control of gene expression on a genomic scale. *Science*, 278:680-686, 1997.
3. U. Alon et al. Broad patterns of gene expression revealed by clustering analysis of tumor and normal colon tissues probed by oligonucleotide arrays. *PNAS*, 96:6745-6750, 1999.
4. M. B. Eisen et al. Cluster analysis and display of genome-wide expression patterns. *PNAS*, 95:14683-14868, 1998.

5. T. R. Golub et al. Molecular classification of cancer: Class discovery and class prediction by gene expression monitoring. *Science,* 286:531-537, 1999.
6. C. M. Perou et al. Distinctive gene expression patterns in human mammary epithelial cells and breast cancers. *PNAS,* 96:9212-9217, 1999.
7. E. S. Lander. Array of hope. *Nature Genetics,* 21:3-4, 1999.
8. M. Q. Zhang. Promoter analysis of co-regulated genes in the yeast genome. *Comput. Chem.,* 23:233-250, 1999.
9. M. Blatt et al. Super-paramagnetic clustering of data. *Physical Review Letters,* 76:3251-3255, 1996
10. E. Domany. Super-paramagnetic clustering of data-the definitive solution of an ill-posed problem. *Physica A,* 263:158, 1999.
11. G. Getz et al. Super-paramagnetic clustering of yeast gene expression profiles. Physica A279: 457-464, 2000
12. U.S. Pat. No. 6,021,383
13. B. Alberts et al. *Molecular biology of the cell*. Garland Publishing, New York, N.Y., USA, 1994.
14. P W Wadsworth and J G Bryan. *Introduction to Probability and Random Variables*. McGraw-Hill, New York, 1960.
15. T. M. Cover and J. A. Thomas. *Elements of Information Theory*. Wiley-Interscience, New York, 1991.
16. G. Getz et al. Coupled two way clustering of gene microarray data. *PNAS* 97:12079-12084, 2000.
17. M. Blatt et al. Super-paramagnetic clustering of data. *Physical Review Letters,* 76:3251-3255, 1996.
18. M. Blatt et al. Data clustering using a model granular magnet. *Neural Computation,* 9:1805-1842, 1997.
19. S. Wang and R H Swendsen. Cluster monte-carlo algorithms. *Physica A.,* 167:565-579, 1990
20. M. Schena et al. Parallel human genome analysis: microarray-based expression monitoring of 1000 genes. *PNAS,* 93:10614-10619, 1996.
21. Molecular pattern recognition Web site: *http://waldo.wi.mit.edu/mpr*
22. A K Jain and R C Dubes. *Algorithms for clustering data*. Prentice-Hall, Englewood Cliffs, 1998.
23. Web site of the Department of Molecular Biology, Princeton University: *http://molbio.princeton.edu/colondata*.
24. U. Alon et al., private communication.

What is claimed is:

1. A method for analyzing data, available in the form of an array of numbers stored electronically as a data structure, wherein each row of the array represents measurements of the values taken by a particular attribute over several samples and each column represents the measurements of the various attributes taken for a particular sample for the analysis of gene expression data taken from several tissues, wherein the attributes are different genes for which expression levels were measured and the samples are human tissues or other biological material for which the expression levels of the genes have been determined, the method performed on an electronic processor, the method comprising:

measuring gene expression levels on a microarray to obtain said array of numbers;

performing cluster analysis of said electronically stored numbers of said data structure in two ways, one way being in a gene dimension and a second way being in a sample dimension, over the samples and over the genes respectively, wherein the two ways of clustering are coupled: such that each cluster of genes is configured as a clustering configuration for clustering any group of samples, and each group of samples is configured as a clustering configuration for clustering any group of genes, repeating said cluster analysis iteratively to achieve stable clusters, and whenever stable clusters are generated, then using said stable clusters as additional clustering configurations to further search for additional clusters in the other dimension, and outputting said stable clusters electronically in a usable format as partitions in a transformation of said data structure.

2. The method according to claim 1, wherein gene clusters are used to look for partitions of tissues and tissue clusters are used to look for correlated clusters of genes.

3. The method according to claim 1, wherein said clustering comprises the superparamagnetic clustering algorithm.

4. The method according to claim 3, wherein said iteratively repeating to achieve stable clusters utilizes a measure for the stability of clusters and wherein clusters that are to be provided for said clustering configurations comprise those clusters identified as stable.

5. The method according to claim 1, which yields clusters of genes of correlated expression profiles that may participate in the same biological process.

6. The method according to claim 5, wherein said clusters of genes relate to administration of pharmaceutical drugs, or differentiate one type of cancer from another, or reflect the change of experimental protocol in a colon-cancer treatment.

7. The method according to claim 6, wherein said method identifies tissues of groups of patients, or tissues subjected to different experimental protocols, or identifies different types of cancer.

8. The method according to claim 7, wherein said method identifies different types of leukemia.

9. The method of claim 1, wherein said electronically output partitions comprise graphical partitions.

10. A method for analyzing data, available in the form of an array of numbers stored electronically in a data structure, wherein each row of the array represents measurements of the values taken by a particular attribute over several samples and each column represents the measurements of the various attributes taken for a particular sample for the analysis of gene expression data taken from several tissues, wherein the attributes are different genes for which expression levels were measured and the samples are human tissues or other biological material for which the expression levels of the genes have been determined, the method performed with an electronic processor, the method comprising:

measuring gene expression levels on a microarray to obtain said array of numbers;

performing cluster analysis in two ways, one way being in a gene dimension and a second way being in a sample dimension, over the samples and over the genes respectively, wherein the two ways of clustering are coupled: such that each cluster of genes constitutes a probe for clustering any group of samples, and each group of samples constitutes a probe for clustering any group of genes, wherein gene clusters are used to look for partitions of tissues and tissue clusters are used to look for correlated clusters of genes, and outputting said stable clusters electronically in usable format as partitions in a transformation of said data structure.

11. The method of claim 10, wherein said electronically output partitions comprise graphical partitions.

* * * * *